US007947268B2

(12) United States Patent
Baillie

(10) Patent No.: US 7,947,268 B2
(45) Date of Patent: May 24, 2011

(54) *SALMONELLA* BASED ORAL VACCINES FOR ANTHRAX

(75) Inventor: Leslie W. J. Baillie, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 12/084,998

(22) PCT Filed: Nov. 14, 2006

(86) PCT No.: PCT/US2006/044037

§ 371 (c)(1),
(2), (4) Date: Sep. 12, 2008

(87) PCT Pub. No.: WO2008/048289

PCT Pub. Date: Apr. 24, 2008

(65) Prior Publication Data

US 2009/0297556 A1 Dec. 3, 2009

Related U.S. Application Data

(60) Provisional application No. 60/736,457, filed on Nov. 14, 2005.

(51) Int. Cl.
*A01N 63/00* (2006.01)

(52) U.S. Cl. .................... 424/93.2; 424/93.4; 435/252.3

(58) Field of Classification Search ........................ None
See application file for complete search history.

(56) References Cited

U.S. PATENT DOCUMENTS

| | | | |
|---|---|---|---|
| 5,591,631 | A | 1/1997 | Leppla et al. |
| 5,677,274 | A | 10/1997 | Leppla et al. |
| 6,576,757 | B1 | 6/2003 | Punnonen et al. |
| 6,979,449 | B1 | 12/2005 | Mock |
| 2003/0003109 | A1 | 1/2003 | Galloway et al. |
| 2004/0009936 | A1 * | 1/2004 | Tang et al. ...................... 514/44 |
| 2004/0166120 | A1 | 8/2004 | Thomas et al. |
| 2004/0197343 | A1 | 10/2004 | Dubensky, Jr. et al. |
| 2005/0063986 | A1 * | 3/2005 | Bhatnagar et al. ......... 424/190.1 |
| 2005/0064391 | A1 | 3/2005 | Segal et al. |
| 2005/0112145 | A1 | 5/2005 | Hudson et al. |

FOREIGN PATENT DOCUMENTS

| | | | |
|---|---|---|---|
| WO | 0145639 | A2 | 6/2001 |
| WO | 0204646 | A1 | 1/2002 |
| WO | 2005026203 | A2 | 3/2005 |

OTHER PUBLICATIONS

Gustafsson et al (Trends in Biotechnology, 22(7):346-353, Jul. 2004).*

Dempsey et al (Science, 271(5247):348-350, 1996).*

Aloni-Grinstein, R., et al., "Oral Spore Vaccine Based on Live Attenuated Nontoxinogenic *Bacillus anthracis* Expressing Recombinant Mutant Protective A", "Infect. Immun.", Jul. 2005, pp. 4043-4053, vol. 73, No. 7.

Baillie, L.W., et al., "Abstract Only: Evaluation of *Bacillus subtilis* strain IS53 for the production of *Bacillus anthracis* protective antigen", "Lett. Appl. Microbiol.", Oct. 1994, pp. 225-227, vol. 19, No. 4.

Baillie, L., et al., "The expression of the protective antigen of *Bacillus anthracis* in *Bacillus subtilis*", "Journal of Applied Microbiology", 1998, pp. 741-746, vol. 84.

Baillie, L. W., et al., "Abstract Only: A heat-inducible *Bacillus subtilis* bacteriophage phi 105 expression system for the production of the . . . ", "FEMS Microbiology Lett.", Jun. 1, 1998, pp. 43-47, vol. 163, No. 1.

Baillie, L., "The development of new vaccines against *Bacillus anthracis*", "Journal of Applied Microbiology", 2001, pp. 609-613, vol. 91.

Baillie, L., et al., "Abstract Only: *Bacillus anthracis*, a bug with attitude!", "Cum. Opin. Microbiol.", eb. 2001, pp. 78-81, vol. 4, No. 1.

Baillie, Leslie, et al., "Abstract Only: Characterization of the human immune response to the U.K. human vaccine", "FEMS Immunoology and Medical Microbiology", 2004, pp. 267-270, vol. 42.

Ballard, Jimmy D., et al., "Anthrax toxin-mediated delivery of a cytotoxic T-cell epitope in vivo", "Proc. Natl. Acad. Sci.", Oct. 1996, pp. 12531-12534, vol. 93.

Ballard, Jimmy D., et al., "Anthrax Toxin as a Molecular Tool for Stimulation of Cytotoxic T Lymphocytes: Disulfide-Linked Epitopes, Multiple Inject", "Infect. Immun.", Oct. 1998, pp. 4696-4699, vol. 66, No. 10.

Ballard, Jimmy D., et al., "Anthrax Toxin-Mediated Delivery in Vivo and in Vitro of a Cytotoxic T-Lymphocyte Epitope from Ovalbumin", "Infect. Immun.", Feb. 1998, pp. 615-619, vol. 66, No. 2.

Cao, H., et al., "Abstract Only: Delivery of exogenous protein antigens to major historcompatibility complex class I pathway in cytosol", "J. Infect. Dis.", Jan. 15, 2002, pp. 244-251, vol. 185, No. 1.

Curtiss, Roy III, "Bacterial infectious disease control by vaccine development", "The Journal of Clinical Investigation", 2002, pp. 1061-1066, vol. 110, No. 8.

Doling, Amy M., et al., "Cytotoxic T-Lymphocyte Epitopes Fused to Anthrax Toxin Induce Protective Antiviral Immunity ", "Infect. Immun.", Jul. 1999, pp. 3290-3296, vol. 67, No. 7.

Flick-Smith, Helen C., et al., "Mucosal or Parenteral Administration of Microsphere-Associated *Bacillus anthracis* Protective Antigen Protects . . . ", "Infect. Immun.", Apr. 2002, pp. 2022-2028, vol. 70, No. 4.

(Continued)

*Primary Examiner* — Patricia A Duffy

(74) *Attorney, Agent, or Firm* — Kelly K. Reynolds; Steven J. Hultquist; Hultquist IP

(57) ABSTRACT

A vaccine for the prevention of anthrax, including a live, attenuated *Salmonella* and at least one nucleotide sequence encoding anthrax protective antigen (PA) or a fragment thereof and a nonlethal mutated form of anthrax lethal factor (LF) or a fragment thereof. In another implementation, the vaccine is constituted for the prevention of anthrax and at least one additional pathogen, as including a live, attenuated *Salmonella* and at least one nucleotide sequence encoding at least a fragment of a nonlethal mutated form of anthrax lethal factor (LF) and at least one nucleotide sequence encoding at least a fragment of an antigen of an additional pathogen. Vaccines of such types can be administered to stimulate antibody response in a subject, whereby the antibody response confers immunity to the subject.

2 Claims, 48 Drawing Sheets

OTHER PUBLICATIONS

Flick-Smith, Helen C., et al., "A recominant carboxy-terminal domain of the protective antigen of *Bacillus anthracis* protects mice against anthrax . . . ", "Infect. Immun.", Mar. 2002, pp. 1653-1656, vol. 70, No. 3.
Galen, James E., et al., "Adaptation of the endogenous *Salmonella enterica* serovar Typhi clyA-encoded hemolysin for antigen export enhances . . . ", "Infect. Immun.", Dec. 2004, pp. 7096-7106, vol. 72, No. 12.
Galloway, D., et al., "Abstract Only: Genetic immunization against anthrax", "Vaccine", Apr. 16, 2004, pp. 1604-1608, vol. 22, No. 13-14.
Garmory, Helen S., et al., "*Salmonella enterica* serovar typhimurium expressing a chromosomally integrated copy of the *Bacillus anthracis* . . . ", "Infect. Immun.", Jul. 2003, pp. 3831-3836, vol. 71, No. 7.
Hermanson, G., et al., "A cationic lipid-formulated plasmid DNA vaccine confers sustained antibody-mediated protection against aerosolized . . . ", "PNAS", Sep. 14, 2004, pp. 13601-13606, vol. 101, No. 37.
Hoffmaster, Alex R., et al., "Identification of anthrax toxin genes in a *Bacillus cereus* associated with an illness resembling inhalation anthrax", "PNAS", Jun. 1, 2004, pp. 8449-8454, vol. 101, No. 22.
Kang, Tae Jin, et al., "Murine Macrophages Kill the Vegetative Form of *Bacillus anthracis*", "Infect. Immun.", Nov. 2005, pp. 7495-7501, vol. 73, No. 11.
Klimpel, K.R., et al., "Abstract Only: Anthrax toxin lethal factor contains a zinc metalloprotease consensus sequence which is required . . . ", "Mol. Microbiol.", Sep. 1994, pp. 1093-1100, vol. 13, No. 6.
Kushner, Nicholas, et al., "A fragment of anthrax lethal factor delivers proteins to the cytosol without requiring protective antigen", "PNAS", May 27, 2003, pp. 6652-6657, vol. 100, No. 11.
Lim, Nam-Kyu, et al., "An anthrax lethal factor-neutralizing monoclonal antibody protects rats before and after challenge with anthrax toxin", "Infect. Immun.", Oct. 2005, pp. 6547-6551, vol. 73, No. 10.
Lu, Yichen, et al., "Genetically modified anthrax lethal toxin safely delivers whole HIV protein antigens into the cytosol to induce T cell . . . ", "PNAS", Jul. 5, 2000, pp. 8027-8032, vol. 97, No. 14.
McBride, B. W., et al., "Abstract Only: Protective efficacy of a recombinant protective antigen against *Bacillus anthracis* challenge and . . . ", "Vaccine", May 1998, pp. 810-817, vol. 16, No. 8.
Miller, J., et al., "Abstract Only: Production and purification of recombinant protective antigen and protective efficacy against *Bacillus* . . . ", "Lett. Appl. Microbiol.", Jan. 1998, pp. 56-60, vol. 26, No. 1.
Petosa, C., et al., "Abstract Only: Crystal structure of the anthrax toxin protective antigen", "Nature", Feb. 27, 1997, pp. 833-838, vol. 385, No. 6619.
Pezard, Corinne, et al., "Protective immunity induced by *Bacillus anthracis* toxin-deficient strains", "Infect. Immun.", Apr. 1995, pp. 1369-1372, vol. 63, No. 4.
Pomerantsev, A. P., et al., "Abstract Only: Expression of cereolysine AB genes in *Bacillus anthracis* vaccine strain ensures protection against . . . ", "Vaccine", Dec. 1997, pp. 1846-1850, vol. 15, No. 17-18.
Price, Brian M., et al., "Protection against Anthrax Lethal Toxin Challenge by Genetic Immunization with a Plasmid Encoding the Lethal Factor . . . ", "Infect. Immun.", Jul. 2001, pp. 4509-4515, vol. 69, No. 7.
Read, T.D., et al., "Abstract Only: The genome sequence of *Bacillus anthracis* Ames and comparison to closely related bacteria", "Nature", May 1, 2003, pp. 81-86, vol. 423, No. 6935.
Rosovitz, M. J., et al., "Alanine-scanning mutations in domain 4 of anthrax toxin protective antigen reveal residues important for binding to . . . ", "The Journal of Biological Chemistry", Aug. 15, 2003, pp. 30936-30944, vol. 278, No. 33.
Ross, Ted M., et al., "Abstract Only: C3d enhancement of antibodies to hemagglutinin accelerates protection against influenza virus challenge", "Nature Immunology", 2000, pp. 127-131, vol. 1, No. 2.
Thwaite, Joanne E., et al., "Optimization of the cell wall microenvironment allows increased production of recombinant *Bacillus anthracis* . . . ", "Applied and Environmental Microbiology", Jan. 2002, pp. 227-234, vol. 68, No. 1.
Vindurampulle, Christofer J., et al., "Abstract Only: Recombinant *Salmonella enterica* serovar Typhi in a prime-boost strategy", "Vaccine", Sep. 9, 2004, pp. 3744-3750, vol. 22, No. 27-28.
Williams, Rachel C., et al., "Production of *Bacillus anthracis* protective antigen is dependent on the extracellular chaperon, PrsA", "The Journal of Biological Chemistry", May 16, 2003, pp. 18056-18062, vol. 278, No. 20.
Zegers, N. D., et al., "Expression of the protective antigen of *Bacillus anthracis* by *Lactobacillus casei*: towards the development of an oral . . . ", "Journal of Applied Microbiology", 1999, pp. 309-314, vol. 87.
Baillie, L.W., et al, "Evaluation of *Bacillus subtilis* strain IS53 for the production of *Bacillus anthracis* protective antigen", "Lett. Appl. Microbiol.", Oct. 1994, pp. 225-227, vol. 19, No. 4.
Baillie, Leslie, et al., "Characterization of the human immune response to the U.K. human vaccine", "FEMS Immunoology and Medical Microbiology", 2004, pp. 267-270, vol. 42.
Baillie, L. W., et al, "A heat-inducible *Bacillus subtilis* bacteriophage phi 105 expression system for the production of the . . . ", "FEMS Microbiology Lett.", Jun. 1, 1998, pp. 43-47, vol. 163, No. 1.
Baillie, L., et al., "*Bacillus anthracis*, a bug with attitude!", "Curr. Opin. Microbiol.", Feb. 2001, pp. 78-81, vol. 4, No. 1.
Cao, H., et al., "Delivery of exogenous protein antigens to major historcompatibility complex class I pathway in cytosol", "J. Infect. Dis.", Jan. 15, 2002, pp. 244-251, vol. 185, No. 1.
Galloway, D., et al, "Genetic immunization against anthrax", "Vaccine", Apr. 16, 2004, pp. 1604-1608, vol. 22, No. 13-14.
Klimpel, K.R., et al., "Anthrax toxin lethal factor contains a zinc metalloprotease consensus sequence which is required . . . ", "Mol. Microbiol.", Sep. 1994, pp. 1093-1100, vol. 13, No. 6.
McBride, B. W., et al., "Protective efficacy of a recombinant protective antigen against *Bacillus anthracis* challenge and . . . ", "Vaccine", May 1998, pp. 810-817, vol. 16, No. 8.
Miller, J., et al., "Production and purification of recombinant protective antigen and protective efficacy against *Bacillus* . . . ", "Lett. Appl. Microbiol.", Jan. 1998, pp. 56-60, vol. 26, No. 1.
Petosa, C., et al., "Crystal structure of the anthrax toxin protective antigen", "Nature", Feb. 27,1997, pp. 833-838, vol. 385, No. 6619.
Pomerantsev, A. P., et al., "Expression of cereolysine AB genes in *Bacillus anthracis* vaccine strain ensures protection against . . . ", "Vaccine", Dec. 1997, pp. 1846-1850, vol. 15, No. 17-18.
Read, T.D., et al., "The genome sequence of *Bacillus anthracis* Ames and comparison to closely related bacteria", "Nature", May 1, 2003, pp. 81-86, vol. 423, No. 6935.
Poff-Reichow, Sally Ann, Abstract and Title Page, "Development of *Brucella abortus* RB51 as a Vaccine to Protect Against Brucellosis and Anthrax", Mar. 10, 2004, Published in: US.
Poff-Reichow, Sally Ann, "Development of *Brucella abortus* RB51 as a Vaccine to Protect Against Brucellosis and Anthrax", Mar. 10, 2004, Published in: US.
Ross, Ted M., et al., "C3d enhancement of antibodies to hemagglutinin accelerates protection against influenza virus challenge", "Nature Immunology", 2000, pp. 127-131, vol. 1, No. 2.
Vindurampulle, Christofer J., et al., "Recombinant *Salmonella enterica* serovar Typhi in a prime-boost strategy", "Vaccine", Sep. 9, 2004, pp. 3744-3750, vol. 22, No. 27-28.
Chabalgoity, J. et al. , "*Salmonella typhimurium* as a basis for a live oral *Echinoccus granulosus* vaccine", "Vaccine", pp. 460-469, vol. 19.
Mendelson, I. et al., "Efficacious, nontoxic *Bacillus anthracis* spore vaccines based on strains expressing mutant variants of lethal toxin", "Vaccine", Feb. 19, 2005, pp. 5688-5697, vol. 23.
Stokes, M et al. , "Oral Administration of a *Salmonella enterica* Based Vaccine Expressing *Bacillus anthracis* Protective Antigens confers . . . ", "Infection and Immunity", Dec. 4, 2006, p. 2007, vol. 75, No. 4.
Hammond, S. et al. , "Lethal Factor Active-Site Mutations Affect Catalytic Activity in Vitro", "Infection and Immunity", May 1998, pp. 2374-2378, vol. 66, No. 5.

* cited by examiner

THE ANTHRAX TOXIN CELL UPTAKE MODEL

HUMAN SERUM SAMPLES WHERE OBTAINED FROM VACCINATED (US AND UK LICENSED ANTHRAX VACCINES) AND INFECTED INDIVIDUALS WHO HAD BEEN TREATED FOR CUTANEOS ANTHRAX. SAMPLES WERE ANALYZED FOR THE PRESENCE OF ANTIBODIES TO PA, LF AND EF BY ELIZA

TITERS OF ANTIBODIES TO LF DOMAIN 1 PROTEIN (A) OR PA (B) IN THE SERA OF BALB/c MICE IMMUNIZED WITH DNA PLASMIDS ENCODING PA (pCPA) LF DOMAIN 1 (pCLF4) OR A COMBINATION OF pCPA AND pCLF4 (PRICE et al., 2001)

PA SPECIFIC IgG ANTIBODIES FROM 4 ANDIVIDUALS (A-D) RECEIVING THE UK VACCINE, INHIBIT BINDING OF THE PA SPECIFIC MOUSE MONOCLONAL ANTIBODY 2D3 (1:50)

PA ANTIBODIES NEUTRALIZING ANTIBODIES

THE KNOWN TOXIN NEUTRALIZING ANTIBODY DOMAINS OF PA

A LFn EPITOPE DELIVERY CONSTRUCT

A MODEL OF ANTIGEN UPTAKE USING THE PROPOSED SALMONELLA MODEL

LF DOMAIN IMMUNOGENICITY STUDIES

LF DOMAINS 3 AND 4 SHOWED NO DETECTABLE TOXIN NEUTRALIZING ACTIVITY WITH A STARTING DILUTION OF 1 IN 100

*BIOLOGICALLY INACTIVE

GROUP (10 Balb/c mice) TOXIN NEUTRALIZATION TITERS FROM MICE IMMUNIZED WITH LF*, LF DOMAINS OR PA A SUMMARY OF THE TNA TITERS FOR LF D1 AND FULL LENGTH BIOLOGICALLY INACTIVE LF IN THE PRESENCE OF PA SURVIVAL OF A/J MICE CHALLENGED WITH B. anthracis STI SPORES BY THE i.p. ROUTE AFTER IMMUNIZATION WITH rLF PROTEINS

ANTI-SPORE ACTIVITY 1 2 3 4 5 6 7 8 9

1=MW LADDER; 2=PA; 3=LF; 4=MW LADDER; 5=LFD1; 6=LFD2; 7=LFD3; 8=LFD4; 9=LFD2-4

WESTERN BLOT OF PA AND LF DOMAINS WITH SERUM FROM A RABBIT EXPOSED TO B. cereus G9241

FIG.16A

ORGANISM: CUSTOM SPECIFIED
GENE NAME:
SEQUENCE TYPE: DNA
OPTIMIZATION REGION: 1 - 2331
MINIMUM CODON FREQUENCY: 18
CUTOFF FOR SECONDARY STRUCTURE: 30 (LOCAL)
CYCLES OF SECONDARY STRUCTURE OPTIMIZATION: 1
GC RANGE: 40 - 60
CONSECUTIVE CODON: 1
REPETITIVE CODON:
5' ADDITIONAL SEQUENCE: CCGAGGATCC
3' ADDITIONAL SEQUENCE: AAGCTTTCGG
GENETIC CODE: 1
RE SITES:BAMHI(GGATCC), HINDIII(AAGCTT)
RE CHECK SITES: SMAI(CCCGGG), ECORV(GATATC)
RE KEEP SITES:

ALIGNMENT (OPTIMIZED REGION). THE CHANGED CODONS ARE INDICATED AS LETTERS OUTLINED IN A BOX:

| |
|---|
| FIG.16A |
| FIG.16B |
| FIG.16C |
| FIG.16D |
| FIG.16E |
| FIG.16F |
| FIG.16G |

FIG.16

```
OPTIMIZED 1   GCGGGCGGTCATGGTGATGTTGGTATGCATGTTAAAGAGAAAGAGAAAAATAAAGATGAG
ORIGINAL  1   GCGGGCGGTCATGGTGATGTAGGTATGCACGTAAAAGAGAAAGAGAAAAATAAAGATGAG

OPTIMIZED 61  AATAAACGTAAAGATGAAGAGCGTAATAAAACCCAGGAAGAGCATCTGAAAGAAATCATG
ORIGINAL  61  AATAAGAGAAAAGATGAAGAACGAAATAAAACACAGGAAGAGCATTTAAAGGAAATCATG

OPTIMIZED 121 AAACATATTGTTAAAATTGAAGTTAAAGGCGAGGAAGCCGTTAAAAAAGAGGCAGCCGAA
ORIGINAL  121 AAACACATTGTAAAAATAGAAGTAAAAGGGGAGGAAGCTGTTAAAAAAGAGGCAGCAGAA

OPTIMIZED 181 AAACTGCTGGAGAAAGTTCCGAGCGATGTTCTGGAGATGTATAAAGCAATTGGCGGTAAA
ORIGINAL  181 AAGCTACTTGAGAAAGTACCATCTGATGTTTTAGAGATGTATAAAGCAATTGGAGGAAAG

OPTIMIZED 241 ATCTATATTGTGGATGGTGATATTACCAAACATATTAGCCTGGAAGCACTGAGCGAAGAT
ORIGINAL  241 ATATATATTGTGGATGGTGATATTACAAAACATATATCTTTAGAAGCATTATCTGAAGAT

OPTIMIZED 301 AAGAAGAAAATTAAAGACATCTATGGCAAAGATGCCCTGCTGCATGAACATTATGTTTAT
ORIGINAL  301 AAGAAAAAAATAAAAGACATTTATGGAAAGATGCTTTATTACATGAACATTATGTATAT

OPTIMIZED 361 GCAAAAGAAGGCTATGAACCGGTTCTGGTTATCCAGAGCAGCGAAGATTATGTTGAAAAT
ORIGINAL  361 GCAAAAGAAGGATATGAACCCGTACTTGTAATCCAATCTTCGGAAGATTATGTAGAAAAT
```

FIG. 16B

| | | |
|---|---|---|
| OPTIMIZED | 421 | ACCGAAAAAGCACTGAACGTTTATTATGAAATTGGTAAAATTCTGAGCCGTGATATTCTG |
| ORIGINAL | 421 | ACTGAAAAGGCACTGAACGTTTATTATGAAATAGGTAAGATATTATCAAGGGATATTTTA |
| OPTIMIZED | 481 | AGCAAAATTAATCAGCCGTATCAGAAATTTCTGGATGTTCTGAATACCATTAAAAATGCA |
| ORIGINAL | 481 | AGTAAAATTAATCAACCATATCAGAAATTTTTAGATGTATTAAATACCATTAAAAATGCA |
| OPTIMIZED | 541 | AGCGATAGCGATGGCCAGGATCTGCTGTTTACCAATCAGCTGAAAGAACATCCGACCGAC |
| ORIGINAL | 541 | TCTGATTCAGATGGACAAGATCTTTTATTTACTAATCAGCTTAAGGAACATCCCACAGAC |
| OPTIMIZED | 601 | TTTAGCGTTGAATTTCTGGAACAGAATAGCAATGAGGTTCAGGAAGTTTTTGCGAAAGCC |
| ORIGINAL | 601 | TTTTCTGTAGAATTCTTGGAACAAAATAGCAATGAGGTACAAGAAGTATTTGCGAAAGCT |
| OPTIMIZED | 661 | TTTGCATATTATATCGAGCCGCAGCATCGTGATGTTCTGCAGCTGTATGCACCGGAAGCC |
| ORIGINAL | 661 | TTTGCATATTATATCGAGCCACAGCATCGTGATGTTTTACAGCTTTATGCACCGGAAGCT |
| OPTIMIZED | 721 | TTTAATTATATGGATAAGTTTAACGAACAGGAAATTAATCTGAGCCTGGAAGAGCTGAAA |
| ORIGINAL | 721 | TTTAATTACATGGATAAATTTAACGAACAAGAAATAAATCTATCCTTGGAAGAACTTAAA |
| OPTIMIZED | 781 | GATCAGCGTATGCTGAGCCGTTATGAAAAATGGGAAAAAATTAAACAGCATTATCAGCAT |
| ORIGINAL | 781 | GATCAACGGATGCTGTCAAGATATGAAAAATGGGAAAAGATAAAACAGCACTATCAACAC |

FIG.16C

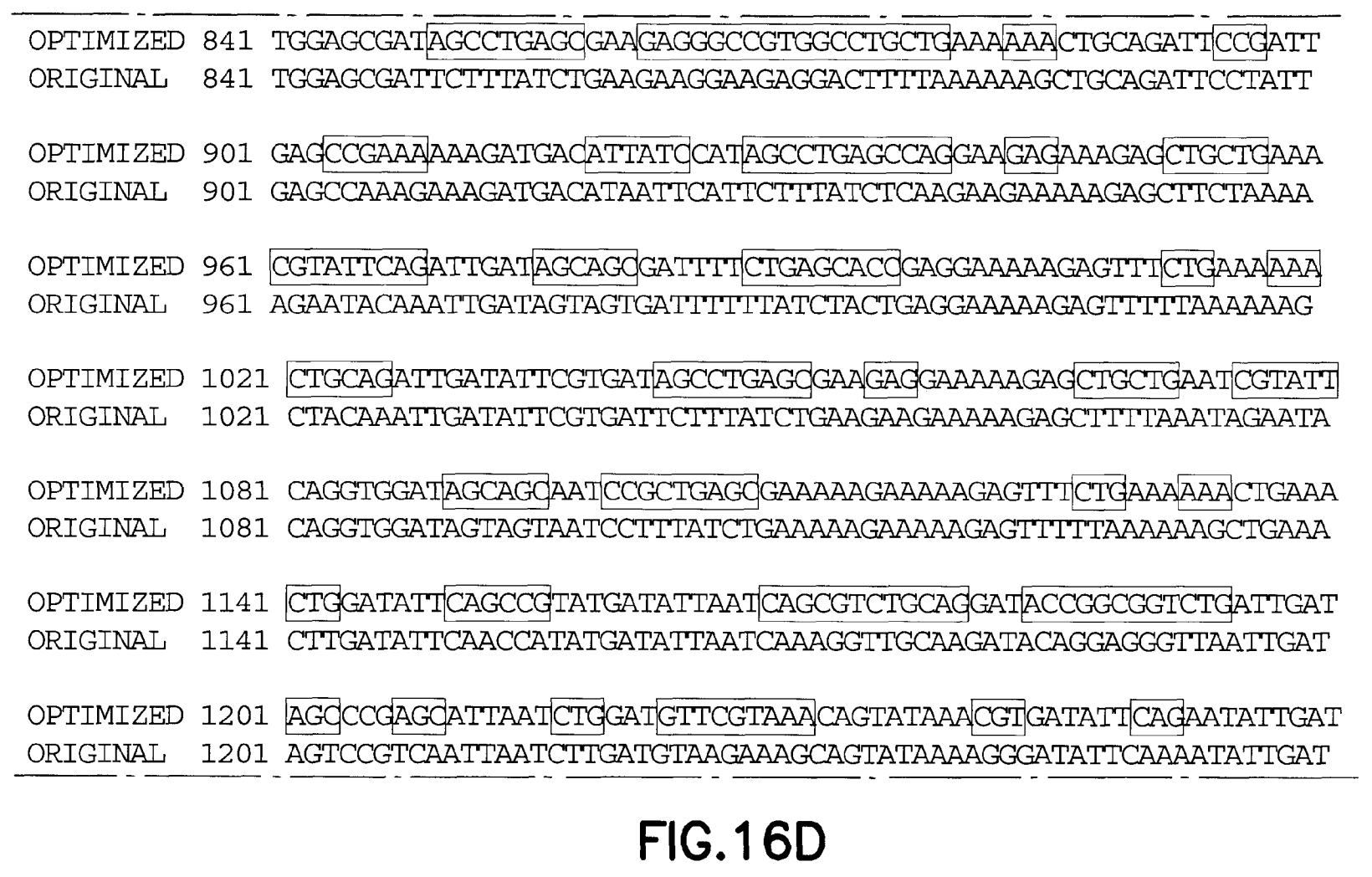

```
OPTIMIZED 841  TGGAGCGATAGCCTGAGCGAAGAGGGCCGTGGCCTGCTGAAAAAACTGCAGATTCCGATT
ORIGINAL  841  TGGAGCGATTCTTTATCTGAAGAAGGAAGAGGACTTTTAAAAAAGCTGCAGATTCCTATT

OPTIMIZED 901  GAGCCGAAAAAAGATGACATTATCCATAGCCTGAGCCAGGAAGAGAAAGAGCTGCTGAAA
ORIGINAL  901  GAGCCAAAGAAAGATGACATAATTCATTCTTTATCTCAAGAAGAAAAAGAGCTTCTAAAA

OPTIMIZED 961  CGTATTCAGATTGATAGCAGCGATTTTCTGAGCACCGAGGAAAAAGAGTTTCTGAAAAAA
ORIGINAL  961  AGAATACAAATTGATAGTAGTGATTTTTATCTACTGAGGAAAAAGAGTTTTTAAAAAAG

OPTIMIZED 1021 CTGCAGATTGATATTCGTGATAGCCTGAGCGAAGAGGAAAAAGAGCTGCTGAATCGTATT
ORIGINAL  1021 CTACAAATTGATATTCGTGATTCTTTATCTGAAGAAGAAAAAGAGCTTTTAAATAGAATA

OPTIMIZED 1081 CAGGTGGATAGCAGCAATCCGCTGAGCGAAAAAGAAAAAGAGTTTCTGAAAAAACTGAAA
ORIGINAL  1081 CAGGTGGATAGTAGTAATCCTTTATCTGAAAAAGAAAAAGAGTTTTTAAAAAAGCTGAAA

OPTIMIZED 1141 CTGGATATTCAGCCGTATGATATTAATCAGCGTCTGCAGGATACCGGCGGTCTGATTGAT
ORIGINAL  1141 CTTGATATTCAACCATATGATATTAATCAAAGGTTGCAAGATACAGGAGGGTTAATTGAT

OPTIMIZED 1201 AGCCCGAGCATTAATCTGGATGTTCGTAAACAGTATAAACGTGATATTCAGAATATTGAT
ORIGINAL  1201 AGTCCGTCAATTAATCTTGATGTAAGAAAGCAGTATAAAAGGGATATTCAAAATATTGAT
```

FIG. 16D

| | | |
|---|---|---|
| OPTIMIZED | 1261 | GCCCTGCTGCATCAGAGCATTGGCAGCACCCTGTATAATAAAATCTATCTGTATGAAAAT |
| ORIGINAL | 1261 | GCTTTATTACATCAATCCATTGGAAGTACCTTGTACAATAAAATTTATTTGTATGAAAAT |
| OPTIMIZED | 1321 | ATGAATATCAATAACCTGACCGCAACCCTGGGTGCGGATCTGGTTGATAGCACCGATAAT |
| ORIGINAL | 1321 | ATGAATATCAATAACCTTACAGCAACCCTAGGTGCGGATTTAGTTGATTCCACTGATAAT |
| OPTIMIZED | 1381 | ACCAAAATTAATCGTGGTATTTTTAATGAGTTTAAGAAAAATTTTAAATATAGCATTAGC |
| ORIGINAL | 1381 | ACTAAAATTAATAGAGGTATTTTCAATGAATTCAAAAAAAATTTCAAATATAGTATTTCT |
| OPTIMIZED | 1441 | AGCAACTATATGATTGTTGATATTAATGAACGTCCGGCACTGGATAATGAGCGTCTGAAA |
| ORIGINAL | 1441 | AGTAACTATATGATTGTTGATATAAATGAAAGGCCTGCATTAGATAATGAGCGTTTGAAA |
| OPTIMIZED | 1501 | TGGCGTATCCAGCTGAGCCCGGATACCCGTGCAGGCTATCTGGAAAATGGCAAACTGATT |
| ORIGINAL | 1501 | TGGAGAATCCAATTATCACCAGATACTCGAGCAGGATATTTAGAAAATGGAAAGCTTATA |
| OPTIMIZED | 1561 | CTGCAGCGTAACATCGGTCTGGAAATTAAAGATGTTCAGATTATCAAACAGAGCGAAAAA |
| ORIGINAL | 1561 | TTACAAAGAAACATCGGTCTGGAAATAAAGGATGTACAAATAATTAAGCAATCCGAAAAA |
| OPTIMIZED | 1621 | GAATATATTCGTATTGATGCGAAAGTTGTGCCGAAAAGCAAAATTGATACCAAAATTCAG |
| ORIGINAL | 1621 | GAATATATAAGGATTGATGCGAAAGTAGTGCCAAAGAGTAAAATAGATACAAAAATTCAA |

FIG. 16E

```
OPTIMIZED 1681 GAAGCACAGCTGAATATTAATCAGGAATGGAATAAAGCACTGGGCCTGCCGAAATATACC
ORIGINAL  1681 GAAGCACAGTTAAATATAAATCAGGAATGGAATAAAGCATTAGGGTTACCAAAATATACA

OPTIMIZED 1741 AAACTGATTACCTTTAACGTGCATAATCGTTATGCAAGCAATATTGTTGAAAGCGCCTAT
ORIGINAL  1741 AAGCTTATTACATTCAACGTGCATAATAGATATGCATCCAATATTGTAGAAAGTGCTTAT

OPTIMIZED 1801 CTGATTCTGAATGAATGGAAAAATAACATTCAGAGCGATCTGATTAAAAAAGTTACCAAT
ORIGINAL  1801 TTAATATTGAATGAATGGAAAAATAATATTCAAAGTGATCTTATAAAAAAGGTAACAAAT

OPTIMIZED 1861 TATCTGGTTGATGGTAATGGCCGTTTTGTTTTTACCGATATTACCCTGCCGAATATTGCC
ORIGINAL  1861 TACTTAGTTGATGGTAATGGAAGATTTGTTTTTACCGATATTACTCTCCCTAATATAGCT

OPTIMIZED 1921 GAACAGTATACCCATCAGGATGAGATCTATGAGCAGGTTCATAGCAAAGGCCTGTATGTT
ORIGINAL  1921 GAACAATATACACATCAAGATGAGATATATGAGCAAGTTCATTCAAAAGGGTTATATGTT

OPTIMIZED 1981 CCGGAAAGCCGTAGCATTCTGCTGCATGGCCCGAGCAAAGGTGTTGAACTGCGTAATGAT
ORIGINAL  1981 CCAGAATCCCGTTCTATATTACTCCATGGACCTTCAAAAGGTGTAGAATTAAGGAATGAT

OPTIMIZED 2041 AGCGAGGGTTTTATTCATTGTTTTGGCCATGCCGTGGATGACTATGCCGGCTATCTGCTG
ORIGINAL  2041 AGTGAGGGTTTTATACACTGCTTTGGACATGCTGTGGATGATTATGCTGGATATCTATTA
```

FIG. 16F

```
OPTIMIZED 2101 GATAAAAACCAGAGCGATCTGGTTACCAATAGCAAAAAGTTTATTGATATTTTTAAAGAA
ORIGINAL  2101 GATAAGAACCAATCTGATTTAGTTACAAATTCTAAAAAATTCATTGATATTTTTAAGGAA

OPTIMIZED 2161 GAGGGCAGCAATCTGACCAGCTATGGCCGTACCAATGAAGCGGAATTCTTTGCAGAAGCC
ORIGINAL  2161 GAAGGGAGTAATTTAACTTCGTATGGGAGAACAAATGAAGCGGAATTTTTTGCAGAAGCC

OPTIMIZED 2221 TTTCGTCTGATGCATAGCACCGACCATGCCGAACGTCTGAAAGTTCAGAAAAATGCCCCG
ORIGINAL  2221 TTTAGGTTAATGCATTCTACGGACCATGCTGAACGTTTAAAAGTTCAAAAAAATGCTCCG

OPTIMIZED 2281 AAAACCTTTCAGTTTATTAACGATCAGATTAAGTTTATTATCAACAGCTAA
ORIGINAL  2281 AAAACTTTCCAATTTATTAACGATCAGATTAAGTTCATTATTAACTCATAA
```

FIG.16G

| |
|---|
| FIG.17A |
| FIG.17B |
| FIG.17C |

>Optimized Sequence Length: 2351, GC%:40.66
CCGAGGATCCGCGGGCGGTCATGGTGATGTTGGTATGCATGTTAAAGAGAAAGAGAAAAA
TAAAGATGAGAATAAACGTAAAGATGAAGAGCGTAATAAAACCCAGGAAGAGCATCTGAA
AGAAATCATGAAACATATTGTTAAAATTGAAGTTAAAGGCGAGGAAGCCGTTAAAAAAGA
GGCAGCCGAAAAACTGCTGGAGAAAGTTCCGAGCGATGTTCTGGAGATGTATAAAGCAAT
TGGCGGTAAAATCTATATTGTGGATGGTGATATTACCAAACATATTAGCCTGGAAGCACT
GAGCGAAGATAAGAAGAAAATTAAAGACATCTATGGCAAAGATGCCCTGCTGCATGAACA
TTATGTTTATGCAAAAGAAGGCTATGAACCGGTTCTGGTTATCCAGAGCAGCGAAGATTA
TGTTGAAAATACCGAAAAAGCACTGAACGTTTATTATGAAATTGGTAAAATTCTGAGCCG
TGATATTCTGAGCAAAATTAATCAGCCGTATCAGAAATTTCTGGATGTTCTGAATACCAT
TAAAAATGCAAGCGATAGCGATGGCCAGGATCTGCTGTTTACCAATCAGCTGAAAGAACA
TCCGACCGACTTTAGCGTTGAATTTCTGGAACAGAATAGCAATGAGGTTCAGGAAGTTTT TGCGAAAGCCTTTGCATATTATATCGAGCCGCAGCATCGTGATGTTCTGCAGCTGTATGC
ACCGGAAGCCTTTAATTATATGGATAAGTTTAACGAACAGGAAATTAATCTGAGCCTGGA
AGAGCTGAAAGATCAGCGTATGCTGAGCCGTTATGAAAAATGGGAAAAAATTAAACAGCA
TTATCAGCATTGGAGCGATAGCCTGAGCGAAGAGGGCCGTGGCCTGCTGAAAAAACTGCA
GATTCCGATTGAGCCGAAAAAAGATGACATTATCCATAGCCTGAGCCAGGAAGAGAAAGA
GCTGCTGAAACGTATTCAGATTGATAGCAGCGATTTTCTGAGCACCGAGGAAAAAGAGTT
TCTGAAAAAACTGCAGATTGATATTCGTGATAGCCTGAGCGAAGAGGAAAAAGAGCTGCT
GAATCGTATTCAGGTGGATAGCAGCAATCCGCTGAGCGAAAAAGAAAAAGAGTTTCTGAA
AAAACTGAAACTGGATATTCAGCCGTATGATATTAATCAGCGTCTGCAGGATACCGGCGG
TCTGATTGATAGCCCGAGCATTAATCTGGATGTTCGTAAACAGTATAAACGTGATATTCA
GAATATTGATGCCCTGCTGCATCAGAGCATTGGCAGCACCCTGTATAATAAAATCTATCT
GTATGAAAATATGAATATCAATAACCTGACCGCAACCCTGGGTGCGGATCTGGTTGATAG
CACCGATAATACCAAAATTAATCGTGGTATTTTTAATGAGTTTAAGAAAAATTTTAAATA
TAGCATTAGCAGCAACTATATGATTGTTGATATTAATGAACGTCCGGCACTGGATAATGA
GCGTCTGAAATGGCGTATCCAGCTGAGCCCGGATACCCGTGCAGGCTATCTGGAAAATGG
CAAACTGATTCTGCAGCGTAACATCGGTCTGGAAATTAAAGATGTTCAGATTATCAAACA
GAGCGAAAAAGAATATATTCGTATTGATGCGAAAGTTGTGCCGAAAAGCAAAATTGATAC
CAAAATTCAGGAAGCACAGCTGAATATTAATCAGGAATGGAATAAAGCACTGGGCCTGCC
GAAATATACCAAACTGATTACCTTTAACGTGCATAATCGTTATGCAAGCAATATTGTTGA
AAGCGCCTATCTGATTCTGAATGAATGGAAAAATAACATTCAGAGCGATCTGATTAAAAA
AGTTACCAATTATCTGGTTGATGGTAATGGCCGTTTTGTTTTTACCGATATTACCCTGCC
GAATATTGCCGAACAGTATACCCATCAGGATGAGATCTATGAGCAGGTTCATAGCAAAGG
CCTGTATGTTCCGGAAAGCCGTAGCATTCTGCTGCATGGCCCGAGCAAAGGTGTTGAACT

FIG.17B

```
GCGTAATGATAGCGAGGGTTTTATTCATTGTTTTGGCCATGCCGTGGATGACTATGCCGG
CTATCTGCTGGATAAAAACCAGAGCGATCTGGTTACCAATAGCAAAAAGTTTATTGATAT
TTTTAAAGAAGAGGGCAGCAATCTGACCAGCTATGGCCGTACCAATGAAGCGGAATTCTT
TGCAGAAGCCTTTCGTCTGATGCATAGCACCGACCATGCCGAACGTCTGAAAGTTCAGAA
AAATGCCCCGAAAACCTTTCAGTTTATTAACGATCAGATTAAGTTTATTATCAACAGCTA
AAAGCTTTCGG

Restriction Enzyme Sites:
    BamHI (GGATCC) : 1  (5)
    HindIII (AAGCTT) : 1  (2342)
    SmaI (CCCGGG)     :0
    EcoRV (GATATC)   :0
```

Protein Alignment - Optimized (TOP) vs. Original (BOTTOM):

```
1   AGGHGDVGMHVKEKEKNKDENKRKDEERNKTQEEHLKEIMKHIVKIEVKGEEAVKKEAAE
1   AGGHGDVGMHVKEKEKNKDENKRKDEERNKTQEEHLKEIMKHIVKIEVKGEEAVKKEAAE

61  KLLEKVPSDVLEMYKAIGGKIYIVDGDITKHISLEALSEDKKKIKDIYGKDALLHEHYVY
61  KLLEKVPSDVLEMYKAIGGKIYIVDGDITKHISLEALSEDKKKIKDIYGKDALLHEHYVY

121 AKEGYEPVLVIQSSEDYVENTEKALNVYYEIGKILSRDILSKINQPYQKFLDVLNTIKNA
121 AKEGYEPVLVIQSSEDYVENTEKALNVYYEIGKILSRDILSKINQPYQKFLDVLNTIKNA

181 SDSDGQDLLFTNQLKEHPTDFSVEFLEQNSNEVQEVFAKAFAYYIEPQHRDVLQLYAPEA
181 SDSDGQDLLFTNQLKEHPTDFSVEFLEQNSNEVQEVFAKAFAYYIEPQHRDVLQLYAPEA

241 FNYMDKFNEQEINLSLEELKDQRMLSRYEKWEKIKQHYQHWSDSLSEEGRGLLKKLQIPI
241 FNYMDKFNEQEINLSLEELKDQRMLSRYEKWEKIKQHYQHWSDSLSEEGRGLLKKLQIPI
```

```
301 EPKKDDIIHSLSQEEKELLKRIQIDSSDFLSTEEKEFLKKLQIDIRDSLSEEEKELLNRI
301 EPKKDDIIHSLSQEEKELLKRIQIDSSDFLSTEEKEFLKKLQIDIRDSLSEEEKELLNRI

361 QVDSSNPLSEKEKEFLKKLKLDIQPYDINQRLQDTGGLIDSPSINLDVRKQYKRDIQNID
361 QVDSSNPLSEKEKEFLKKLKLDIQPYDINQRLQDTGGLIDSPSINLDVRKQYKRDIQNID

421 ALLHQSIGSTLYNKIYLYENMNINNLTATLGADLVDSTDNTKINRGIFNEFKKNFKYSIS
421 ALLHQSIGSTLYNKIYLYENMNINNLTATLGADLVDSTDNTKINRGIFNEFKKNFKYSIS

481 SNYMIVDINERPALDNERLKWRIQLSPDTRAGYLENGKLILQRNIGLEIKDVQIIKQSEK
481 SNYMIVDINERPALDNERLKWRIQLSPDTRAGYLENGKLILQRNIGLEIKDVQIIKQSEK

541 EYIRIDAKVVPKSKIDTKIQEAQLNINQEWNKALGLPKYTKLITFNVHNRYASNIVESAY
541 EYIRIDAKVVPKSKIDTKIQEAQLNINQEWNKALGLPKYTKLITFNVHNRYASNIVESAY

601 LILNEWKNNIQSDLIKKVTNYLVDGNGRFVFTDITLPNIAEQYTHQDEIYEQVHSKGLYV
601 LILNEWKNNIQSDLIKKVTNYLVDGNGRFVFTDITLPNIAEQYTHQDEIYEQVHSKGLYV

661 PESRSILLHGPSKGVELRNDSEGFIHCFGHAVDDYAGYLLDKNQSDLVTNSKKFIDIFKE
661 PESRSILLHGPSKGVELRNDSEGFIHCFGHAVDDYAGYLLDKNQSDLVTNSKKFIDIFKE

721 EGSNLTSYGRTNEAEFFAEAFRLMHSTDHAERLKVQKNAPKTFQFINDQIKFIINS*
721 EGSNLTSYGRTNEAEFFAEAFRLMHSTDHAERLKVQKNAPKTFQFINDQIKFIINS*
```

FIG.18B

DOMAIN RECOGNITION OF IQNLF.
PANELS A AND B ARE WESTERN BLOTS PROBED WITH IQNLF AND LOADED WITH A MARKER (LEFT AND RIGHT LANES) AND EQUAL AMOUNDS OF FULL LENGTH rLF (LANE 1) , LF DOMAIN (LANE 2), LF DOMAIN II (LANE 3), LF DOMAIN III (LANE 4), LF DOMAIN IV (LANE 5), AND LF DOMAINS II–IV (LANE 6).
PANELS A IS A NATIVE BLOT WHILE B IS AN SDS–DENATURING BLOT

LANES:
1)BIO-RAD LOW RANGE STANDARDS; 2)SL3261/pSEC10-LFnN#26;
3)SL3261/pSEC10-LFnN#29; 4)SL3261/pSEC10-LFnN#31;
5)SL3261/pSEC10-LFoN#26; 6)SL3261/pSEC10-LFoN#27;
7)SL3261/pSEC10-LFoN#33; 8)RECOMBINANT LF DOM1;
9)E.coli TOP10/pSEC10; 10)BIO-RAD LOW RANGE STANDARDS.
PROBED WITH MOUSE MONOCLONAL ANTIBODY TO LF DOMAIN 1

EXPRESSION OF LF DOMAIN 1 IN S.enterica serovar Typhimurium SL3261

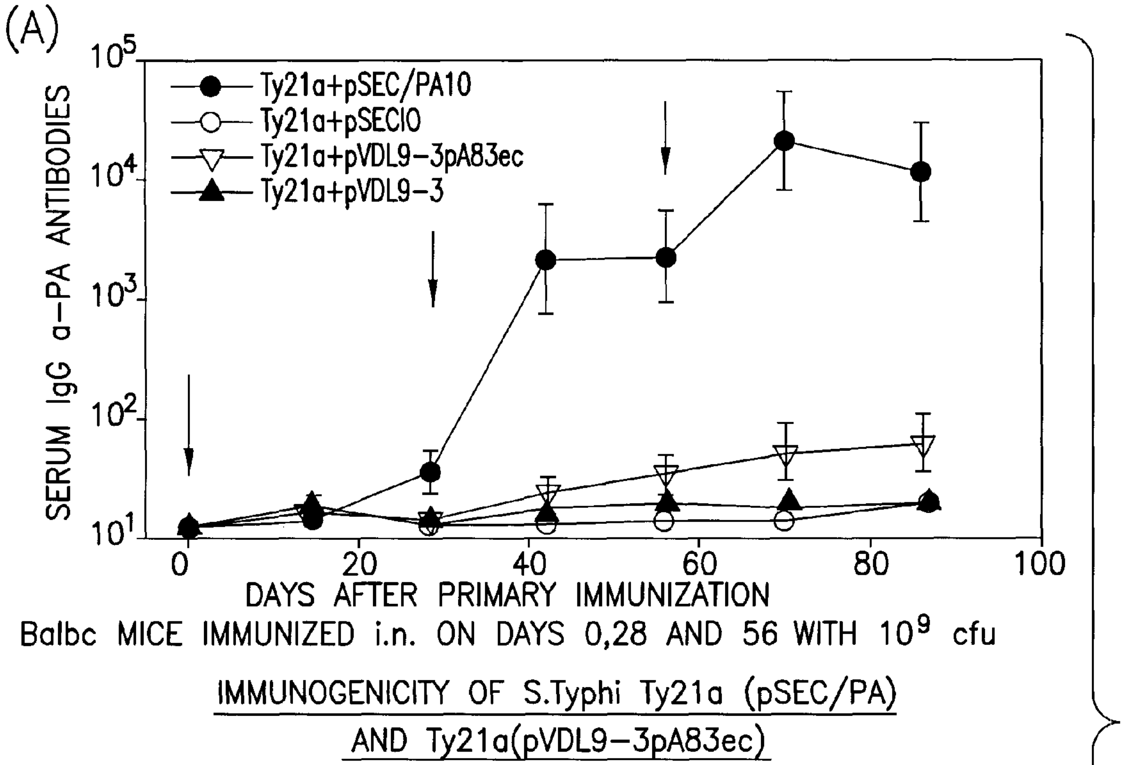
Balbc MICE IMMUNIZED i.n. ON DAYS 0,28 AND 56 WITH $10^9$ cfu
IMMUNOGENICITY OF S.Typhi Ty21a (pSEC/PA) AND Ty21a(pVDL9-3pA83ec)
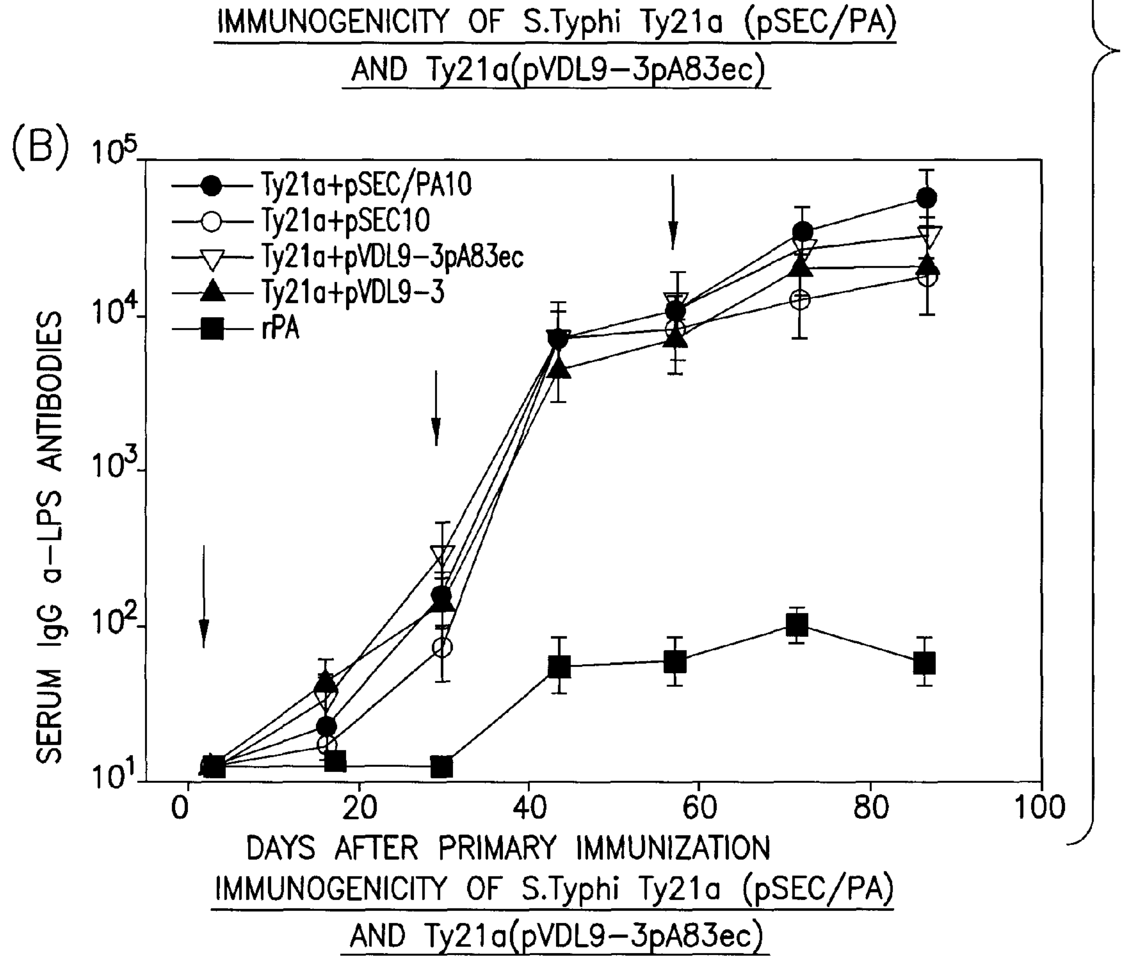
IMMUNOGENICITY OF S.Typhi Ty21a (pSEC/PA) AND Ty21a(pVDL9-3pA83ec)
FIG.21

SURVIVAL RATE OF MICE CHALLENGED WITH B. anthracis AFTER ORAL INOCULATION WITH S. typhimurium EXPRESSING PA PLASMIDS ORAL IMMUNIZATION (INTRA GASTRIC GAVAGE)
A/J MICE (gps 8) RECEIVED 1–5x10$^9$ cfu ON DAYS 0,14 AND 28 AND WERE CHALLENGED WITH A LETHAL SPORE AEROSOL (100 MLD) ON DAY 80

◆ SL3261(pVDL9.3)
■ SL3261 (pVDL9.3PA83ec)
▲ SL3261(pSEC10)
✕ SL3261(pSE10PA)
✶ NAIVE

| |
|---|
| FIG.24A |
| FIG.24B |
| FIG.24C |
| FIG.24D |
| FIG.24E |

CODON OPTIMIZATION RESULT
ORGANISM: SALMONELLA ENTERICA ;
GENE NAME: LF1.PA4
SEQUENCE TYPE: DNA
OPTIMIZATION REGION: 7 - 1278
GC RANGE: 30 - 70
ADDITION 5' SEQUENCE:
ADDITION 3' SEQUENCE:
CUT OFFS:
SECONDARY STRUCTURE STACK CUTOFF: 30
REPEAT CUTOFF: 19
RELATIVE FREQUENCE CUTOFF: 80
5' SPLICE SCORE CUTOFF: 80
GENETIC CODE: 1

RE SITES AND CIS PATTERN:
BAMHI (GGATCC), HINDIII (AAGCTT),
RE CHECK SITES:
SMAI (CCCGGG), ECORV (GATATC)
RE KEEP SITES:

DNA ALIGNMENT (OPTIMIZED REGION). THE CHANGED CODONS ARE INDICATED AS LETTERS OUTLINED IN A BOX:

```
OPTIMIZED 7   GCTGGTGGTCATGGTGATGTTGGTATGCATGTTAAAGAAAAAGAAAAAAACAAAGATGAA
ORIGINAL  7   GCGGGCGGTCATGGTGATGTTGGTATGCATGTTAAAGAGAAAGAGAAAAATAAAGATGAG

OPTIMIZED 67  AACAAACGTAAAGATGAAGAACGTAACAAAACCCAGGAAGAACATCTGAAAGAAATTATG
ORIGINAL  67  AATAAACGTAAAGATGAAGAGCGTAATAAAACCCAGGAAGAGCATCTGAAAGAAATCATG

OPTIMIZED 127 AAACATATTGTTAAAATTGAAGTTAAAGGTGAAGAAGCGGTTAAAAAAGAAGCGGCGGAA
ORIGINAL  127 AAACATATTGTTAAAATTGAAGTTAAAGGCGAGGAAGCCGTTAAAAAAGAGGCAGCCGAA

OPTIMIZED 187 AAACTGCTGGAAAAAGTTCCGTCTGATGTTCTGGAAATGTATAAAGCGATTGGTGGTAAA
ORIGINAL  187 AAACTGCTGGAGAAAGTTCCGAGCGATGTTCTGGAGATGTATAAAGCAATTGGCGGTAAA

OPTIMIZED 247 ATTTATATTGTTGATGGTGATATTACTAAACATATCTCTCTGGAAGCGCTGTCTGAAGAT
ORIGINAL  247 ATCTATATTGTGGATGGTGATATTACCAAACATATTAGCCTGGAAGCACTGAGCGAAGAT
```

FIG.24B

```
OPTIMIZED 307 AAAAAAAAAATCAAAGATATCTATGGTAAAGATGCGCTGCTGCATGAACATTATGTTTAT
ORIGINAL  307 AAGAAGAAAATTAAAGACATCTATGGCAAAGATGCCCTGCTGCATGAACATTATGTTTAT

OPTIMIZED 367 GCGAAAGAAGGTTATGAACCGGTTCTGGTTATTCAGTCTTCTGAAGATTATGTTGAAAAC
ORIGINAL  367 GCAAAAGAAGGCTATGAACCGGTTCTGGTTATCCAGAGCAGCGAAGATTATGTTGAAAAT

OPTIMIZED 427 ACTGAAAAAGCTCTGAACGTTTATTATGAAATTGGTAAAATTCTGTCTCGTGATATTCTG
ORIGINAL  427 ACCGAAAAAGCACTGAACGTTTATTATGAAATTGGTAAAATTCTGAGCCGTGATATTCTG

OPTIMIZED 487 TCTAAAATTAACCAGCCGTATCAGAAATTTCTGGATGTTCTGAACACTATTAAAAACGCG
ORIGINAL  487 AGCAAAATTAATCAGCCGTATCAGAAATTTCTGGATGTTCTGAATACCATTAAAAATGCA

OPTIMIZED 547 TCTGATTCTGATGGTCAGGATCTGCTGTTTACCAACCAGCTGAAAGAACATCCGACCGAT
ORIGINAL  547 AGCGATAGCGATGGCCAGGATCTGCTGTTTACCAATCAGCTGAAAGAACATCCGACCGAC

OPTIMIZED 607 TTTTCTGTTGAATTTCTGGAACAGAACTCTAACGAAGTTCAGGAAGTTTTTGCTAAAGCG
ORIGINAL  607 TTTAGCGTTGAATTTCTGGAACAGAATAGCAATGAGGTTCAGGAAGTTTTTGCGAAAGCC

OPTIMIZED 667 TTTGCGTATTATATTGAACCGCAGCATCGTGATGTTCTGCAGCTGTATGCTCCGGAAGCG
ORIGINAL  667 TTTGCATATTATATCGAGCCGCAGCATCGTGATGTTCTGCAGCTGTATGCACCGGAAGCC
```

FIG.24C

| | | |
|---|---|---|
| OPTIMIZED | 727 | TTTAACTATATGGATAAATTTAACGAACAGGAAATTAACCTGTCTGAACTGGGTACTACT |
| ORIGINAL | 727 | TTTAATTATATGGATAAGTTTAACGAACAGGAAATTAATCTGAGCGAGCTCGGTACCACC |
| OPTIMIZED | 787 | AACATTTATACCGTTCTGGATAAAATTAAACTGAACGCTAAAATGAACATTCTGATTCGT |
| ORIGINAL | 787 | AATATCTATACGGTACTCGACAAGATCAAACTGAACGCGAAAATGAACATTCTGATTCGC |
| OPTIMIZED | 847 | GATAAACGTTTTCATTATGATCGTAACAACATCGCTGTTGGTGCTGATGAATCTGTTGTT |
| ORIGINAL | 847 | GACAAACGTTTCCACTACGATCGTAATAACATCGCTGTTGGCGCTGATGAATCTGTTGTG |
| OPTIMIZED | 907 | AAAGAAGCGCATCGTGAAGTTATTAACTCTTCTACCGAAGGTCTGCTGCTGAACATTGAT |
| ORIGINAL | 907 | AAAGAAGCGCATCGCGAAGTCATCAACTCCAGCACCGAAGGCCTGCTTCTGAACATCGAC |
| OPTIMIZED | 967 | AAAGATATTCGTAAAATTCTGTCTGGTTATATTGTTGAAATTGAAGATACTGAAGGTCTG |
| ORIGINAL | 967 | AAAGACATTCGTAAGATCCTGTCTGGTTACATTGTTGAGATCGAAGACACCGAAGGCCTG |
| OPTIMIZED | 1027 | AAAGAAGTTATCAACGATCGTTATGATATGCTGAACATTTCTTCTCTGCGTCAGGATGGT |
| ORIGINAL | 1027 | AAAGAAGTGATCAATGATCGTTACGACATGCTGAACATCAGCTCTCTGCGTCAAGATGGT |
| OPTIMIZED | 1087 | AAAACCTTTATCGATTTTAAAAAATATAACGATAAACTGCCGCTGTATATCTCTAACCCG |
| ORIGINAL | 1087 | AAGACGTTCATTGACTTCAAGAAATACAACGACAAACTTCCGCTGTATATCTCTAATCCG |

FIG.24D

```
OPTIMIZED 1147 AACTATAAAGTTAACGTTTATGCGGTTACCAAAGAAAACACTATTATTAACCCGTCTGAA
ORIGINAL  1147 AACTACAAAGTGAACGTTTACGCTGTTACCAAAGAGAACACCATCATCAATCCATCTGAG

OPTIMIZED 1207 AACGGTGATACCTCTACTAACGGTATCAAAAAAATCCTGATTTTTTCTAAAAAAGGTTAT
ORIGINAL  1207 AACGGCGATACCTCTACCAACGGTATCAAGAAGATTCTGATCTTCTCCAAGAAAGGTTAC

OPTIMIZED 1267 GAAATTGGTTAA
ORIGINAL  1267 GAGATCGGTTAA
```

```
Protein Alignment (Optimized Region):
Optimized 1   AGGHGDVGMHVKEKEKNKDENKRKDEERNKTQEEHLKEIMKHIVKIEVKGEEAVKKEAAE
Original  1   AGGHGDVGMHVKEKEKNKDENKRKDEERNKTQEEHLKEIMKHIVKIEVKGEEAVKKEAAE

Optimized 61  KLLEKVPSDVLEMYKAIGGKIYIVDGDITKHISLEALSEDKKKIKDIYGKDALLHEHYVY
Original  61  KLLEKVPSDVLEMYKAIGGKIYIVDGDITKHISLEALSEDKKKIKDIYGKDALLHEHYVY

Optimized 121 AKEGYEPVLVIQSSEDYVENTEKALNVYYEIGKILSRDILSKINQPYQKFLDVLNTIKNA
Original  121 AKEGYEPVLVIQSSEDYVENTEKALNVYYEIGKILSRDILSKINQPYQKFLDVLNTIKNA

Optimized 181 SDSDGQDLLFTNQLKEHPTDFSVEFLEQNSNEVQEVFAKAFAYYIEPQHRDVLQLYAPEA
Original  181 SDSDGQDLLFTNQLKEHPTDFSVEFLEQNSNEVQEVFAKAFAYYIEPQHRDVLQLYAPEA

Optimized 241 FNYMDKFNEQEINLSELGTTNIYTVLDKIKLNAKMNILIRDKRFHYDRNNIAVGADESVV
Original  241 FNYMDKFNEQEINLSELGTTNIYTVLDKIKLNAKMNILIRDKRFHYDRNNIAVGADESVV

Optimized 301 KEAHREVINSSTEGLLLNIDKDIRKILSGYIVEIEDTEGLKEVINDRYDMLNISSLRQDG
Original  301 KEAHREVINSSTEGLLLNIDKDIRKILSGYIVEIEDTEGLKEVINDRYDMLNISSLRQDG

Optimized 361 KTFIDFKKYNDKLPLYISNPNYKVNVYAVTKENTIINPSENGDTSTNGIKKILIFSKKGY
Original  361 KTFIDFKKYNDKLPLYISNPNYKVNVYAVTKENTIINPSENGDTSTNGIKKILIFSKKGY

Optimized 421 EIG*
Original  421 EIG*
```

| FIG.26A |
|---|
| FIG.26B |

OPTIMIZED SEQUENCE: LENGTH: 1284, GC%:35.28, MINIMUM FREE ENERGY:-298.25

GGATCCGCTGGTGGTCATGGTGATGTTGGTATGCATGTTAAAGAAAAAGAAAAAAACAAA
GATGAAAACAAACGTAAAGATGAAGAACGTAACAAAACCCAGGAAGAACATCTGAAAGAA
ATTATGAAACATATTGTTAAAATTGAAGTTAAAGGTGAAGAAGCGGTTAAAAAAGAAGCG
GCGGAAAAACTGCTGGAAAAAGTTCCGTCTGATGTTCTGGAAATGTATAAAGCGATTGGT
GGTAAAATTTATATTGTTGATGGTGATATTACTAAACATATCTCTCTGGAAGCGCTGTCT
GAAGATAAAAAAAAAATCAAAGATATCTATGGTAAAGATGCGCTGCTGCATGAACATTAT
GTTTATGCGAAAGAAGGTTATGAACCGGTTCTGGTTATTCAGTCTTCTGAAGATTATGTT
GAAAACACTGAAAAAGCTCTGAACGTTTATTATGAAATTGGTAAAATTCTGTCTCGTGAT
ATTCTGTCTAAAATTAACCAGCCGTATCAGAAATTTCTGGATGTTCTGAACACTATTAAA
AACGCGTCTGATTCTGATGGTCAGGATCTGCTGTTTACCAACCAGCTGAAAGAACATCCG
ACCGATTTTTCTGTTGAATTTCTGGAACAGAACTCTAACGAAGTTCAGGAAGTTTTTGCT
AAAGCGTTTGCGTATTATATTGAACCGCAGCATCGTGATGTTCTGCAGCTGTATGCTCCG
GAAGCGTTTAACTATATGGATAAATTTAACGAACAGGAAATTAACCTGTCTGAACTGGGT
ACTACTAACATTTATACCGTTCTGGATAAAATTAAACTGAACGCTAAAATGAACATTCTG

ATTCGTGATAAACGTTTTCATTATGATCGTAACAACATCGCTGTTGGTGCTGATGAATCT
GTTGTTAAAGAAGCGCATCGTGAAGTTATTAACTCTTCTACCGAAGGTCTGCTGCTGAAC
ATTGATAAAGATATTCGTAAAATTCTGTCTGGTTATATTGTTGAAATTGAAGATACTGAA
GGTCTGAAAGAAGTTATCAACGATCGTTATGATATGCTGAACATTTCTTCTCTGCGTCAG
GATGGTAAAACCTTTATCGATTTTAAAAAATATAACGATAAACTGCCGCTGTATATCTCT
AACCCGAACTATAAAGTTAACGTTTATGCGGTTACCAAAGAAAACACTATTATTAACCCG
TCTGAAAACGGTGATACCTCTACTAACGGTATCAAAAAAATCCTGATTTTTCTAAAAAA
GGTTATGAAATTGGTTAAAAGCTT

Restriction Enzymes:

Fitering Enzymes and CIS Pattern:

BamHI(GGATCC): 1 (1 - GGATCC)

HindIII(AAGCTT): 1 (1279 - AAGCTT)

Checking Enzymes:

SmaI(CCCGGG): 0

EcoRV(GATATC): 1 (322 - GATATC)

Keeping Enzymes:

FIG.26B

IMMUNOGENICITY OF AN LF DOMAIN 1+PA DOMAIN 4 FUSION PROTEIN

1–MW MARKERS
2–PA
3–LF
4–LcrV.PA.LF1 FUSION
5–LF1.PA4 FUSION
6–MW MARKERS
7–PA
8–LF
9–LcrV.PA.LF1 FUSION
10–LF.PA4 FUSION

THE IgG SPECIFIC ANTIBODY RESPONSE OF Balbc MICE IMMUNIZED WITH THE LFD1.PAD4 FUSION PROTEIN IgG SPECIFIC ANTIBODY END POINT TITERS WHERE DETERMINE AT 42 DAYS BY ELISA $LF_n$/V AND V/$LF_n$ FUSION PROTEINS ARE IMMUNOGENIC AND ELICIT ANTI-LF AND ANTI V serum IgG RESPONSES IN BALB/c MICE

FIG.31A

| FIG.31A |
|---|
| FIG.31B |

FIG.31

The LcrV-PA-F1-LFD1 fusion

Native codon usage

ATGAGAGGATCGCATCACCATCACCATCACGGATCCATGATTAGAGCCTACGAACAAAACCCACAAC
ATTTTATTGAGGATCTAGAAAAAGTTAGGGTGGAACAACTTACTGGTCATGGTTCTTCAGTTTTAGA
AGAATTGGTTCAGTTAGTCAAAGATAAAAATATAGATATTTCCATTAAATATGATCCCAGAAAAGAT
TCGGAGGTTTTTGCCAATAGAGTAATTACTGATGATATCGAATTGCTCAAGAAAATCCTAGCTTATT
TTCTACCCGAGGATGCCATTCTTAAAGGCGGTCATTATGACAACCAACTGCAAAATGGCATCAAGCG
AGTAAAAGAGTTCCTTGAATCATCGCCGAATACACAATGGGAATTGCGGGCGTTCATGGCAGTAATG
CATTTCTCTTTAACCGCCGATCGTATCGATGATGATATTTTGAAAGTGATTGTTGATTCAATGAATC
ATCATGGTGATGCCCGTAGCAAGTTGCGTGAAGAATTAGCTGAGCTTACCGCCGAATTAAAGATTTA
TTCAGTTATTCAAGCCGAAATTAATAAGCATCTGTCTAGTAGTGGCACCATAAATATCCATGATAAA
TCCATTAATCTCATGGATAAAAATTTATATGGTTATACAGATGAAGAGATTTTTAAAGCCAGCGCAG
AGTACAAAATTCTCGAGAAAATGCCTCAAACCACCATTCAGGTGGATGGGAGCGAGAAAAAAATAGT
CTCGATAAAGGACTTTCTTGGAAGTGAGAATAAAAGAACCGGGGCGTTGGGTAATCTGAAAAACTCA
TACTCTTATAATAAAGATAATAATGAATTATCTCACTTTGCCACCACCTGCTCGGATAAGTCCAGGC
CGCTCAACGACTTGGTTAGCCAAAAAACAACTCAGCTGTCTGATATTACATCACGTTTTAATTCAGC
TATTGAAGCACTGAACCGTTTCATTCAGAAATATGATTCAGTGATGCAACGTCTGCTAGATGACACG

TCTGGTAAAGCATGCGAGCTCGGTACCAGCGATGTTCTGGAGATGTATAAAGCAATTGGCGGTAAAA
TCTATATTGTGGATGGT GATATTACCAAACATATTAGCCTGGAAGCACTGGATAGCCTGAGCGAA
GAGGAAAAAGAGCTGCTGAATCGTATTCAGGTGGATAGCAGCATCAAATTAAATGCAAAAATGAATA
TTTTAATAAGAGATAAACGTTTTCATTATGATAGAAATAAAAAATATAATGATAAATTACCGTTATA
TATAAGTAATCCCAATTATAAGGTAAATGTATATGCTGCGGCAGATTTAACTGCAAGCACCACTGCA
ACGGCAACTCTTGTTGAACCAGCCCGCATCACTCTTACATATAAGGAAGGCGCTCCAATTACAATTA
TGGCGGGCGGTCATGGTGATGTAGGTATGCACGTAAAAGAGAAAGAGAAAAATAAAGATGAGAATAA
GAGA AAAGATGAA GAA CGA AAT AAA ACA CAG GAA GAG CAT TTA AAG GAA
ATCATG AAA CAC ATT GTA AAA ATA GAA GTA AAA GGG GAG GAA GCT GTTAAA
AAA GAG GCA GCA GAA AAG CTA CTT GAG AAA GTA CCA TCT GATGTT TTA GAG
ATG TAT AAA GCA ATT GGA GGA AAG ATA TAT ATT GTGGAT GGT GAT ATT ACA
AAA CAT ATA TCT TTA GAA GCA TTA TCT GAAGAT AAG AAA AAA ATA AAA GAC
ATT TAT GGG AAA GAT GCT TTA TTA CAT GAA CAT TAT GTA TAT GCA AAA GAA
GGA TAT GAA CCC GTA CTT GTA ATC CAA TCT TCG GAA GAT TAT GTA GAA AAT
ACT GAA AAG GCA CTG AAC GTT TAT TAT GAA ATA GGT AAG ATA TTA TCA AGG
GAT ATT TTA AGT AAA ATT AAT CAA CCA TAT CAG AAA TTT TTA GAT GTA TTA
AAT ACC ATT AAA AAT GCA TCT GAT TCA GAT GGA CAA GAT CTT TTA TTT ACT
AAT CAG CTT AAG GAA CAT CCC ACA GAC TTT TCT GTA GAA TTC TTG GAA CAA
AAT AGC AAT GAG GTA CAA GAA GTA TTT GCG AAA GCT TTT GCA TAT TAT ATC
GAG CCA CAG CAT CGT GAT GTT TTA CAG CTT TAT GCA CCG GAA GCT TTT AAT
TAC ATG GAT AAA TTT AAC GAA CAA GAA ATA AAT CTA TAA
(SEQ ID NO: 24)

FUSION PROTEIN AMINO ACID SEQUENCE WHICH INCLUDES AN N TERMINAL 6 HIS TAG FOR PROTEIN PURIFICATION.

Met R G S H H H H H H G S Met I R A Y E Q N P Q H F I E D L E K V R V E Q L T G
H G S S V L E E L V Q L V K D K N I D I S I K Y D P R K D S E V F A N R V I T D
D I E L L K K I L A Y F L P E D A I L K G G H Y D N Q L Q N G I K R V K E F L E
S S P N T Q W E L R A F Met A V Met H F S L T A D R I D D D I L K V I V D S Met
N H H G D A R S K L R E E L A E L T A E L K I Y S V I Q A E I N K H L S S S G T
I N I H D K S I N L Met D K N L Y G Y T D E E I F K A S A E Y K I L E K Met P Q
T T I Q V D G S E K K I V S I K D F L G S E N K R T G A L G N L K N S Y S Y N K
D N N E L S H F A T T C S D K S R P L N D L V S Q K T T Q L S D I T S R F N S A
I E A L N R F I Q K Y D S V Met Q R L L D D T S G K A C E L G T S D V L E Met Y
K A I G G K I Y I V D G D I T K H I S L E A L D S L S E E E K E L L N R I Q V D
S S I K L N A K Met N I L I R D K R F H Y D R N K K Y N D K L P L Y I S N P N Y
K V N V Y A A A D L T A S T T A T A T L V E P A R I T L T Y K E G A P I T I Met
A G G H G D V G Met H V K E K E K N K D E N K R K D E E R N K T Q E E H L K E I
Met K H I V K I E V K G E E A V K K E A A E K L L E K V P S D V L E Met Y K A I
G G K I Y I V D G D I T K H I S L E A L S E D K K K I K D I Y G K D A L L H E H
Y V Y A K E G Y E P V L V I Q S S E D Y V E N T E K A L N V Y Y E I G K I L S R
D I L S K I N Q P Y Q K F L D V L N T I K N A S D S D G Q D L L F T N Q L K E H
P T D F S V E F L E Q N S N E V Q E V F A K A F A Y Y I E P Q H R D V L Q L Y A
P E A F N Y Met D K F N E Q E I N L Stop (SEQ ID NO: 25)

IMMUNOGENICITY OF LcrV-PA-F1-LFD1 FUSION PROTEIN

FUSION PROTEIN WAS PROBED WITH ANTIGEN SPECIFIC IMMUNE SERUM 1 2 3 4 5 6

1. PA ANTISERA
2. MW MARKER
3. LF ANTISERA
4. MW MARKER
5. LcrV ANTISERA
6. MW MARKER

THE IgG SPECIFIC ANTIBODY RESPONSE OF Balbc MICE
IMMUNIZED WITH THE FUSION PROTEIN IgG SPECIFIC ANTIBODY END POINT TITERS WHERE DETERMINE
AT 42 DAYS BY ELISA IgG SPECIFIC ANTIBODY RESPONSE

- LFD1
- PA FULL LENGTH
- LcrV.PA.F1.LFD1
- PBS

*SALMONELLA* BASED ORAL VACCINES FOR ANTHRAX

RELATED APPLICATION DATA

This application is filed under the provisions of 35 USC a US national phase filed under the provisions of 35 USC §371 of International Application No. PCT/US06/44037 filed Nov. 14, 2006, which in turn claims priority of U.S. Provisional Patent Application No. 60/736,457 filed Nov. 14, 2005. The disclosures of such international application and U.S. priority application are hereby incorporated herein by reference in their respective entireties, for all purposes.

GOVERNMENTAL INTERESTS

The invention was made with government support under Grant No. U19A1058578-01, awarded by the National Institutes of Health's (NIH) National Institute of Allergy and Infectious Diseases (NIAID). The United States government has certain rights in this invention.

FIELD OF THE INVENTION

The invention relates generally to *Salmonella* based oral vaccines for the treatment or prevention of anthrax, alone or in addition to another pathogen, and more specifically to live oral vaccines for inducing an immune response in a subject.

BACKGROUND OF THE INVENTION

Anthrax is an infection caused by the spore-forming bacterium *Bacillus anthracis*. Anthrax may enter the body and cause infection by means of inhalation, ingestion or subcutaneous exposure. While animals are most at risk for anthrax exposure, humans working with such animals may also be at risk. Additionally, recent heightened awareness of the possibility of bioterrorism has raised concerns about the use of *B. anthracis* or related strains, both newly emerging or genetically engineered, as bio-weapons.

There is therefore a need to develop vaccines for widespread use in the event of a bioterrorist attack, in order to minimize the exposure of a population to the bacteria. In particular, the ability to confer protection following oral dosing is particularly attractive in the context of a bioterrorism event as it would greatly simplify the process of mass vaccinations. Additionally, such a vaccine may be used in situations where a population may be at high risk of exposure to the bacteria, whether through bioterroristic activity or natural exposure, due to proximity to infected animals or to the spores.

The infective process of anthrax occurs when the spores are taken up by the body, through inhalation, ingestion or subcutaneous exposure. The spores become active toxic bacteria and express anthrax toxin, which will ultimately halt the host's immune response and cause cell death. Anthrax toxin has three components: anthrax protective antigen (PA), anthrax edema factor (EF) and anthrax lethal factor (LF). PA binds an anthrax toxin receptor (ATR) on the surface of the host cell. The PA is then cleaved by a host protease, activating the PA, which then binds to other active PAs to form a heptamer. The heptamer then binds EF or LF and the entire complex is drawn into the cell via endocytosis, forming an endosome within the host cell. The EF or LF is ejected from the endosome, into the cytosol of the cell. Once in the cytosol, LF and EF exert their enzymatic activities, interrupt cell signaling and damage the cells. EF ultimately causes edema and LF ultimately causes cell lysis.

The current FDA approved vaccine is a sterile product made from an avirulent, nonencapsulated strain of *B. anthracis*. The vaccine was approved by the FDA in 1970 and is generally administered to those considered at high risk, especially those in the United States who work in close contact with potentially infected animals or animal products, such as hides, hairs or bones, e.g. veterinarians and laboratory workers. The vaccine, BioThrax® (Anthrax Vaccine Adsorbed or "AVA"), is manufactured by one company, Emergent Biosolutions of Gaithersburg, Md. (formerly Bioport Corporation, Lansing, Mich.). Possible reactions to the vaccine include local reactions, and very rare systemic reactions, causing flu-like symptoms. This vaccine requires six vaccinations over eighteen months (at 0, 2 and 4 weeks and at 6, 12 and 18 months), followed by yearly boosters; see BioThrax® AVA, prescription information, dosage instructions.

Various additional vaccines have been developed against anthrax. PA, as a potent immunogen is generally the target for such vaccines. PA is non-toxic and has been shown in numerous animal studies to be capable of stimulating the production of protective antibodies when given as a vaccine. It is thought that these antibodies protect by inhibiting the binding of PA to the host cell and/or binding to EF and/or LF. However, current vaccines suffer from problems such as poor levels of expression and the need for multiple dosing.

Thus, while certain prevention and treatment approaches may prove useful in modulating the effects of anthrax toxin, there remains a need for an effective and safe vaccine that would effectively produce immunity to anthrax with fewer doses.

Various vaccines have been discussed that target the natural mechanism of PA, LF and/or EF. For example, U.S. Pat. No. 5,591,631 and U.S. Pat. No. 5,677,274 describe fusion proteins including domains of PA and/or LF.

In another approach, U.S. Patent Application No. 2004/0166120 has described a composition which contains PA and a truncated, non-functional *B. anthracis* LFn for eliciting a *B. anthracis* immune response.

Additionally, U.S. Patent Application No. 2003/0003109 discusses vaccines that administer a polynucleotide with a coding sequence for a mutated LF protein or an immunogenic fragment of an LF protein and a polynucleotide with a coding sequence for PA or an immunogenic fragment of PA to a subject.

U.S. Patent Application No. 2005/0063986 discusses recombinant DNA constructs containing wild type or mutant type PA, LF or EF.

Additional approaches have focused on live vaccines as expression systems for PA, LF or EF, but have not been able to develop these vaccines for human use. Specific attempts focused on use of live *Salmonella* (Coulson, et al. *Vaccine*, vol. 12, No. 15, 1395-1401 (1994); Garmory, et al. *Infect. Immun.*, 71(7): 3831-6 (2003)) and *B. anthracis* (Aloni-Grinstein, et al. *Infect. Immun.*, 73(7): 4043-53 (2005)) have met with limited success, but have not been developed for human use. Additional work has focused on the possibilities of development of live vaccines (U.S. Application No. 2004/0197343), but have not identified a specific vaccine for use in humans utilizing a live virus containing genetic material from *B. anthracis*.

The utility of attenuated strains of *Salmonella* as a live oral vaccine for typhoid has resulted in the development of a licensed, FDA approved vaccine. There is considerable interest in building on this approach to develop *Salmonella* based vaccines capable of conferring protection against a range of infectious agents and cancer. In particular, development of a live oral anthrax vaccine would be desirable. Additionally, development of a live oral anthrax vaccine with additional activity against one or more additional pathogens would be desirable. However, attempts to use these methods with regard to anthrax have not succeeded to date. Investigations of the use of a live vaccine for expression and delivery of PA, LF and/or EF, have met with limited success, suffering the problem of low levels of expression. Live vaccines evoke the most effective immunity and are the least expensive to produce but in practice are very difficult to make. Additionally, there is a concern that such vaccines would not be effective against genetically modified strains of *B. anthracis* or against other strains such as *Bacillus cereus* G9241, which has acquired the *B. anthracis* toxins and causes an anthrax-like infection in humans.

Therefore, there remains a need in the art for development of a vaccine using specific antigens from anthrax that are expressed in high quantity and do not require excessive dosing. A live vaccine would be preferred. Such a vaccine would preferably be effective against *B. anthracis*, genetically modified *B. anthracis*, anthrax-like strains, and/or additional pathogens, such as plague. In particular, an oral vaccine would be desirable for ease of administration. Such a vaccine is desirable for use in humans.

SUMMARY OF THE INVENTION

The present invention relates to live oral vaccines for the prevention of infection by anthrax, genetically modified *B. anthracis* or anthrax-like strains. The present invention also relates to live oral vaccines for the prevention of infection by anthrax, genetically modified *B. anthracis* or anthrax-like strains, and additional pathogen(s), e.g., plague.

Thus in one aspect the invention provides a vaccine for the prevention of anthrax comprising a live, attenuated *Salmonella*, where the *Salmonella* comprises at least one nucleotide sequence encoding PA and at least one nucleotide sequence encoding a non lethal mutated form of LF.

In another embodiment, the invention provides a vaccine for the prevention of anthrax, as above, but where the live, attenuated *Salmonella* comprises at least one nucleotide sequence encoding at least a fragment of PA and at least one nucleotide sequence encoding at least a fragment of a non lethal mutated form of LF.

In a preferred embodiment, the invention provides a vaccine for the prevention of anthrax, as above, but where the live, attenuated *Salmonella* comprises at least one nucleotide sequence encoding at least a fragment of PA and at least one nucleotide sequence encoding at least a fragment of a non lethal mutated form of LF, wherein the fragments of the PA and LF include at least one active epitope.

In still another embodiment the invention provides a method for inducing a cellular immune response in a subject comprising administering a live, attenuated *Salmonella* comprising at least one nucleotide sequence encoding PA and at least one nucleotide sequence encoding a non lethal mutated form of LF.

The invention also provides a vaccine for the prevention of anthrax, comprising a live, attenuated *Salmonella*, where the *Salmonella* comprises at least one nucleotide sequence encoding PA or a fragment thereof and at least one nucleotide sequence encoding a non lethal mutated form of LF or a fragment thereof.

In yet another embodiment, the invention provides a vaccine for the prevention of anthrax, comprising a live, attenuated *Salmonella*, where the *Salmonella* comprises at least one nucleotide sequence encoding PA or a fragment thereof and at least one nucleotide sequence encoding a non lethal mutated form of LF or a fragment thereof, wherein the wherein the PA or fragment thereof and LF or fragment thereof include at least one active epitope.

In still a further embodiment, the invention provides a vaccine for the prevention of anthrax, comprising a live, attenuated *Salmonella* comprising at least one nucleotide sequence encoding anthrax protective antigen (PA) Domain 4 or a fragment thereof.

In yet another embodiment, the invention provides a vaccine for the prevention of anthrax, comprising a live, attenuated *Salmonella* comprising at least one nucleotide sequence encoding a non lethal mutated form of anthrax lethal factor (LF) Domain 1 or a fragment thereof.

In still another embodiment, the invention provides a vaccine for the prevention of anthrax, comprising a live, attenuated *Salmonella* comprising at least one nucleotide sequence encoding a non lethal mutated form of anthrax lethal factor (LF) or a fragment thereof and at least one nucleotide sequence encoding an antigen of an additional pathogen, or fragment thereof. In one aspect the sequence encoding the LF and the sequence encoding the antigen of the additional pathogen are fused. In a further aspect the LF or fragment thereof is Domain 1. In still another aspect, the additional pathogen is plague.

In still another embodiment, the invention provides a method of stimulating antibody response in a subject through administration of a live, attenuated *Salmonella*, where the *Salmonella* comprises at least one nucleotide sequence encoding PA or a fragment thereof and at least one nucleotide sequence encoding a non lethal mutated form of LF or a fragment thereof, wherein the LF contains at least one active epitope, wherein at least one antibody to the epitope is stimulated.

In a still further embodiment, the invention provides a method of stimulating antibody response in a subject, comprising administration of a live, attenuated *Salmonella* comprising at least one nucleotide sequence encoding a non lethal mutated form of anthrax lethal factor (LF) or a fragment thereof, fused to a nucleotide sequence encoding an antigen of an additional pathogen, or fragment thereof, wherein the LF contains at least one active epitope, and wherein at least one antibody to the epitope is stimulated and at least one antibody to the antigen of the additional pathogen is generated. In another aspect the antibody response to the LF and the antigen of an additional pathogen confers immunity to the subject against a subsequent exposure to anthrax and the additional pathogen.

These and other aspects of the present invention are described with respect to particular preferred embodiments and will be apparent to those skilled in the art from the teachings herein.

and infected individuals who had been treated for cutaneous anthrax. Samples were analyzed for the presence of antibodies to PA, LF and EF by ELISA.

Figure 3:
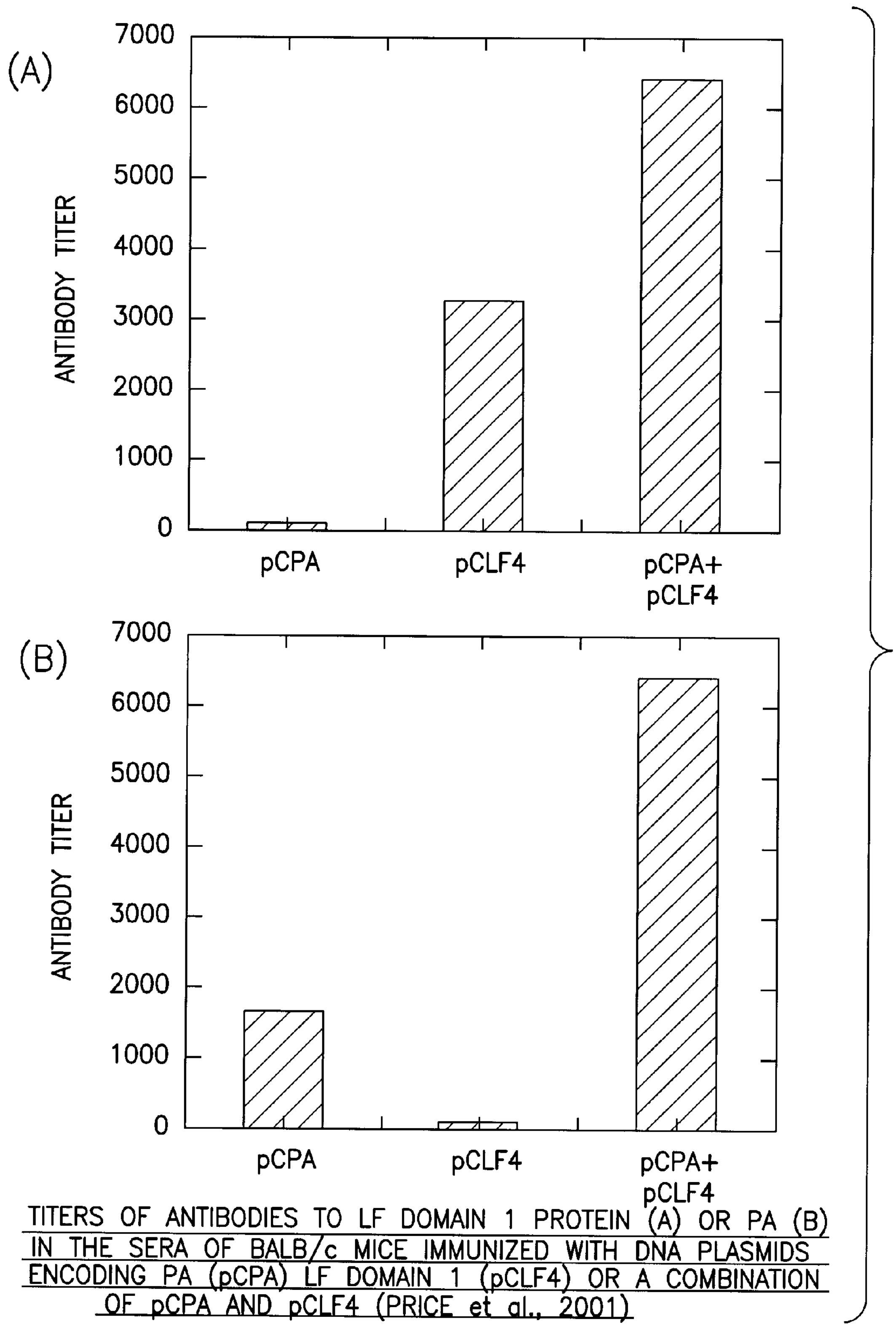

FIG. 3 is two graphs, A and B, showing titers of antibodies to LF Domain 1 protein (A) or PA (B) in the sera of BALB/c mice immunized with DNA plasmids encoding PA (pCPA), LF Domain 1 (pCLF4) or a combination of pCPA and pCLF4.

Figure 4:
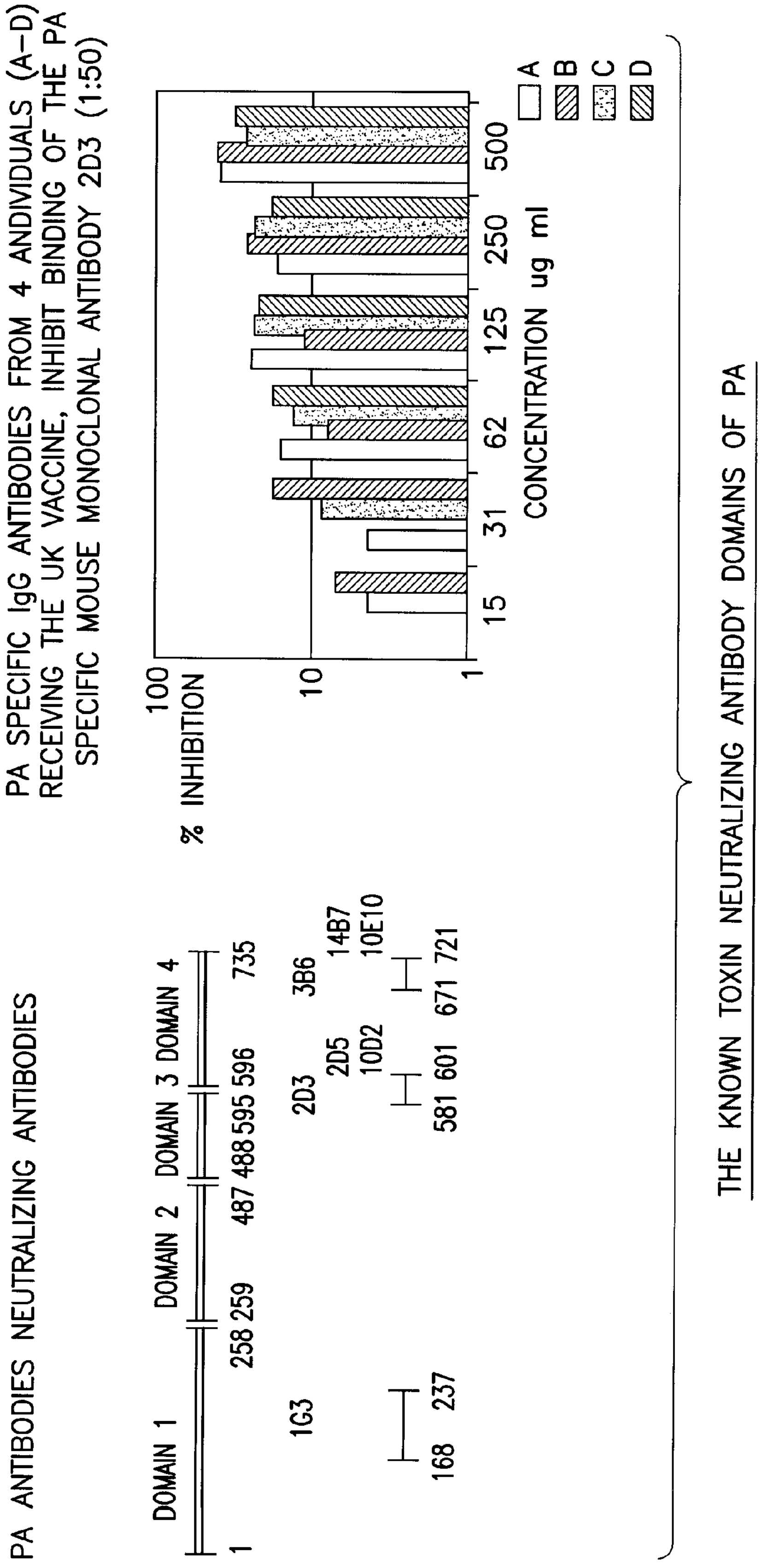

FIG. 4 is an illustration showing the known toxin neutralizing antibody domains of PA.

Figure 5:
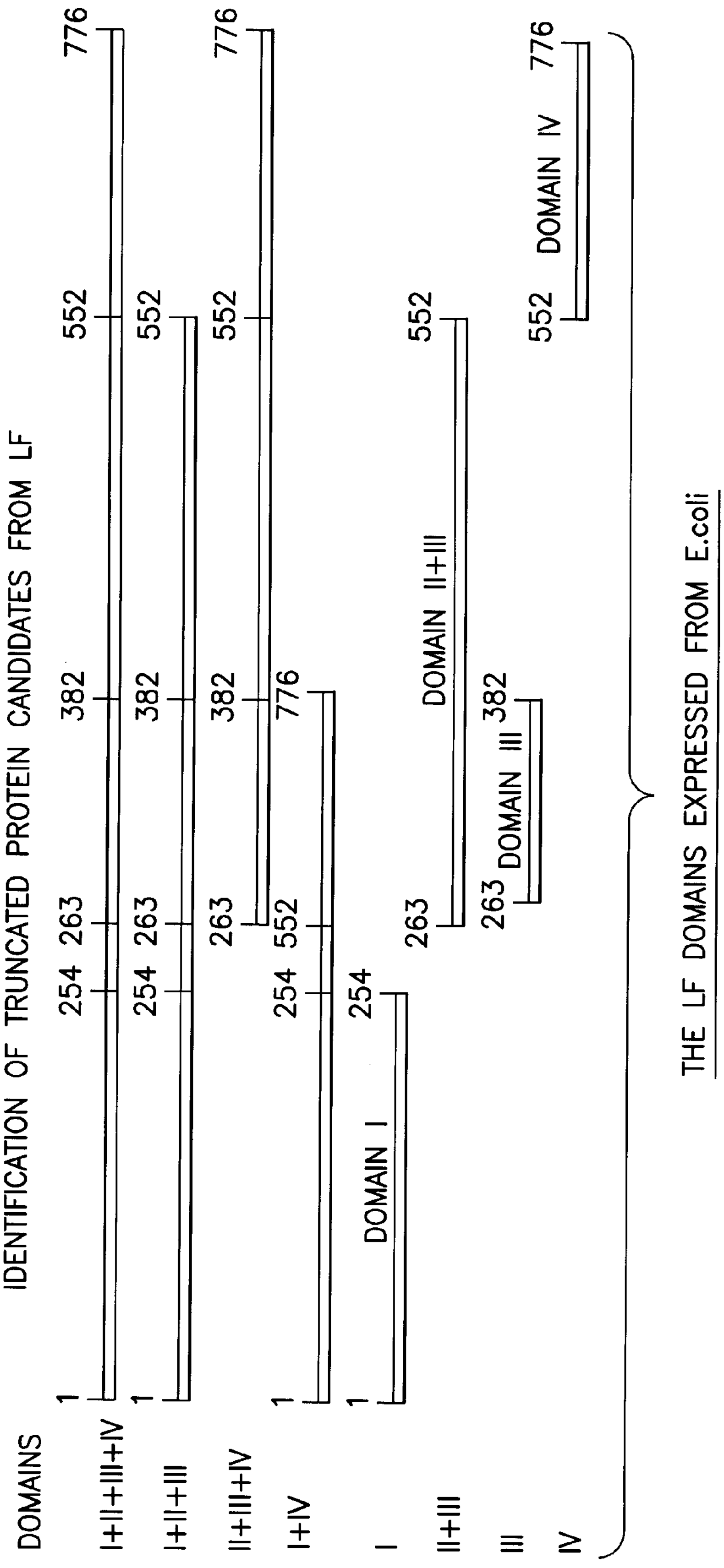

FIG. 5 is an illustration showing the LF domains expressed from *E. coli.*

Figure 6:
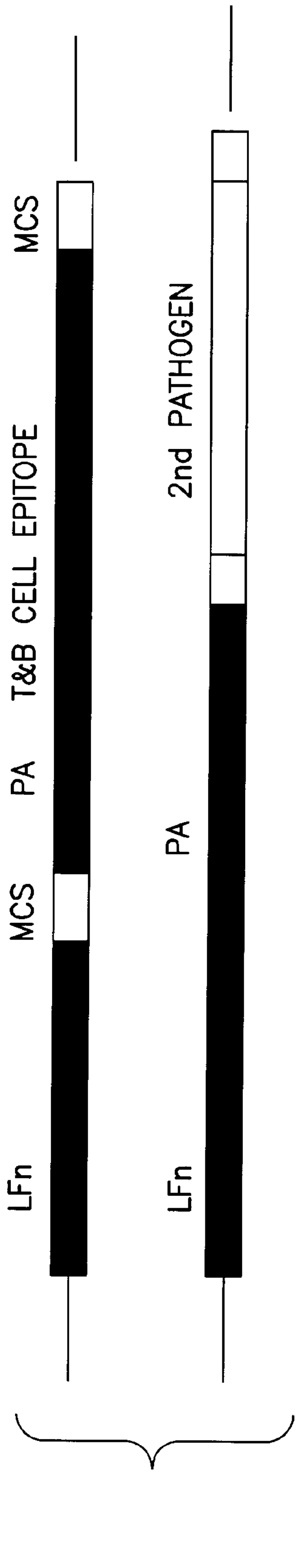

FIG. 6 is an illustration showing a LFn epitope delivery construct.

Figure 7:
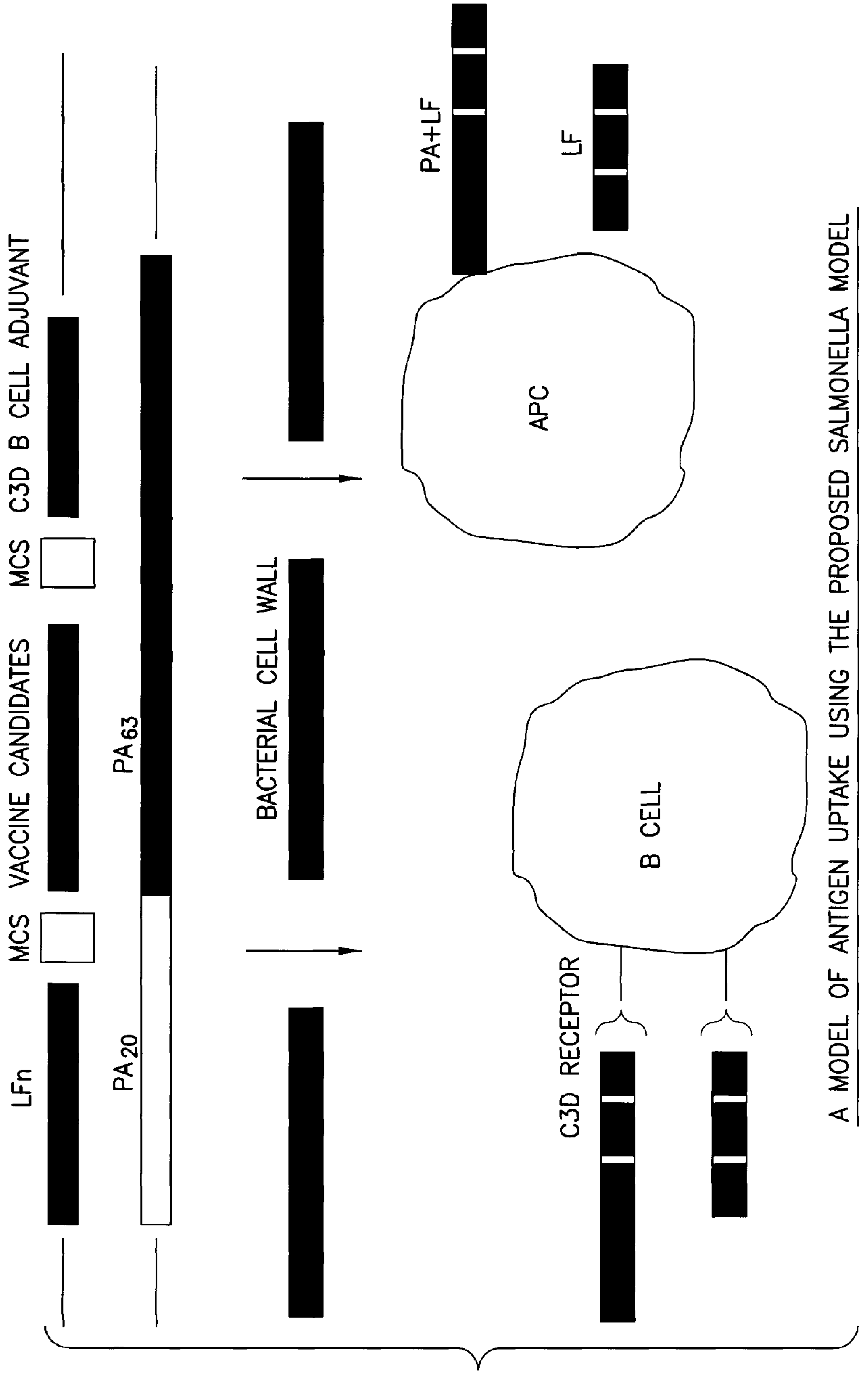

FIG. 7 is a model of antigen uptake utilizing a *Salmonella* model.

Figure 8:
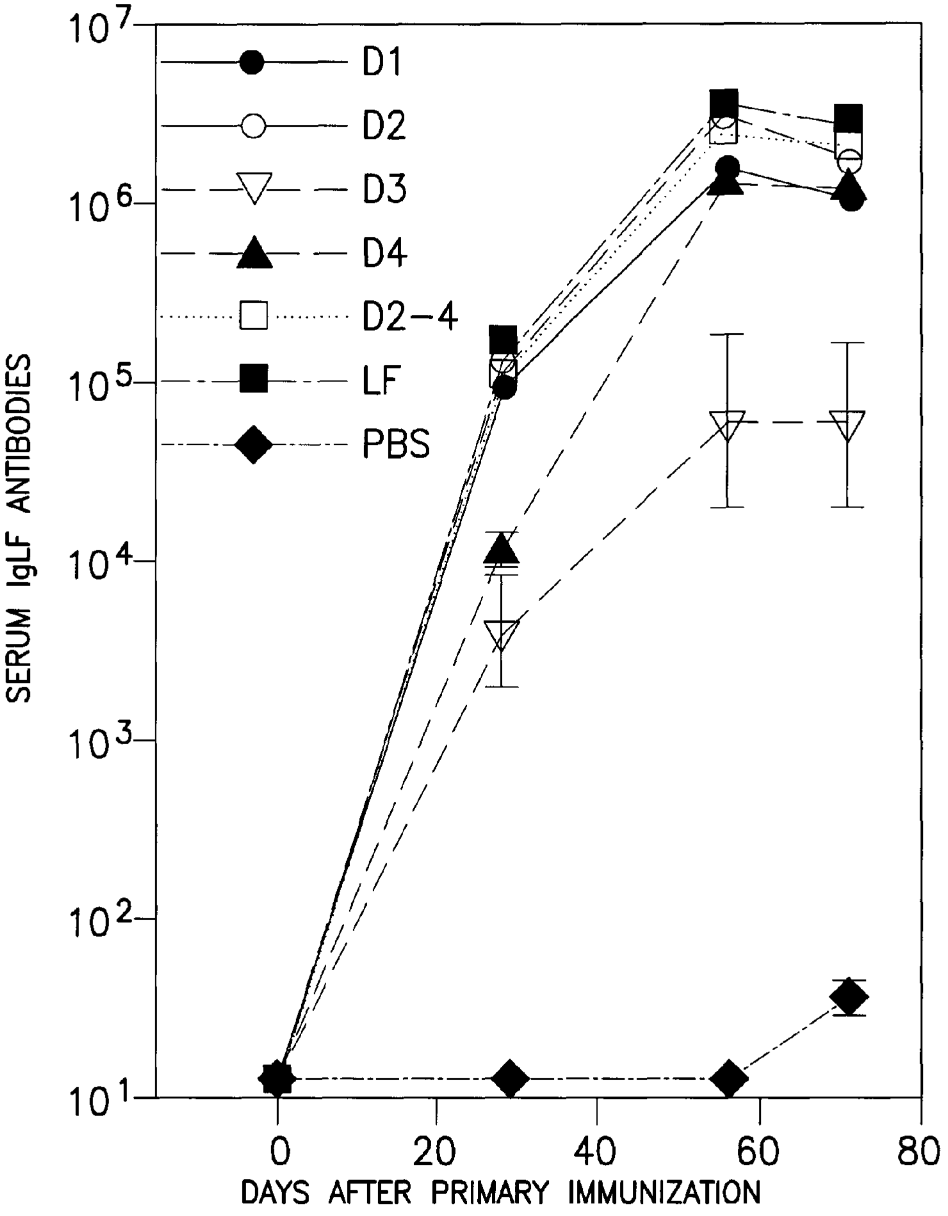

FIG. 8 is a graph of the immunogenicity of the various LF domains expressed from *E. coli* and purified.

Figure 9:
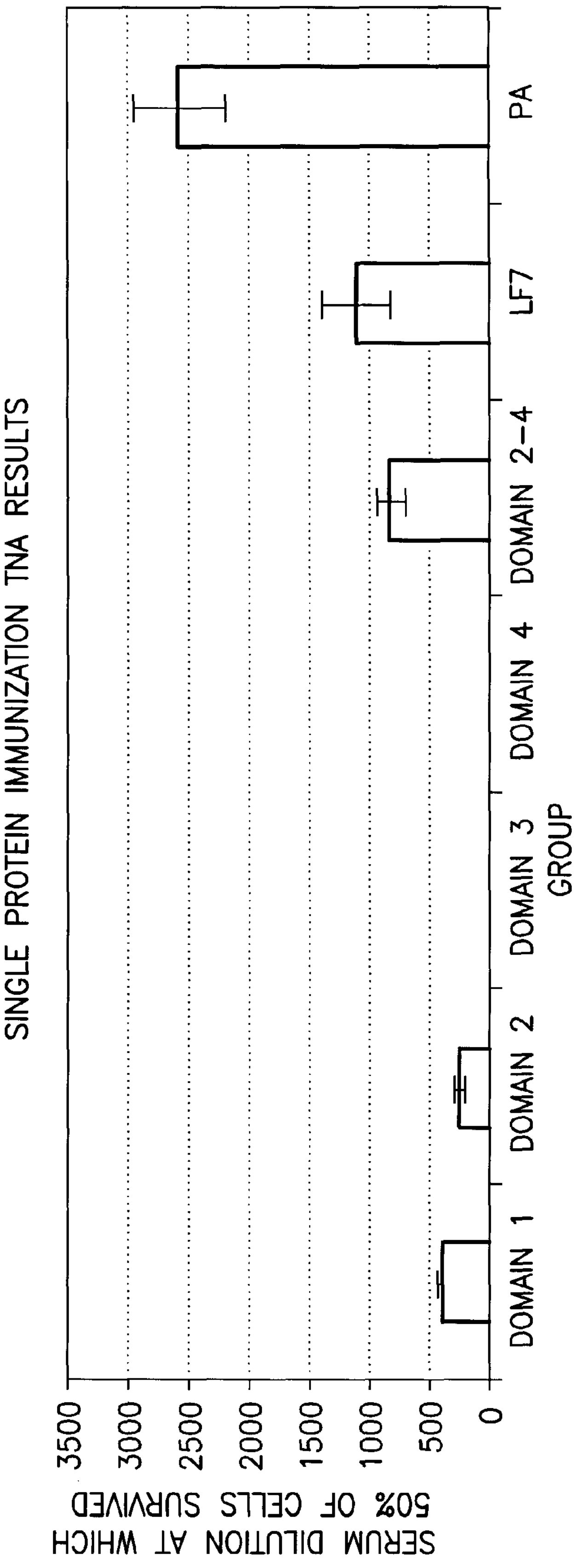

FIG. 9 is a graph of the results of an assay performed in mice of the ability of antibodies specific to individual LF domains to neutralize anthrax toxin activity. The mice were immunized with biologically inactive LF, an LF domain or domains or PA, as set forth in Example 2.

Figure 10:
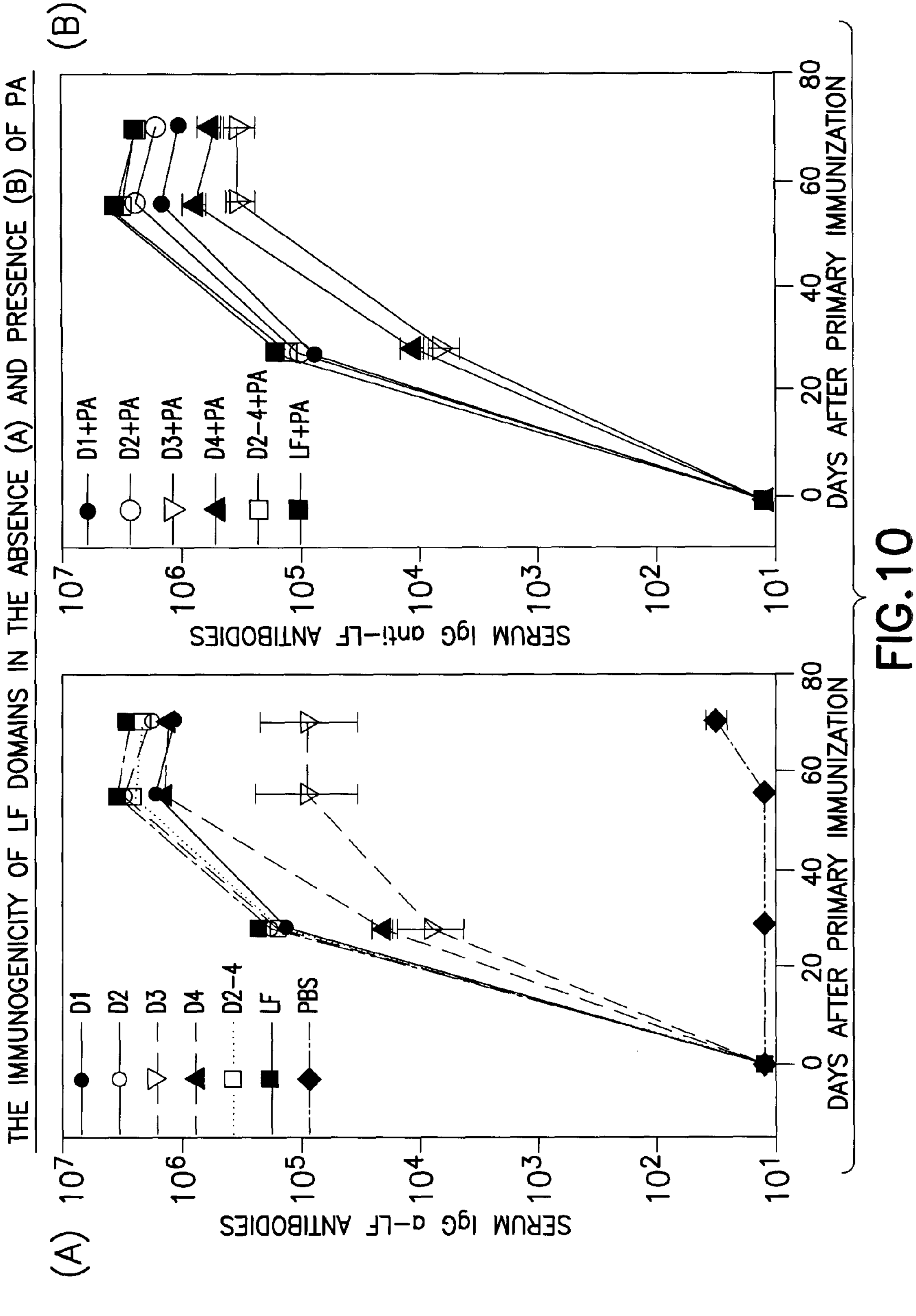

FIG. 10 is two graphs of the immunogenicity in mice of LF domains in the absence (A) and presence (B) of PA, as determined by the process set forth in Example 3.

Figure 11:
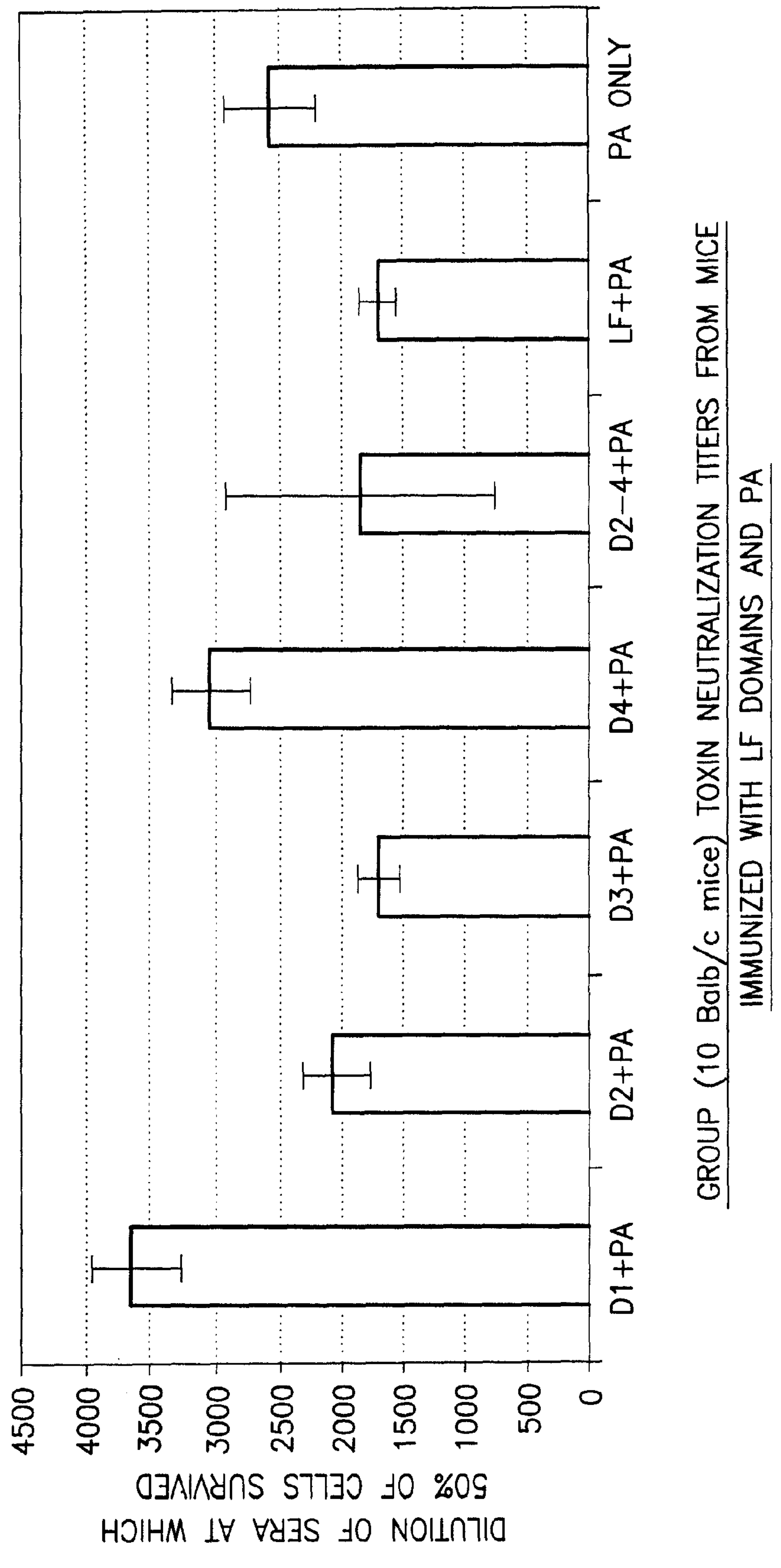

FIG. 11 is a bar graph of the titer results of a toxin neutralization titer from mice immunized with LF domains and PA, as set forth in Example 3.

Figure 12:
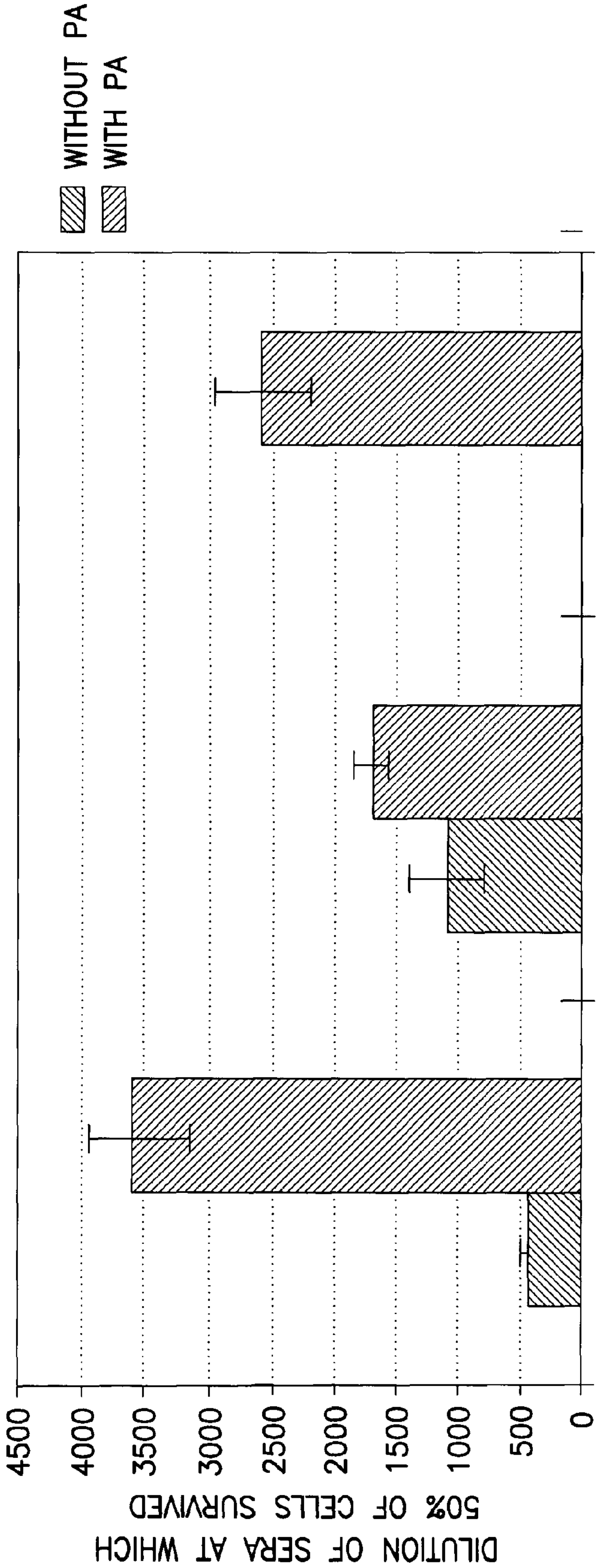

FIG. 12 is a bar graph summarizing the titer results for LF Domain 1 and full length biologically inactive LF in the presence of PA, as determined by Example 3.

Figure 13:
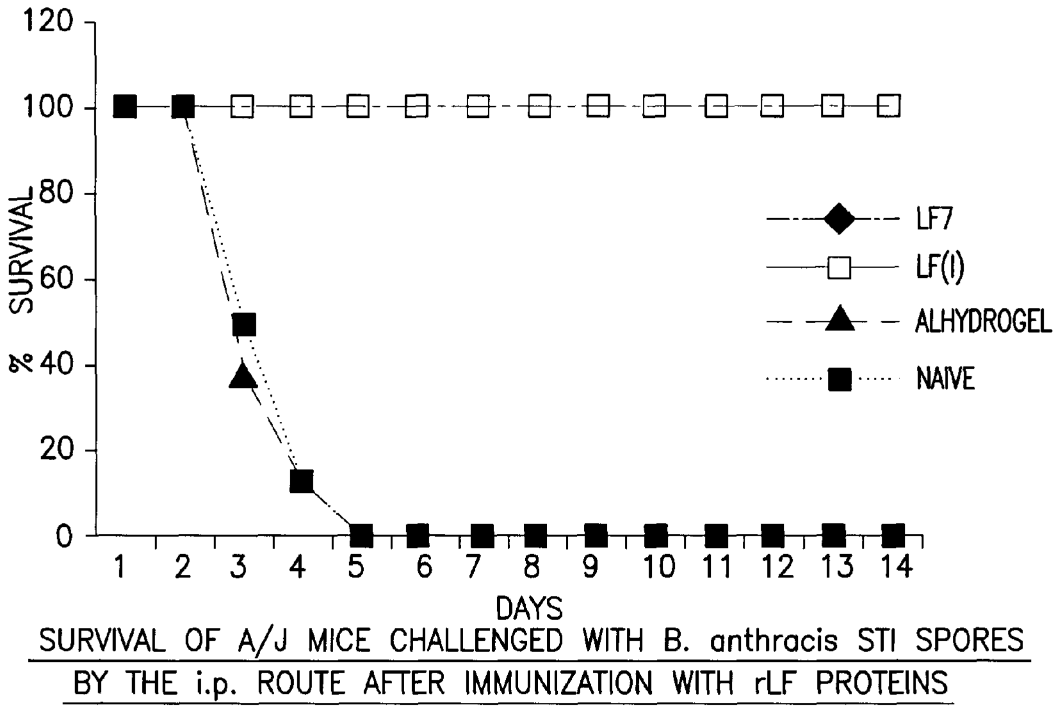

FIG. 13 is a graph showing the percent survival of mice immunized by rLF protein and subsequently challenged with *B. anthracis* STI spores by the i.p. route, as set forth in Example 4.

Figure 14:
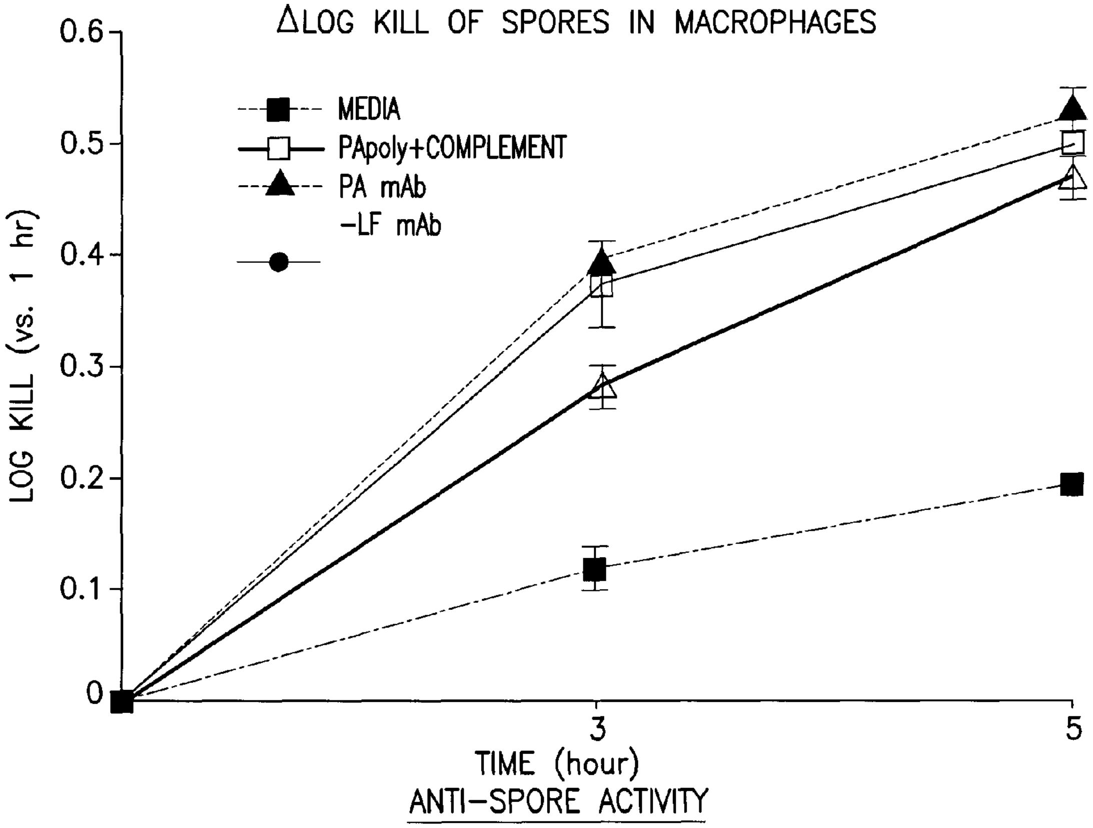

FIG. 14 is a graph showing anti-spore activity over time by macrophages and macrophages facilitated by antibodies.

Figure 15:
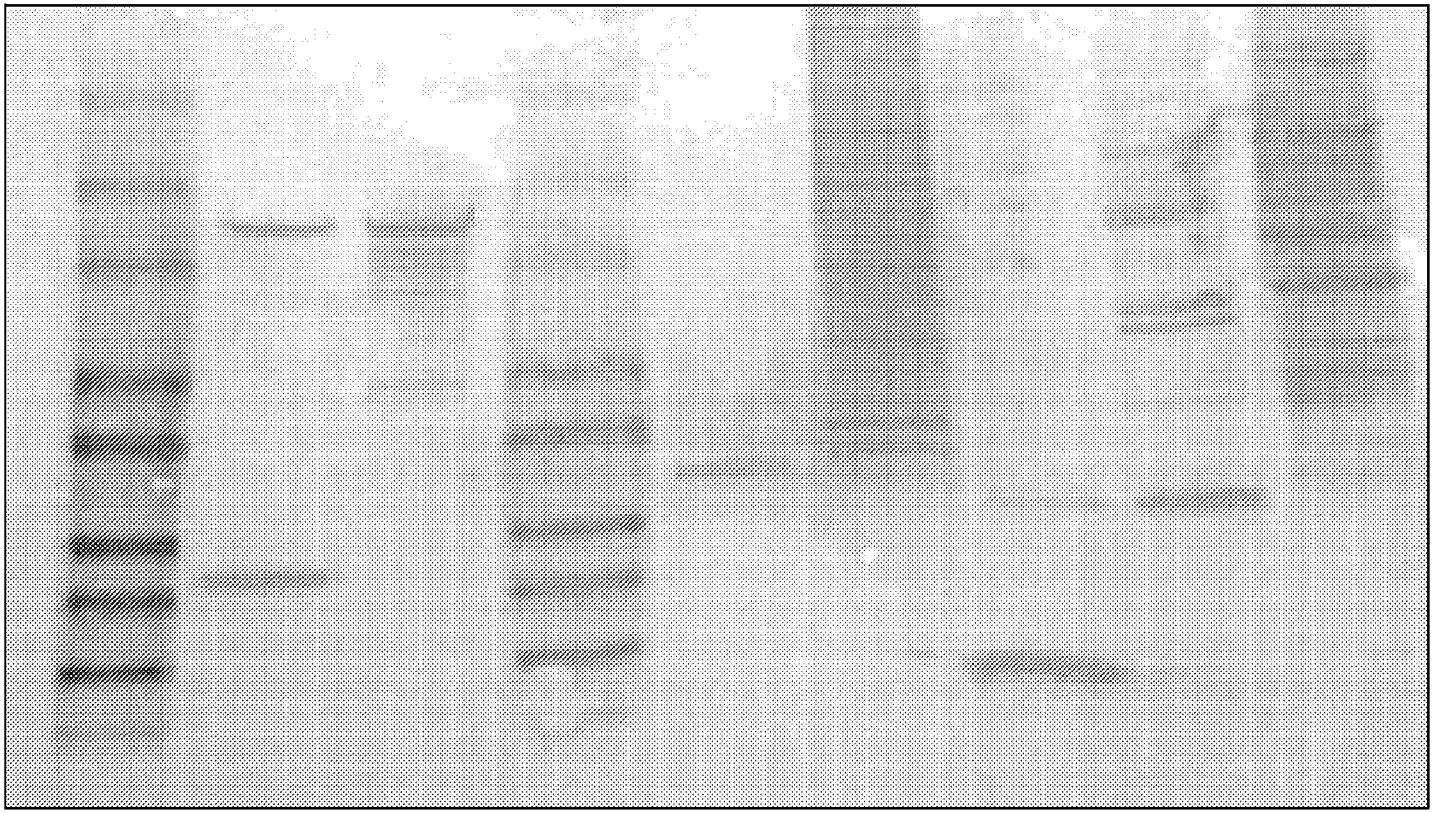

FIG. 15 is a Western blot of PA and LF domains with serum from a rabbit exposed to *B. cereus* G9241, where 1 is the MW ladder, 2 is PA, 3 is LF, 4 is MW ladder, 5 is LF Domain 1, 6 is LF Domain 2, 7 is LF Domain 3, 8 is LF Domain 4 and 9 is LF Domains 2-4.

FIG. 16 is a comparison of the gene sequence of *B. anthracis* lethal factor (LF) as filed with Genebank (accession number M29081) (SEQ ID NO: 1) and the gene sequence of biologically inactive LF as used herein (SEQ ID NO: 2), where the only significant change is replacement of amino acid 687 glutamic acid (GAA) with cysteine (TGC). The codon of the change is shown in lower case (tgc).

FIG. 17 is the optimized sequence of biologically inactive *B. anthracis* LF (SEQ ID NO: 3).

FIG. 18 is a comparison of the protein sequences of the translated gene sequences of *B. anthracis* LF (SEQ ID NO: 4) and biologically inactive LF set forth in FIG. 16 (SEQ ID NO: 5).

Figure 19:
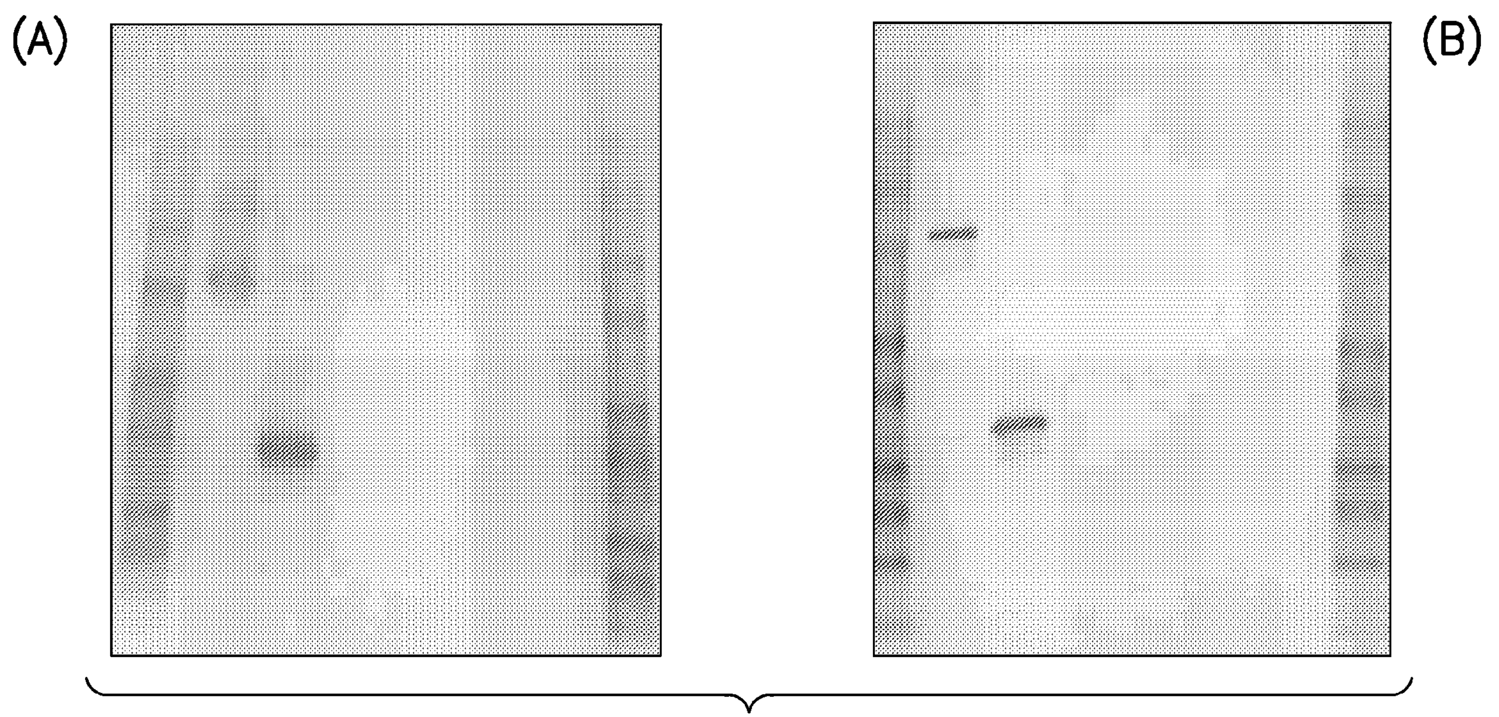

FIG. 19 shows two Western blots of LF Domain recognition of IQNLF (SEQ ID NO: 26), where a) is a native blot and b) is an SDS-denaturing blot.

Figure 20:
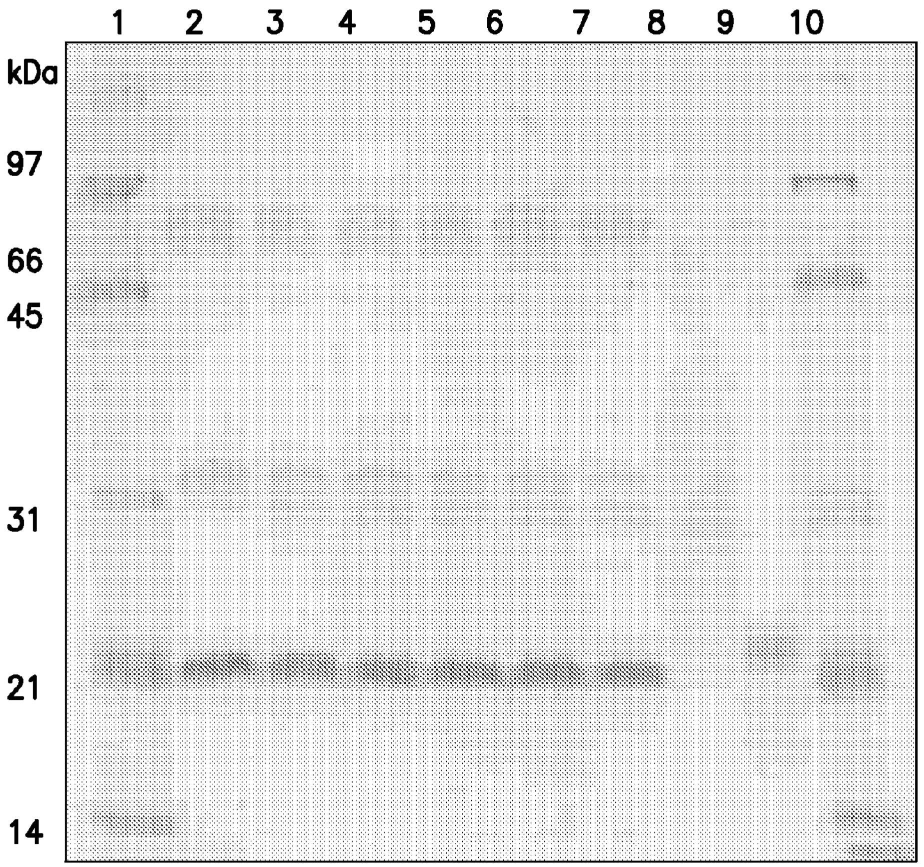

FIG. 20 shows a Western blot of LF Domain 1 expression in *S. enterica* serovar Typhimurium SL3261, where lane 1 is Bio-Rad low range standards, lane 2 is SL3261/pSEC10-LFnN#26, lane 3 is SL3261/pSEC10-LFnN#29, lane 4 is SL3261/pSEC10-LFnN#31, lane 5 is SL3261/pSEC10-LFoN#26, lane 6 is SL3261/pSEC10-LFoN#27, lane 7 is SL3261/pSEC10-LFoN#33), lane 8 is Recombinant LF dom1, lane 9 is *E. coli* TOP10/pSEC10, and lane 10 is Bio-Rad low range standards. Probed with mouse monoclonal antibody to LF Domain 1.

FIG. 21 is a comparison of the immunogenicity of *S. Typhi* Ty21a (PSECIPA) and Ty21a (pVDL9-3pA83ec), as determined by a) presence of IgG a-PA antibodies and b) presence of IgG a-LPS antibodies.

Figure 22:
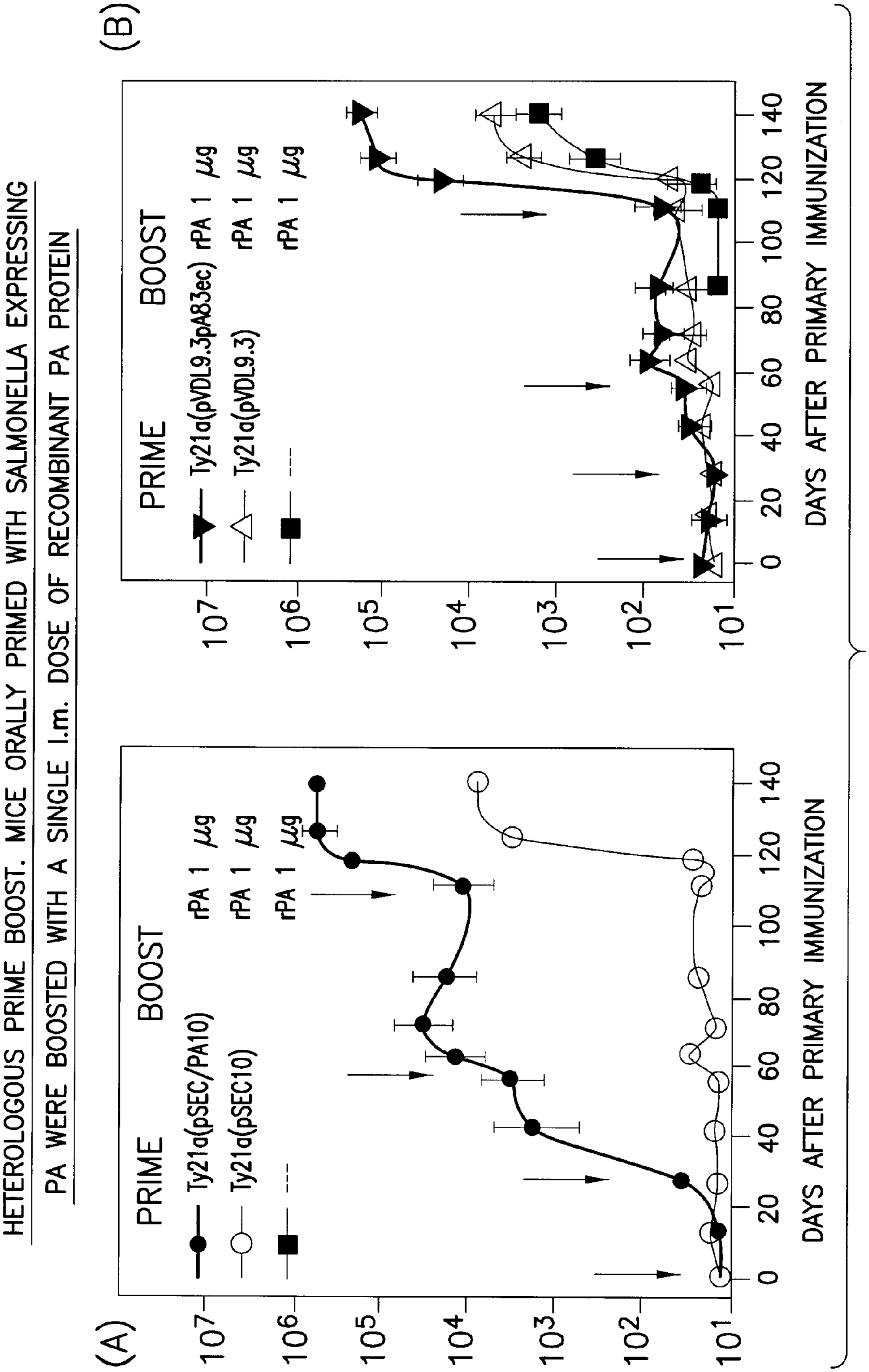

FIG. 22 shows the results of a heterologous prime boost in mice immunized with *S. Typhi* Ty21a expressing PA, where the boost was a single dose of 1 ug recombinant PA. Naïve mice boosted with 1 ug recombinant PA were provided as a control.

Figure 23:
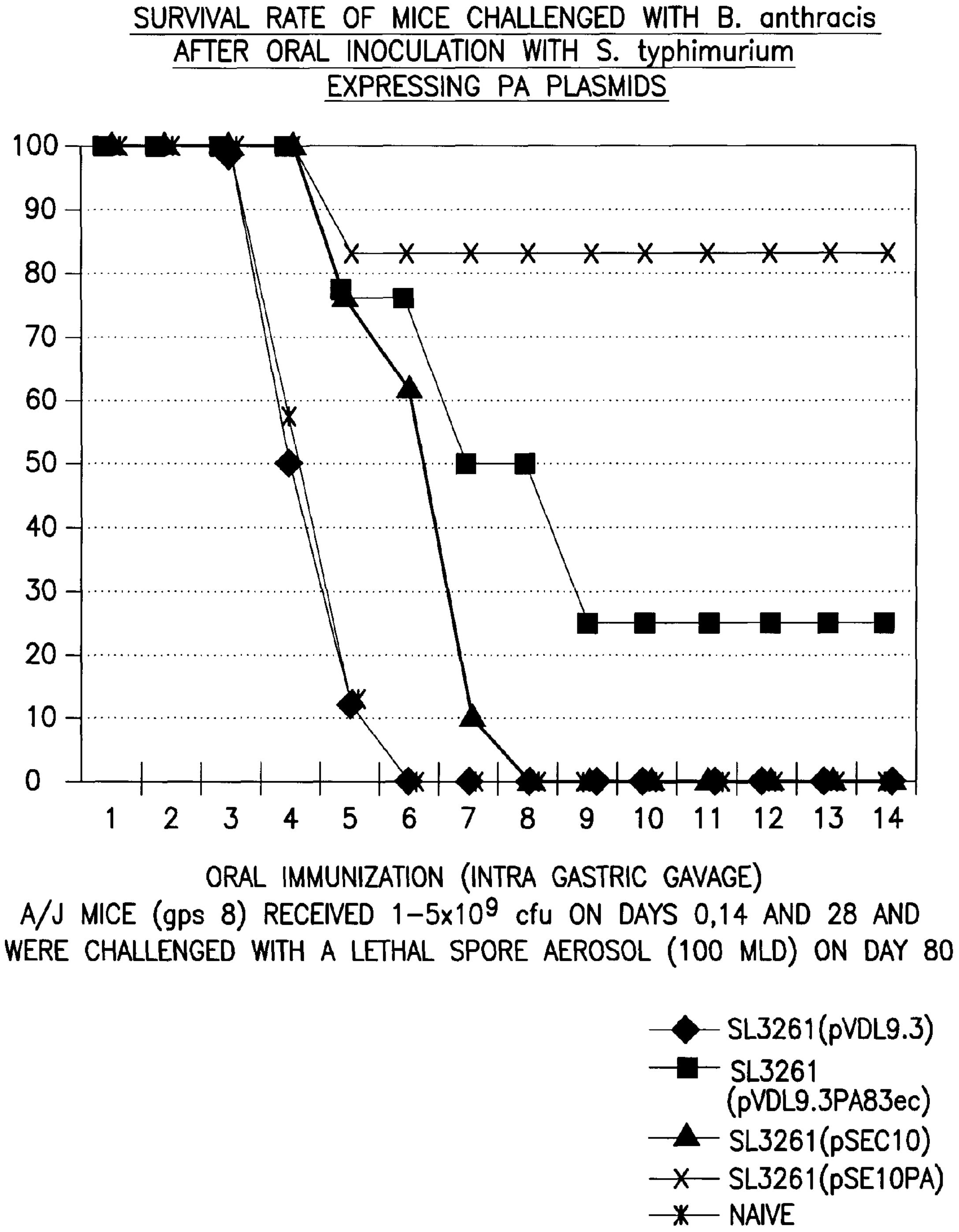

FIG. 23 shows the results of protection studies of mice challenged with *B. anthracis* after oral inoculation with *S. Typhimurium* expressing PA plasmids.

FIG. 24 is an alignment of the original (SEQ ID NO: 11) and codon optimized (SEQ ID NO: 12) nucleotide sequences coding for the optimized region of the LF Domain 1-PA Domain 4 fusion protein, as described in Example 10.

FIG. 25 is a protein alignment of the optimized region of the LF Domain 1-PA Domain 4 fusion protein, aligning the original (SEQ ID NO: 13) and codon optimized (SEQ ID NO: 14) sequences, as set forth in Example 10.

FIG. 26 is the full length optimized LF Domain 1-PA Domain 4 fusion protein (SEQ ID NO: 15), as described in Example 10.

Figure 27:
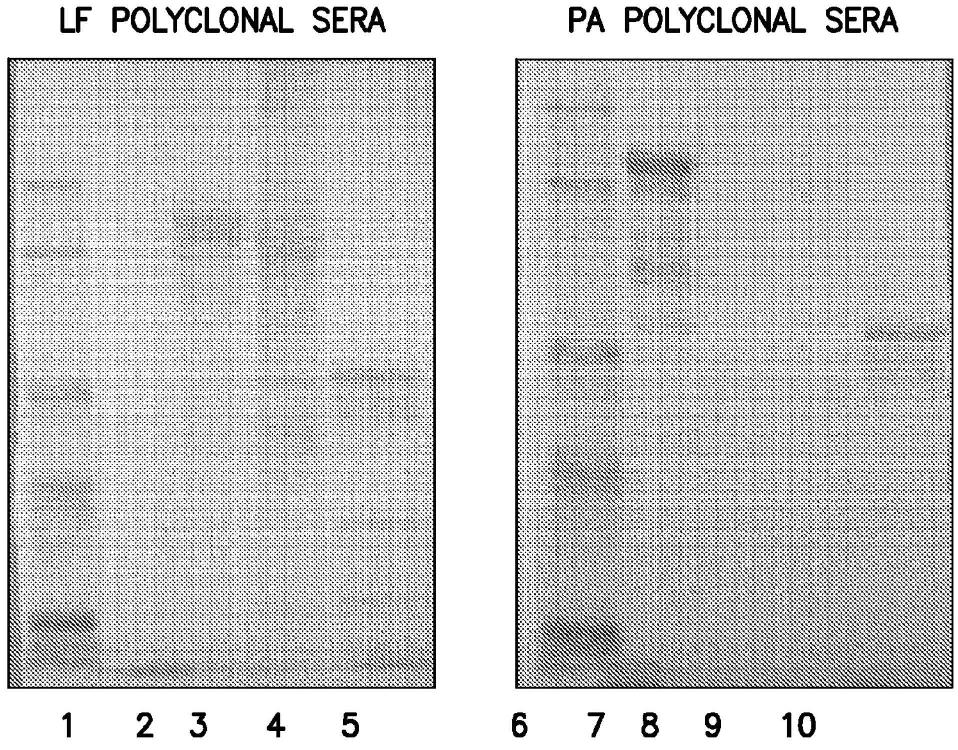

FIG. 27 is a Western blot of the immunogenicity of the LF Domain 1-PA Domain 4 fusion protein, as determined by recognition by rabbit polyclonal anti-PA and rabbit polyclonal anti-LF specific antisera, as set forth in Example 10.

Figure 28:
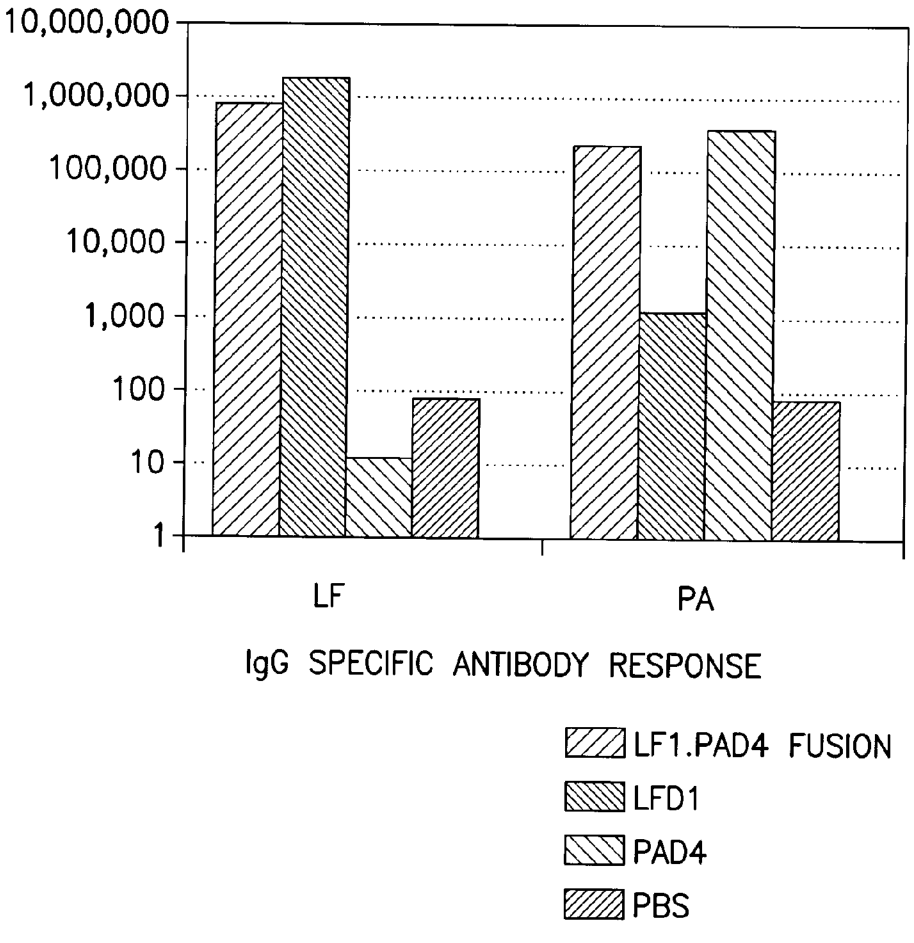

FIG. 28 shows the IgG specific antibody response of BALB/c mice immunized with the LF Domain 1-PA Domain 4 fusion protein, as set forth in Example 11.

Figure 29:
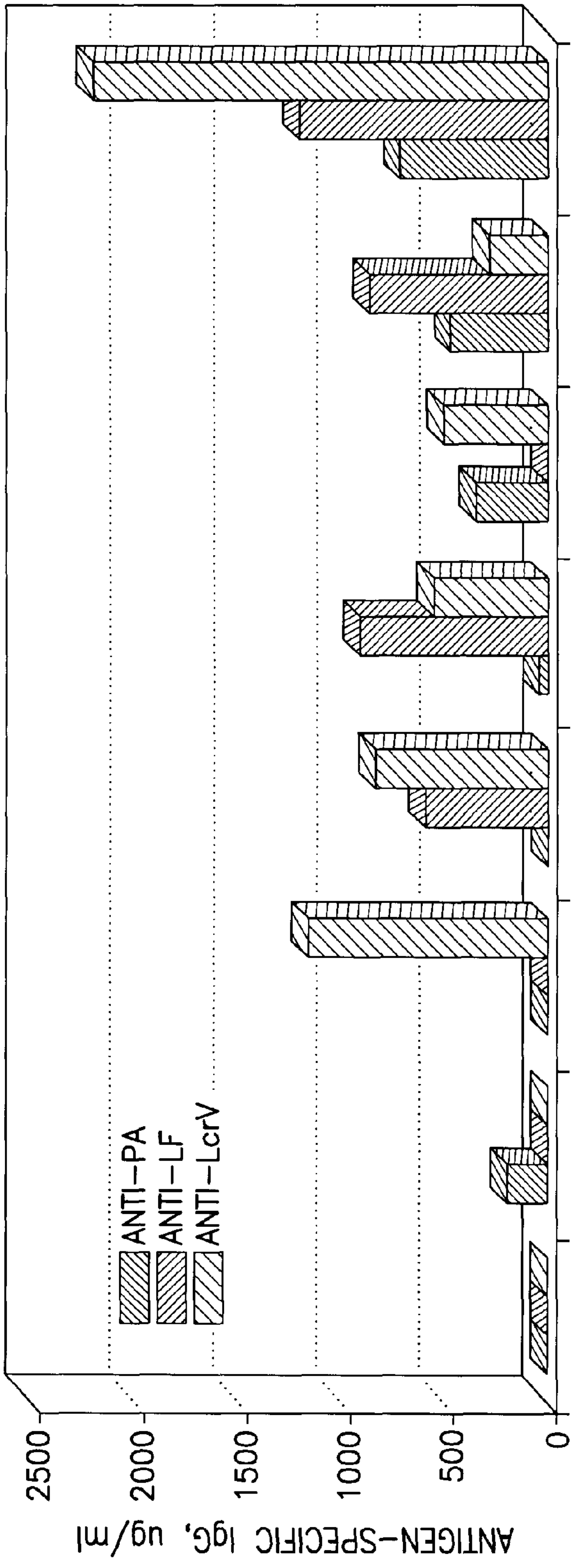

FIG. 29 shows the immunogenicity of LFn/V and V/LFn fusion proteins in BALB/c mice, as set forth in Example 12.

Figure 30:
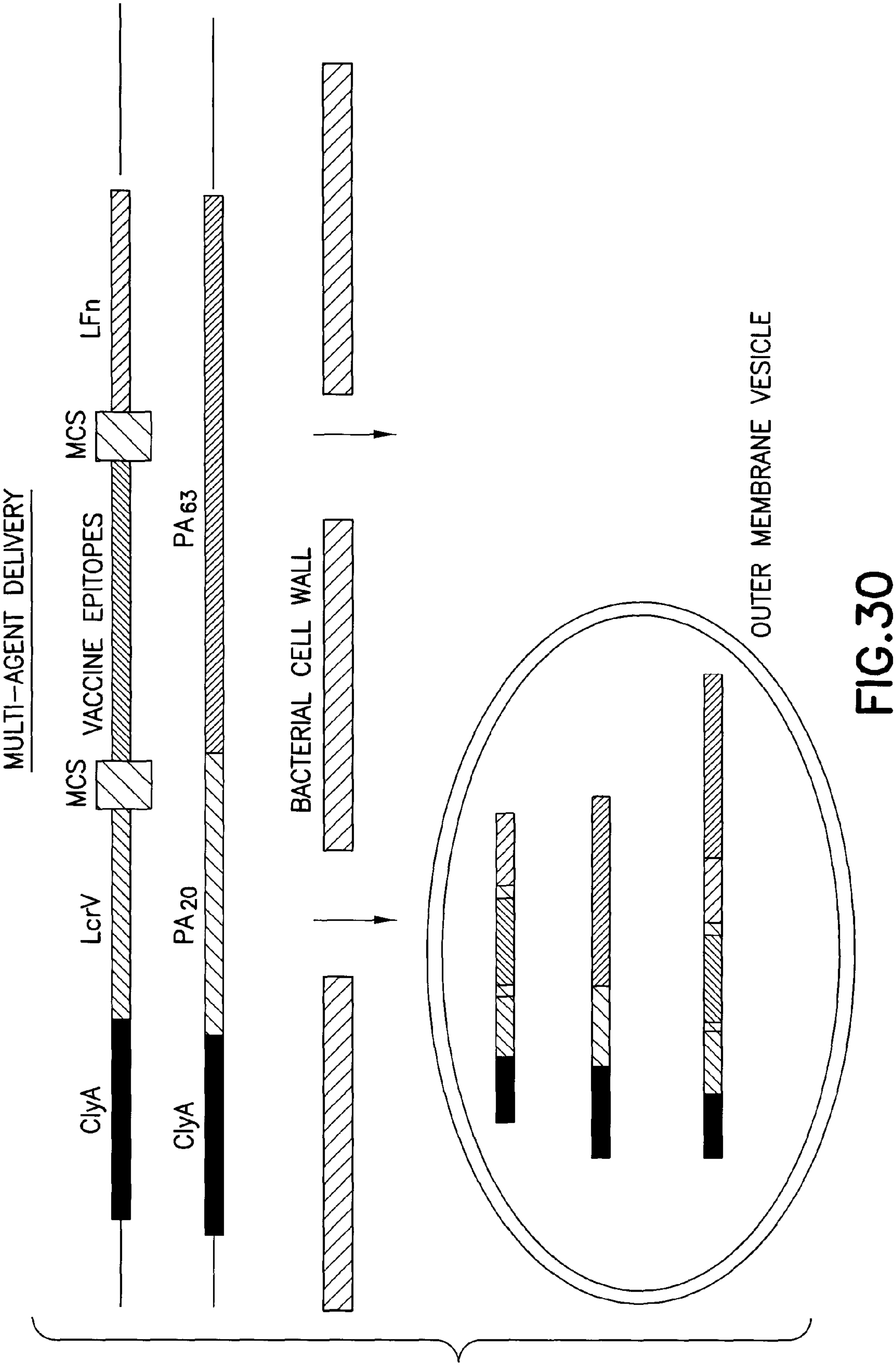

FIG. 30 shows a multi-agent delivery construct of the invention.

FIG. 31 is the complete amino acid sequence (SEQ ID NO: 24) of the LcrV-MCS-LFR4-IQLF-PA2D3-PAD4loop/DR1-F1-L fusion protein, as set forth in Example 13.

FIG. 32 is the *Salmonella* codon optimized gene sequence (SEQ ID NO: 25) of the LcrV-MCS-LFR4-IQLF-PA2D3-PAD4loop/DR1-F1-L fusion protein, as set forth in Example 13.

Figure 33:
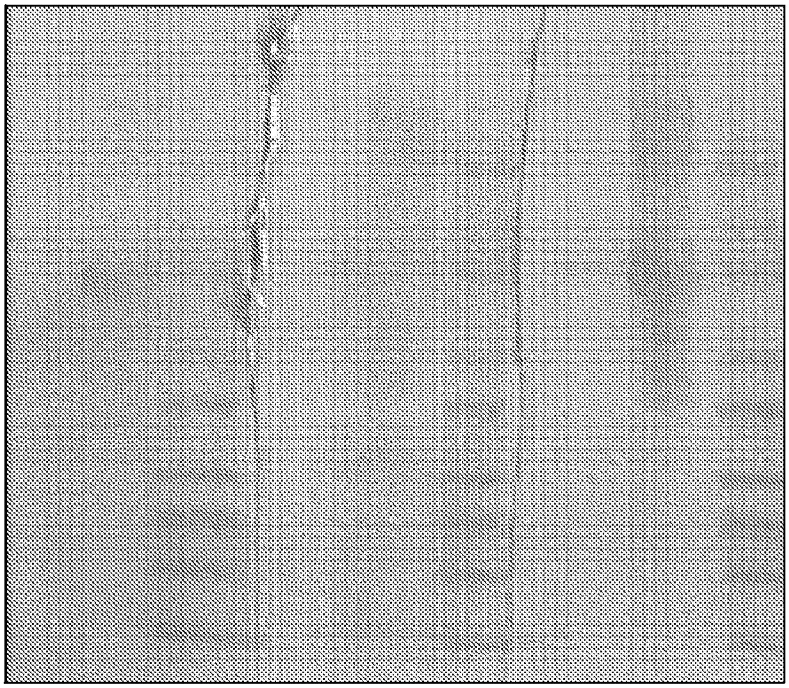

FIG. 33 is a Western blot showing the immunogenicity of the LcrV-MCS-LFR4-IQLF-PA2D3-PAD4loop/DR1-F1-L fusion protein, as set forth in Example 13.

Figure 34:
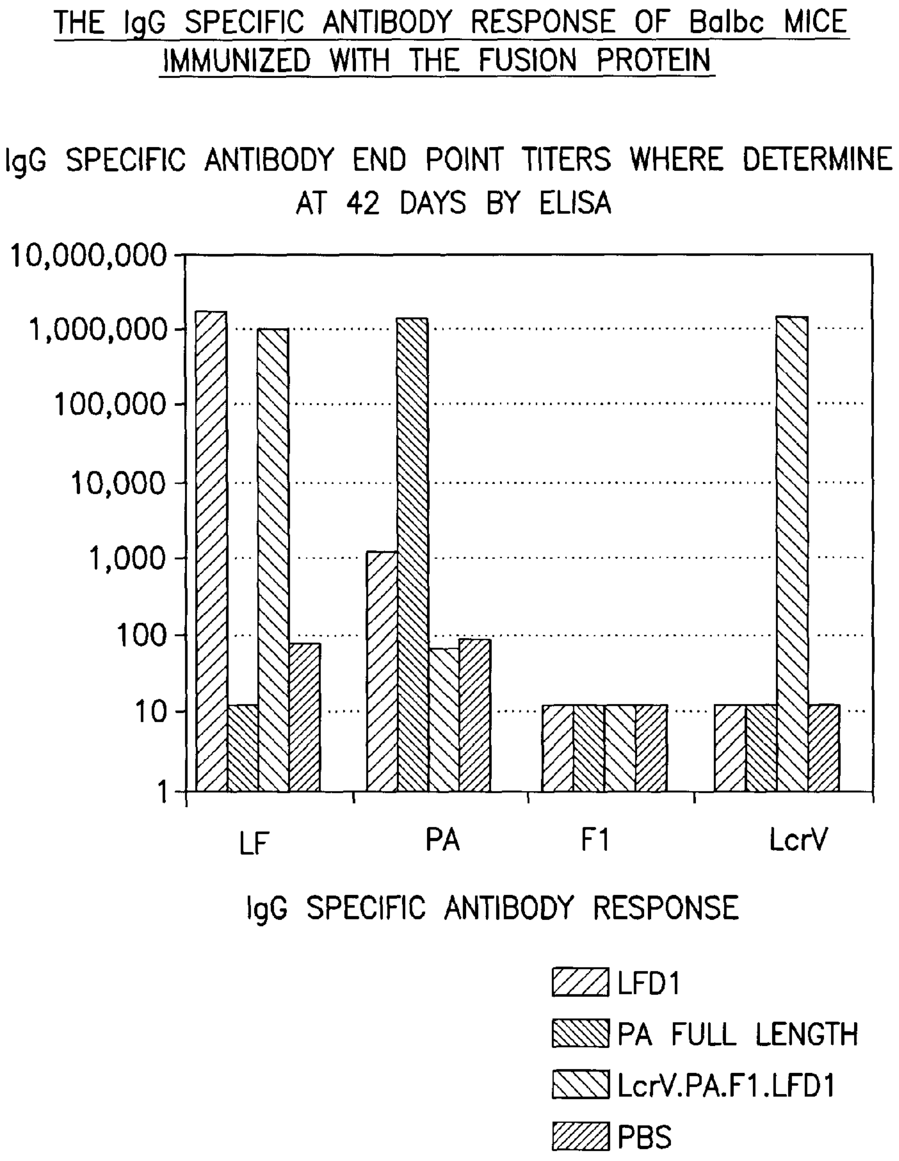

FIG. 34 shows the IgG specific antibody response of BALB/c mice immunized with proteins LFD1, PA and LcrV-MCS-LFR4-IQLF-PA2D3-PAD4loop/DR1-F1-L.

DETAILED DESCRIPTION OF THE INVENTION

A new generation of vaccine against anthrax would ideally contain PA and LF in combination, would be a live vaccine, safe and non-toxic to humans and require minimal dosage in an easily administered manner. The present invention provides such a new generation of vaccine. As set forth below in detail, the vaccines of the invention offer the following advantages:

i) stimulate an LF specific immune response and contribute to protection;

ii) confer sterile immunity against newly emerging anthrax causing organisms and genetically engineered spore formers;

iii) enhance the antibody response to both PA and LF;

iv) stimulate strong T cell memory responses in humans;

v) as an LFn fusion system, facilitate the uptake of additional protective epitopes for anthrax; and vi) provide a platform for the delivery of vaccine targets against a range of targets such as the F1 and LcrV antigens of plague.

"Vaccine" as used herein is a preparation that stimulates an immune response that produces immunity. Vaccines may be used to prevent infection, to create resistance to an infection or to ameliorate the effects of infection. Vaccines may contain, but are not limited to, live, attenuated infectious material such as viruses or bacteria, and dead or inactivated organisms or purified products derived therefrom. A vaccine can be administered by injection, orally or by inhalation. Injection may be, but are not limited to, subcutaneous (sc), intramuscular (im), intraperitoneal (ip), intradermal (id) or intravenous (iv).

"Immunogen" or "antigen" as used herein is a substance that that is foreign to the body that stimulates an immune response, such as the production of antibodies when introduced into the body. Immunogens or antigens are also capable of reacting with the products of an immune response. Immunogens or antigens may include, but are not limited to proteins or polypeptides, enzymes, toxins, bacteria, viruses, foreign tissues, foreign blood cells, and the cells of transplanted organs. Correspondingly, "immunogenicity" is the ability of an immunogen or antigen to stimulate an immune response.

"Antibody" or "immunoglobulin," as used herein is a protein produced by the immune system that helps destroy disease-causing organisms. Antibodies are made and secreted by B lymphocytes in response to stimulation by antigens, which may include vaccines. Antibodies are generally specific, binding only to the specific antigen that stimulated its production. A given antigen can have many epitopes, each one reacting with the immune system to create antibodies specific for each of the epitopes. Antibodies can be effective defenders against both bacteria and viruses, in addition to toxins. Antibodies can be polyclonal or monoclonal.

"Pathogen" as used herein refers to a biological agent, for example, a microbe such as a virus or bacteria that infects its host, causing disease, illness or other deleterious effect on the host. Such pathogens may be introduced through bio-terrorism actions or may be naturally encountered. The vaccine of the claimed invention is useful against pathogens such as, but not limited to, *B. anthracis, B. cereus, S. typhi, F. tularensis, B. abortis, B. pseudomallei, Y. pestis* and *C. botulinum* neurotroxins.

As used herein, a "fusion gene" is a gene created by removing the stop protein from the sequence of a gene and attaching the DNA sequence of a second gene to the first. By fusing one nucleotide sequence to another, the host cell will express the sequences together, as a single fused protein. Fusion genes may contain two or more fused genes. Accordingly, "fusion protein" as used herein is a protein produced by expression of a fusion gene.

PA is the key protective immunogen of the currently licensed human anthrax vaccines. Traditionally, PA based vaccines have suffered from poor levels of expression of PA, requiring multiple dosages of the vaccine. Attempts have been made to develop live *Salmonella* vaccines against anthrax, but attempts to date have been unsuccessful. It is believed that this poor immunogenicity of PA expression in *Salmonella* strains may be due to a number of factors. The codon usage of the PA gene is profoundly different from that on the majority of *Salmonella* genes such that it could cause translation problems. Additionally, high level expression of large foreign genes can place an enormous burden on the *Salmonella*, compromising the biological fitness of the *Salmonella* itself and encouraging the emergence of mutations which inactivate gene expression. The protein itself may be toxic for *Salmonella* resulting in suppression of further protein production. Once expressed in the cytoplasm, the protein is liable to proteolytic degradation by *Salmonella* proteases such that little remains to be exported out of the bacterium and finally the bacterial export system may not be able to efficiently secrete the protein resulting in further degradation of exported protein due to it being unable to assume a stable tertiary configuration.

However, the current invention provides live vaccines, such that they are administered in live, attenuated strains of *Salmonella.*

PA is a powerful immunogen and has generally been the focus of vaccines against anthrax. However, there is also animal protection data to support the inclusion of detoxified LF in a combined PA/LF vaccine. Studies in mice have demonstrated that LF, when expressed from a DNA vaccine, in the absence of PA, is capable of conferring some protection against injected toxin challenge (Price, et al. *Infect. Immun.,* 69(7):4509-15 (2001)). Studies with DNA vaccines expressing human codon optimized LF Domain 1-3 demonstrated partial protection in rabbits against aerosol challenge with spores of the highly lethal Ames strain (Galloway, et al. *Vaccine* 22(13-14):1604-8 (2004); Hermanson et al. *Proc. Natl. Acad. Sci. USA* 14; 101(37):13601-6 (2004)).

Figure 1:
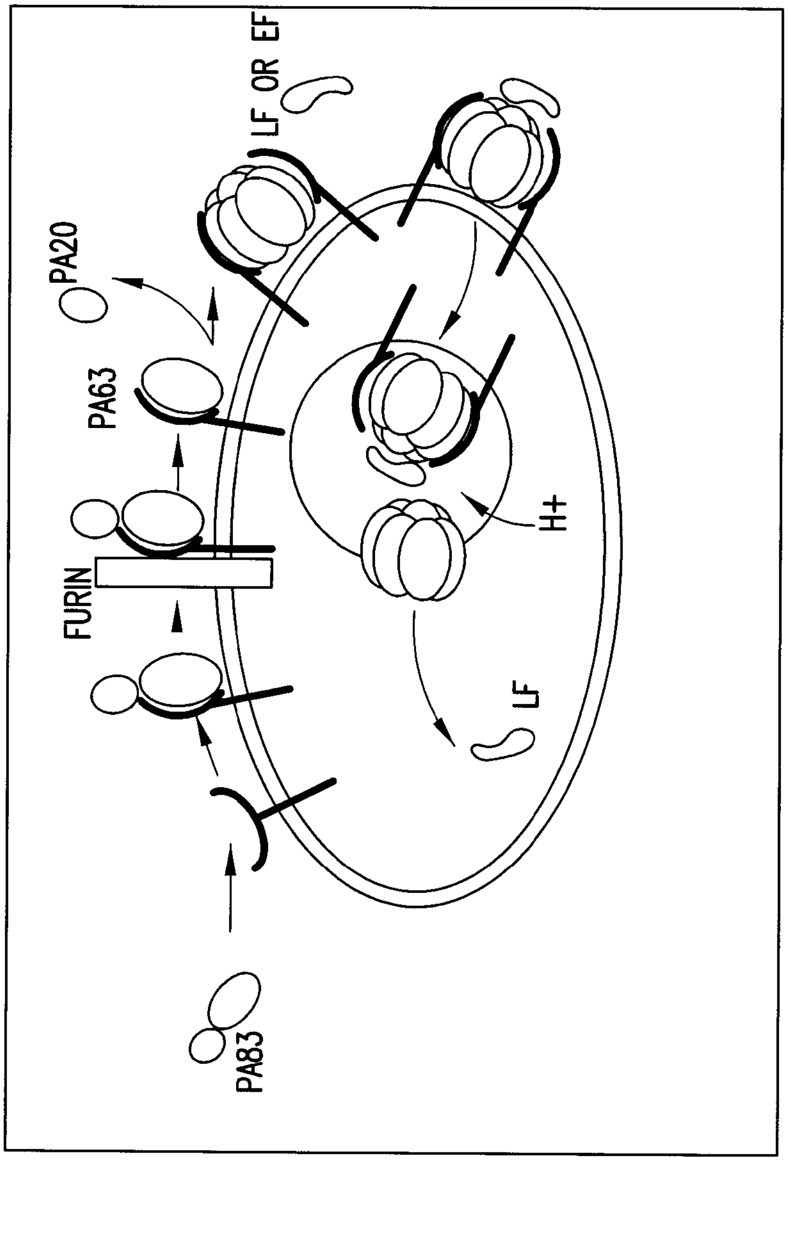
FIG. 1 is a model of cellular uptake of the anthrax toxin. The illustration shows how, upon release PA molecules will selectively bind to host cell receptors. The PA is then cleaved by a protease and forms an activated PA that binds to other active PAs to form a heptamer. LF or EF will bind to the heptamer and the entire complex is drawn into the cell via endocytosis. Once in the cytosol, LF and EF exert their enzymatic activities and damage the cells. EF causes edema and LF causes cell lysis.
Figure 2:
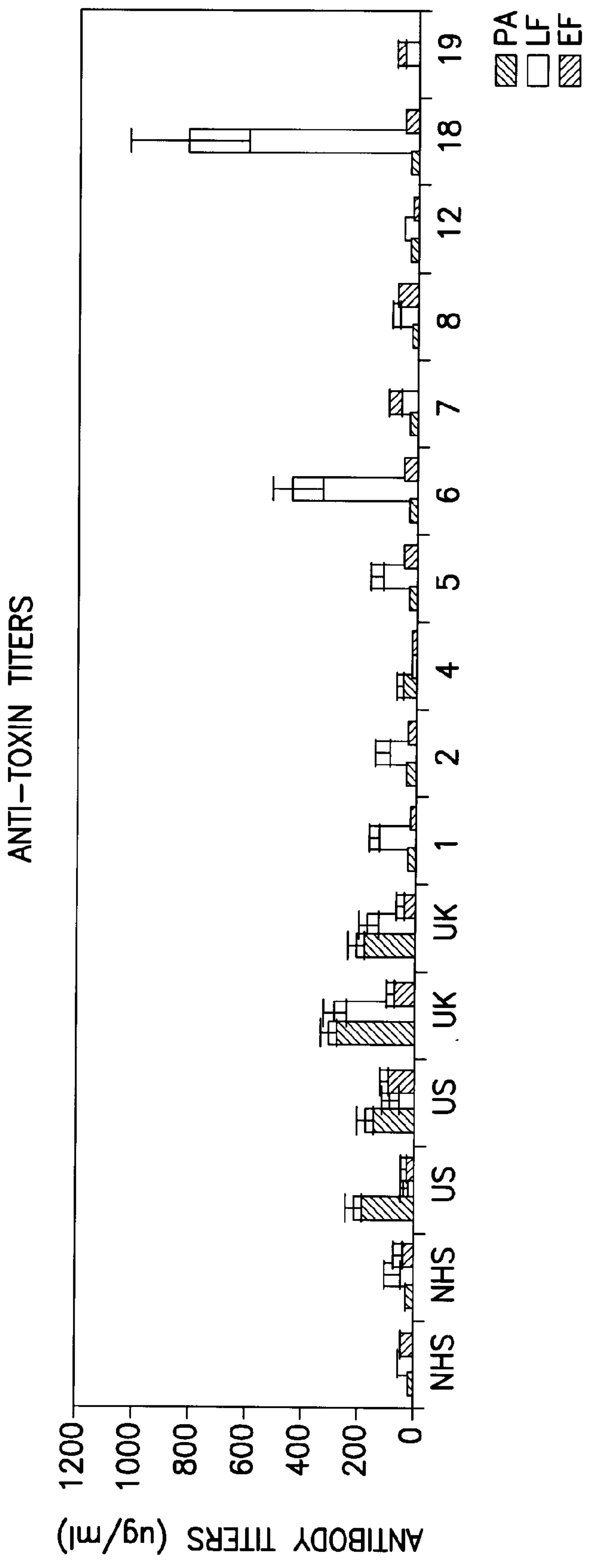
FIG. 2 is a graph showing human serum samples obtained from vaccinated (U.S. and U.K. licensed anthrax vaccines)

The inventor of the present invention has shown that in addition to conferring protection, LF appears to be a more potent human immunogen than PA. The inventor has found that individuals who contract cutaneous anthrax respond much earlier to LF than PA and mount a more robust antibody response. (FIG. 2.)

The inventor has combined his findings with the fact that LF co-administered with PA enhanced the PA specific antibody response of immunized mice. (Pezard et al. *Infect. Immun.* 63(4):1369-72 (1995); Price et al. *Infect. Immun.* 69(7):4509-15 (2001)). This is also illustrated in FIG. 3.

The individual regions of the PA and LF proteins have been determined. The domains of PA have been identified as set forth in FIG. 4. Individual regions that bind protective mouse and human antibodies have been identified. The present inventor has previously identified two such regions, one located within PA Domain 3 which binds the mouse protective monoclonal antibody 2D3 and is recognized by the serum from anthrax vaccinated humans (Baille et al., 2004). An additional binding region within the PA domains is the host binding cell domain of PA (Domain 4) which has also been shown to bind mouse (Flick-Smith et al., 2002a, 2002b) and human toxin neutralizing antibodies (unpublished data, FIG. 4) and be capable of conferring complete protection against lethal spore challenge.

A toxin neutralizing PA Domain 4 specific monoclonal antibody was isolated from an individual who had been vaccinated with a licensed human anthrax vaccine. The ability of the antibody to recognize PA was determined by ELISA and Western blot. The ability of the antibody to neutralize toxin activity was demonstrated in vitro and the ability of the antibody to passively protect mice against a lethal *B. anthracis* spore challenge was confirmed by experiment.

Similarly, the regions of LF have been identified. The domains of LF have been identified as set forth in FIG. 5. The adjuvant effect of LF in combination with PA appears to lie in the N-terminal 254 amino acids of LF (LF Domain 1), the region of the protein which binds to PA and has been exploited by researchers as a means of delivering antigens ranging in size from CTL epitopes of 9 amino acids to HIV proteins of 550 amino acids into the cytosol of antigen presenting cells, leading to the stimulation of CD8 and CD4 T cell responses. (Ballard et al. *Infect. Immun.* 66(10):4696-9 (1998); Ballard et al. *Infect. Immun.* 66(2):615-9 (1998); Lu, et al. *Proc Natl Acad Sci USA* 97(14):8027-32 (2000); Price et al. *Infect. Immun.* 69(7):4509-15 (2001)).

In addition to isolating PA specific human monoclonals, a protective human monoclonal was also isolated which recognized LF Domain 1. The amino acid recognition sequence of this antibody is discussed more fully herein and illustrated in FIG. 19.

Once identified, the individual domains were expressed and assessed for immunogenicity and protective efficacy in mice.

In particular, Example 1 as set forth below determines the IgG specific antibody responses to each of the individual LF domains. The LF gene used for Domain 1 was optimized as set forth in FIG. 16. The codon usage of a gene is known to have a profound effect on its ability to express in different bacterial backgrounds. Previously it was demonstrated that altering the codon usage of the PA gene to that common to *E. coli* markedly increased the level of protein expression from *E. coli* and *Salmonella* spp. (Garmory et al. *Infect. Immun.* 71(7):3831-6 (2003)). Interestingly other researchers have also attempted to optimize the codon use of PA for *Salmonella* with little success. However, alteration of the LF gene in the present invention, as set forth in FIG. 16, reflecting the codon usage of *Salmonella typhi* vaccine strain TY21a will optimize expression of LF Domain 1.

The level of anthrax toxin neutralizing antibodies has been demonstrated to be a correlate of protection against anthrax in mice, guinea pigs and rabbits. Therefore, Example 2 sets forth a determination of the level of anthrax toxin neutralizing antibodies specific to the individual LF domains.

Example 3 then determines the level of immunogenicity of each of the domains, as co-delivered with PA. It is noted that the results of Example 3 show that only LF Domain 1, when given with PA stimulates a toxin neutralizing titer higher than that seen for PA alone. This may be due to the presence of a B cell epitope described herein which is recognized by a human toxin neutralizing antibody. It should be noted that the co-administration of a full length LF with PA reduced the toxin neutralizing titer to a level lower than that seen for PA alone. These results suggest that LF Domain 1 is a stronger vaccine candidate than full length LF in terms of its ability to stimulate toxin neutralizing antibodies in the presence of PA.

Example 4 provides the first demonstration that Domain 1 of LF, when delivered as a purified protein, is able to confer complete protection against lethal spore challenge with *B. anthracis*. This result is supported by fact that Domain 1 contains a protective B cell linear epitope recognized by a human monoclonal antibody which is able to passively protect mice from a lethal spore challenge. Example 5 shows that both this hmAb and a similar protective hmAb against PA are able to bind to spores and facilitate the subsequent killing of the organism by macrophages.

In one embodiment the invention provides a vaccine for the prevention of anthrax comprising a live, attenuated *Salmonella* comprising at least one nucleotide sequence encoding anthrax protective antigen (PA) and at least one nucleotide sequence encoding a non lethal mutated form of anthrax lethal factor (LF). In a preferred aspect, the codons in the nucleotide sequences are preferred by the *Salmonella.*

In another embodiment, the invention provides a method for enhancing antibody response for anthrax protective antigen (PA) in a subject. The method comprises administering a live, attenuated *Salmonella* comprising at least one nucleotide sequence encoding anthrax protective antigen (PA) and at least one nucleotide sequence encoding a non lethal mutated form of anthrax lethal factor (LF). In a preferred aspect, the codons in the nucleotide sequences are preferred by the *Salmonella.*

In still another embodiment, the invention provides a vaccine for the prevention of anthrax, comprising a live, attenuated *Salmonella* comprising at least one nucleotide sequence encoding at least a fragment of anthrax protective antigen (PA) and at least one nucleotide sequence encoding at least a fragment of a non lethal mutated form of anthrax lethal factor (LF). In a preferred aspect, the sequence encoding the fragment of anthrax PA is fused to the sequence encoding the fragment of anthrax LF, forming a fusion gene construct. In a further preferred aspect, the vaccine induces a CTL response in a subject. The mutated form of LF may be wild type LF with replacement of amino acid 687 glutamic acid encoded by the codon GAA with cysteine encoded by the codon TGC, among other mutations. In a preferred aspect, the codons in the nucleotide sequences are preferred by the *Salmonella*, such that expression is maximized.

In another embodiment, the invention provides a method for inducing a cellular immune response in a subject comprising administering a live, attenuated *Salmonella* comprising at least one nucleotide sequence encoding anthrax protective antigen (PA) and at least one nucleotide sequence encoding a non lethal mutated form of anthrax lethal factor (LF). In a preferred aspect, the cellular immune response comprises increased secreting T lymphocytes. In another preferred aspect, the subject is human.

In still another embodiment, the invention provides a vaccine for the prevention of anthrax, comprising a live, attenuated *Salmonella* comprising at least one nucleotide sequence encoding anthrax protective antigen (PA) or a fragment thereof and at least one nucleotide sequence encoding a non lethal mutated form of anthrax lethal factor (LF) or a fragment thereof. In a preferred aspect, the sequence encoding the PA or fragment of PA is fused to the sequence encoding the LF or fragment of LF, forming a fusion gene construct. In a further preferred aspect, the mutated form of LF may be wild type LF with replacement of amino acid 687 glutamic acid encoded by the codon GAA with cysteine encoded by the codon TGC, among other mutations. In one aspect, the fragment of LF is Domain 1. In another aspect, the PA is full length and the LF is a fragment, where the fragment is Domain 1. In yet another aspect the vaccine induces a CTL response in a subject. In another preferred aspect, the vaccine induces an anthrax toxin neutralizing activity. In still another preferred aspect, the codons in the nucleotide sequences are preferred by the *Salmonella*, such that expression is maximized.

Additionally, the invention provides a vaccine that delivers epitopes to the immune system. In one aspect a construct comprising LF Domain 1 will be utilized where the LF contains at least one epitope of interest. Such epitopes may include, but are not limited to key protective T (CD4) and B cell epitopes.

The inventor has characterized the inherent immunogenicity of the LF Domain 1 for humans. Using serum and cells from human volunteers immunized with the U.K. licensed anthrax vaccine, which contains PA and low levels of LF, it has been shown that LF Domain 1 contains both protective B cell (SDVLEMYKAIGGKIYUVDGDITKHISLEAL (SEQ ID NO: 6)) and immunodominant human CD4 T cell epitopes (Baillie et al., 2004; manuscript in preparation). The inventor has also generated a human monoclonal antibody from a previously immunized donor which binds LF Domain 1 and protects laboratory animals from a lethal anthrax spore challenge.

In addition to neutralizing toxin activity the inventor has also identified certain PA and LF specific antibodies with opsonic activity. It has been previously found that polyclonal human PA specific IgG antibodies bind to the anthrax spore surface and promote uptake by macrophages in such away that the germinating bacterium is subsequently killed before it has the chance to initiate significant gene expression thus achieving sterile immunity (Kang et al., *Infect. Immun.* 73(11):7495-501 (2005)). The inventor has demonstrated a similar phenomenon with human monoclonal antibodies which recognize PA and LF Domain 1 (unpublished data).

The ability to kill the organism before it has the change to express virulence genes, be they naturally present or acquired as the result of genetic engineering, is of considerable advantage in the context of emerging bio-threats. In recent years the feasibility of introducing additional virulence genes in to *B. anthracis* was demonstrated by researchers in the former Soviet Union who generated a strain which defeated the Russian human anthrax vaccine (Pomerantsev et al., *Vaccine* 15(17-18):1846-50 (1997)). It is also possible to transfer the major toxin genes from *B. anthracis* and have them expressed in the genetic close relative *B. cereus* (Hoffmaster et al., *Proc. Natl. Acad. Sci. USA* 101(22):8449-54 (2004)).

Therefore, the present invention provides a vaccine containing relevant PA and LF specific epitopes, as described above, which stimulate antibodies which confer sterile immunity and thus confer protection against these strains of anthrax.

Thus in one embodiment, the invention provides vaccine for the prevention of anthrax, comprising a live, attenuated *Salmonella* comprising at least one nucleotide sequence encoding at least a fragment of anthrax protective antigen (PA) and at least one nucleotide sequence encoding at least a fragment of a non lethal mutated form of anthrax lethal factor (LF), wherein the fragments of the protective antigen and lethal factor include at least one active epitope. In various aspects of the invention, the active epitope(s) may include, but are not limited to a furin cleavage site of the protective antigen, a host cell binding domain of the protective antigen, the N-terminal region of the lethal factor, T and B cell epitopes. In an additional aspect of the invention, the nucleotide sequence further encodes for C3D at the C-terminal end of the fusion construct. In a preferred aspect, the codons in the nucleotide sequences are preferred by the *Salmonella.*

In another embodiment, the invention provides a vaccine for the prevention of anthrax, comprising a live, attenuated *Salmonella* comprising at least one nucleotide sequence encoding anthrax protective antigen (PA) or a fragment thereof and at least one nucleotide sequence encoding a non lethal mutated form of anthrax lethal factor (LF) or a fragment thereof, wherein the wherein the PA or fragment thereof and LF or fragment thereof include at least one active epitope.

In a still another embodiment, the mutated form of LF may be wild type LF with replacement of amino acid 687 glutamic acid encoded by the codon GAA with cysteine encoded by the codon TGC, among other mutations. In one aspect, the fragment of LF is Domain 1. In another aspect, the PA is full length and the LF is a fragment, where the fragment is Domain 1. In still another aspect, the epitope is a T cell epitope. In still a further aspect, the epitope is a B cell epitope. In still another preferred aspect, the codons in the nucleotide sequences are preferred by the *Salmonella*, such that expression is maximized.

In still another embodiment, the invention provides a method of stimulating antibody response in a subject, comprising administration of a live, attenuated *Salmonella* comprising at least one nucleotide sequence encoding anthrax protective antigen (PA) or a fragment thereof and at least one nucleotide sequence encoding a non lethal mutated form of anthrax lethal factor (LF) or a fragment thereof, wherein the LF contains at least one active epitope, wherein at least one antibody to the epitope is stimulated. In a further preferred aspect, the mutated form of LF may be wild type LF with replacement of amino acid 687 glutamic acid encoded by the codon GAA with cysteine encoded by the codon TGC, among other mutations. In one aspect, the fragment of LF is Domain 1. In another aspect, the PA is full length and the LF is a fragment, where the fragment is Domain 1. In still another aspect, the epitope is a T cell epitope. In still a further aspect, the epitope is a B cell epitope. In one aspect the antibody stimulated is a monoclonal antibody. In another aspect the antibody is a human monoclonal antibody. In still another aspect, the antibody confers immunity to the subject such that the subject is protected against a strain of anthrax subsequently introduced to the subject. In a further aspect of this embodiment, the strain of anthrax is *B. anthracis* or *B. cereus* G9241. In still another preferred aspect, the codons in the nucleotide sequences are preferred by the *Salmonella*, such that expression is maximized. In an additional aspect the subject is human.

Including epitopes to both LF in addition to PA would be useful in the case of deliberate circumvention of epitope binding sites within PA such that they are no longer recognized by previously protective antibodies but still retain their biological function (Rosovitz et al., 2003). For example, *B. cereus* G9241 possess two homologs of the PA gene, the first encodes a protein (PA1) identical to that of *B. anthracis* while a second homolog (PA2) which shows 60% amino acid identity and is thought to be biologically functional and is not recognized by antibodies raised against PA1 (Hoffmaster et al., 2004; unpublished data). Since PA1 is the major protective immunogen of both the current licensed human anthrax vaccine and its second generation replacement, there are concerns that these vaccines will be unable to stimulate a protective response against G9241.

While G9241 expresses two copies of PA it has only one complete copy of LF. The expression of this gene was confirmed by Western blotting individual LF domains with serum from a rabbit which had been exposed to G9241 (FIG. 12).

Therefore in another embodiment, the invention provides vaccines including individual epitopes. In one embodiment the invention provides a vaccine for the prevention of anthrax comprising a live, attenuated *Salmonella* comprising at least one nucleotide sequence encoding anthrax protective antigen (PA) Domain 4 or a fragment thereof. In a further aspect the PA Domain 4 or a fragment thereof contains at least one active epitope.

In another embodiment the invention provides a vaccine for the prevention of anthrax comprising a live, attenuated *Salmonella* comprising at least one nucleotide sequence encoding a non lethal mutated form of anthrax lethal factor (LF) Domain 1 or a fragment thereof. In a further aspect the LF Domain 1 or a fragment thereof contains at least one active epitope.

In addition to contribution directly to protection, the LF protein can also be employed to present fusion proteins to the immune system. One example of a fusion construct of the invention is set forth in FIG. 6. There appear to be at least two mechanisms involved in LF mediated uptake. The first is PA dependent and makes use of the ability of the PA to transport LF into the cytosol of the cell (Ballard et al. *Infect. Immun.* 66(10):4696-9 (1998); Ballard et al. *Infect. Immun.* 66(2):615-9 (1998); Lu, et al. *Proc Natl Acad Sci USA* 97(14):8027-32 (2000)). It is capable of delivering LF Domain 1 fusion proteins as large as 500 amino acids into antigen presenting cells and stimulating both CTL and CD4 responses. This system is extremely potent requiring as little as 300 fmol of fusion to stimulate a response in mice and does not require the presence of an external adjuvant. Using this approach, researchers were able to prime a CTL response without invoking an antibody response to either PA or LF Domain 1 (Ballard et al., 1998). The second mechanism is PA independent and is enhanced by the presence of the adjuvant Alum (Cao et al., J. Infect. Dis. 185(2):244-51 (2002), Kushner et al., *Proc Nat Acad Sci USA* 100(11):6652-7 (2003)). The fusion protein were found to localize with the 20s subunit, which degrades proteins into peptides for presentation to CD8 T cells by the MHC class 1 pathway. These results suggest that LF Domain 1 may be used as a carrier to deliver antigens into the cytosol of antigen presenting cells for efficient induction of T cell responses.

Utilization of LF Domain 1 as such a carrier can be effected by fusing LF Domain 1 to the additional vaccine targets from other infectious agents for delivery to the immune system. The ability of LF Domain 1 to deliver vaccine epitopes to the immune system has been previously reported by Ballard. An example of this utility is set forth below in Example 10, where a fusion protein of LF Domain 1 and PA Domain 4 has been generated and delivered.

Additionally, the invention provides an LFn-fusion construct which includes epitopes for an additional pathogen. Such epitopes may include, but are not limited to, protective epitopes or regions of PA, protective regions or epitopes of anthrax, LcrV and/or F1, as set forth in the examples below. Such a fusion construct may consist of one or more additional epitopes for one or more additional pathogens.

In still another aspect, the additional pathogen is plague. In the case of plague, two vaccine target antigens have been identified, F1 and LcrV, which are currently undergoing phase II human trials in the U.S. and Europe. The F1 protein is expressed optimally at 37° C. and is thought to inhibit phagocytosis through the formation of a capsule-like structure on the bacterial surface. LcrV plays a key role in type III secretion by *Yersinia* spp, a process that allows the injection of a set of effector proteins (YOPS) directly into the cytosol of eukaryotic target cells which promote the killing of phagocytic cells. Evidence has accumulated from a number of studies that antibody plays a key role in protection against plague. Circulating antibodies specific for F1 and LcrV antigens are thought to access the bacterium in its predominantly extracellular state and bind to surface exposed protein. While F1 and LcrV antigens have been shown to induce protective immunity when administered individually, in combination or as a fusion, these proteins have been shown to have an additive protective effect when used to immunize mice against plague. As set forth in Example 12, LFn/V and V/LFn fusion proteins are immunogenic.

Based on the above findings, a further aspect of the invention is a multivalent vaccine platform base in an attenuated *Salmonella* strain which is able to deliver LFn linked to fusion proteins such as LcrV and F1 or specific protective B and T cell epitopes, as set forth in FIG. 30. Still another aspect of the invention is a fusion protein as set forth above, but omitting PA. This latter aspect is based on the protective character of LFn, e.g., when administered as a protein. This protection can be achieved by incorporating protective regions from PA into the LFn fusion construct.

Accordingly, in one embodiment the invention provides vaccine for the prevention of anthrax comprising a live, attenuated *Salmonella* comprising at least one nucleotide sequence encoding a non lethal mutated form of anthrax lethal factor (LF) or a fragment thereof and at least one nucleotide sequence encoding an antigen of an additional pathogen or fragment thereof. In one aspect the sequence encoding the LF or fragment thereof is fused to the sequence encoding the antigen of the additional pathogen. In still another aspect the LF or fragment thereof includes at least one active epitope. In another aspect the LF is LF Domain 1. In a further aspect the additional pathogen is plague. In still another aspect the antigen includes at least one active epitope. In a still further aspect, the active epitope may be, but is not limited to F1 or LcrV.

A still further aspect of the invention provides a fusion protein with only those B and T cell epitopes key to protection against a certain pathogen fused to LF Domain 1. The resulting protein will be considerably smaller than a protein containing large numbers of fused epitopes and thus entails a lower likelihood of physiological stress when expressed from *Salmonella*, as well as a lower likelihood of toxicity issues.

In yet another embodiment, the invention provides a method of stimulating antibody response in a subject comprising administration of a live, attenuated *Salmonella* comprising at least one nucleotide sequence encoding a non lethal mutated form of anthrax lethal factor (LF) or a fragment thereof fused to at least one nucleotide sequence encoding an antigen of an additional pathogen or fragment thereof. In the embodiment, the LF contains at least one epitope and at least one antibody is generated to the epitope. Furthermore, at least one antibody is generated to the antigen of the additional pathogen. In another aspect the stimulated antibody response to the LF epitope confers immunity to the subject against anthrax, genetically modified *B. anthracis* or anthrax-like strains subsequently introduced to the subject. In another aspect the stimulated antibody response to the antigen of the additional pathogen confers immunity to the subject against a strain to the pathogen subsequently introduced to the subject. In one aspect the subject is human. In another aspect the additional pathogen is plague.

In addition, heterologous primer-boosting may be performed to increase the immune response to an antigen. In particular, heterologous primer-boosting may be described as the administration of two different vaccines that encode the same antigen at various times points, by the same or alternative routes. The implementation of such a strategy has been shown to improve the immune response to PA in a range of animal species including primates. An example of such heterologous primer-boosting can be seen in Example 8 set forth below. Therefore, in one aspect, the invention provides vaccines generating an increased immune response due to heterologous primer-boosting, as compared to administration of the vaccine without such boosting.

Finally, the invention provides a fusion construct with the molecular adjuvant C3D incorporated into the fusion construct at the C terminus. C33 is utilized due to its inability to enhance the level and affinity of the antibody response. C3D is a fragment of the third component of the compliment activation pathway. (FIG. 7) It is thought to exert its effect in 2 ways, 1) acting directly on memory B cells via the CD21 receptor amplifying the activation of the cell following binding of the antigen to its immunoglobulin receptor, which in turn stimulates antibody production and 2) enhancing binding of the fusion protein to follicular dendritic cells resulting in the generation of high affinity antibodies thus enhancing the quality of the immune response. This approach has been previously used to enhance antibody responses and protective immunity to influenza virus by generating high affinity neutralizing antibodies to hemagglutinin (Ross et al 2000).

Accordingly, inclusion of C3D will similarly enhance the antibody response to PA and LF and protective immunity to anthrax.

A vaccine of the invention, comprising PA and Domain 1 of LF, affords considerable advantages over the current vaccine, particularly against newly emerging and genetically engineered anthrax strains. Such strains may include, but are not limited to, *B. cereus* G9241. The ability to target both PA and LF provides a broad spectrum utility of this vaccine. In addition the PA/LF Domain 1 system provides a basis for a multi-agent platform capable of conferring protection against a range of infectious agents.

The vaccines of the invention may also be used to confer protection against infectious agents in addition to anthrax. In this embodiment, a single oral dose would confer protection against all included threats of infection. Such additional agents may include, but are not limited to, plague, such as that caused by *S. typhi*. As such, the vaccines will protect the subject against a range of public health pathogens. Such a multi-agent platform can be utilized to confer protection against any one or a combination of the following infectious agents: *B. anthracis, B. cereus, S. typhi, F. tularensis, B. abortis, B. pseudomallei, Y. pestis* and *C. botulinum* neurotroxins. Other such agents will be known to those in the art.

The vaccines of the invention may be used in methods of prophylaxis and treatment. As utilized in treatment, the vaccines may be administered to a subject previously exposed to an infectious agent. Administration of the vaccines of the invention stimulates an immune response in a subject, generating antibodies against the infectious agent. As such, the vaccines of the invention may be administered before or after exposure to an infectious agent in order to stimulate such an immune response.

The following examples are intended to illustrate but not limit the invention.

Example 1

Determination of Immunogenicity of Individual LF Domains

This example was performed to determine the regions of LF capable of stimulating a protective immune response when given as a vaccine. In order to maximize LF expression in *E. coli* and *Salmonella*, the codon usage of the LF gene was optimized, as shown in FIG. 16. The resynthesized gene comprising the mature protein was detoxified, by replacing the glutamic acid at position 687 within the catalytic center with a cysteins (Klimpel, Arora and Leppla, *Mol. Microbiol.*, 1994, 13(6); 1093.). Individual LF domains (see FIG. 5) were cloned and expressed from *E. coli* M15 (pREP4) using a pQE-30/pQE-80L, an N-terminal Hist tag expression system (QIAgen, Inc., Valencia, Calif.).

The immunogenicity of the expressed and purified LF domains was determined in BALB/c mice. Each group, comprising 10 animals, received i.m. 10 ug of domain protein together with the adjuvant alum on days 0 and 28. Animals were bled on days 1, 13, 27, 56 and 72. The LF specific IgG antibody responses were determined by ELISA. The results are shown in FIG. 8, showing the extreme immunogenicity of domains 1, 2, 4 and 2-4, as compared to a negative control and phosphate buffered saline (PBS).

Example 2

Toxin Neutralizing Activity by Antibodies Specific to Individual LF Domains

The ability of the individual expressed and purified LF domains to stimulate toxin neutralizing antibodies was determined in BALB/c mice. Each group, comprising 10 animals, received i.m. 10 ug of domain protein together with the adjuvant alum on days 0 and 28. Animals were bled on days 1, 13, 27, 56 and 72. The LF specific IgG antibody responses were determined by ELISA.

The ability of antibodies specific to individual LF domains to neutralize toxin activity was determined. The results are set forth in FIG. 9. As can be seen in the figure, full length PA was the most effective at stimulating toxin neutralizing antibodies. Domains 1, 2, 4 and 2-4 showed moderate levels of stimulation of toxin neutralizing antibodies, as did biologically inactive full length LF. Domains 3 and 4 showed no detectable toxin neutralization.

Example 3

Determination of Immunogenicity of Individual LF Domains Co-Delivered with PA Groups of 10 BALB/c mice were immunized with 10 ug of each protein with PA with alum i.m. on days 0 and 28. Animals were bled on days 1, 13, 27, 56 and 72 and the IgG response to PA and each LF domain was determined by ELISA. FIG. 10 shows the results. Only Domain 3 showed an increase in LF specific IgG antibody response when co-administered with PA. The same was true for the PA specific IgG response (data not shown).

It should be noted that the individual domain specific antibody responses stimulated during this study were extremely high and as a consequence any adjuvant effects may have been swamped. The toxin neutralizing titer (Example 2) is a more precise measure of protection against anthrax. The mean toxin neutralizing antibody titers for the animals immunized with PA and LF domains is shown in FIGS. 11 and 12.

This data suggests that with the exception of LF Domain 1, that co-administration of full length LF with PA actually inhibits the quality of the toxin neutralizing response.

Example 4

Protection Against Anthrax by Administration of Biologically Inactive Full Length LF or LF Domain 1

The ability of biologically inactive LF (replacement of amino acid 687 glutarnic acid (GAA) with a cysteine (TGC) (Klimpel et al., 2004); See FIG. 16) and LF Domain 1 to protect A/J mice against a lethal anthrax spore challenge was determined.

Each group, comprising 8 animals, received i.m. 10 ug of protein together with the adjuvant Alhydrogel on days 0, 4 and 28. Animals were given a lethal i.p. spore challenge (100 MLDs) on day 80. Results are shown in FIG. 13 and it can be seen that Domain 1 of LF conferred complete protection against a lethal spore challenge with *B. anthracis.*

Example 5

Generation of Antibodies to LF Domain 1 and PA

Domain 1 contains a protective B cell linear epitope recognized by human monoclonal antibody which is able to passively naive protect mice from a lethal spore challenge.

As previously noted this hmAb, and a similar protective hmAb against PA, is able to bind to spores and facilitate the subsequent killing of the organism by macrophages (FIG. 14).

Example 6

Expression of LF Domain 1 in *S. Enterica* serovar Typhimurium SL3261

As LF Domain 1 is protective as a protein against *B. anthracis*, both codon optimized (LFoN) and native (LFnN) versions of LF Domain 1 were generated and individually fused to *S. enterica* serovar Typhimurium cytolysin A (ClyA) as a ClyA fusions in pSEC10. Expression of the protein from *Salmonella* is shown by Western blot in FIG. 20, as probed with mouse monoclonal antibody to LF Domain 1. Individual lanes in FIG. 20 show the following: lanes: 1) Bio-Rad low range standards; 2) SL3261/pSEC10-LFnN#26; 3) SL3261/pSEC10-LFnN#29; 4) SL3261/pSEC10-LFnN#31; 5) SL3261/pSEX10-LFoN#26; 6) SL3261/pSEC10-LFoN#27; 7) SL3261/pSEC10-LFoN#33); 8) Recombinant LF dom 1; 9) *E. coli* TOP10/pSEC10; 10) Bio-Rad low range standards.

Example 7

Expression of PA in *Salmonella*

Two plasmid constructs were made expressing an identical, codon optimized version of the PA gene. (Williamson et al., WO/2002/04646.)

The first construct, pVDL-9.3PAsec is a low copy number plasmid which has been used to express PA as a fusion to the *Escherichia coli* haemolysin (Hly) export system, in order to enable export of the expressed PA protein from the *Salmonella* (Garmory et al 2003). The second construct, pSEC10PA, is based on a recently described *S. enterica* serovar Typhi cytolysin A (ClyA) export system which has been used to express a domain of PA from *Salmonella* (Galen et al., 2004).

To determine the immunogenicity of the constructs, the plasmids described above were transformed into the human vaccine strain *S. typhi* Ty21a and assessed for immunogenicity in BALB/c mice when given via the intranasal route. The results are seen in FIG. 21.

The results show that Ty21a pSEC/PA stimulated an extremely robust PA specific IgG antibody response (FIG. 21*a*). This marked difference in immune response was not due to any failure in the mice in recognizing the *Salmonella* construct as all animals immunized with *Salmonella* generated strong LPS specific immune responses (FIG. 21*b*).

Example 8

Heterologous Prime Boost

Recently it was demonstrated that the attenuated vaccine strain *Salmonella enterica* serovar Typhi strain CVD 908-htrA expressing fragment C of tetanus toxin was able to stimulate significantly higher serum antitoxin responses in mice when the animals received an initial intranasal priming dose of *Salmonella* followed by an intramuscular boost with tetanus toxoid (Vindurampulle et al., 2004).

This example provides animals immunized with *S. Typhi* Ty21a expressing PA and boosted with a single i.m. dose of 1 ug recombinant PA (rPA) protein with the adjuvant alum 56 days after the last *Salmonella* dose. A group of naïve mice received 1 ug of rPA as a reference control. The results are summarized in FIG. 22.

FIG. 22 shows that boosting with rPA further enhances the magnitude of the PA specific immune response in all of the animals. While naïve mice demonstrated a three fold increase in PA specific titer the response of the mice immunized with Ty21a expressing PA varied depending on the vector.

Those animals given Ty21apVDL9.3pA83ec showed a much greater increase in PA titer, >3 logs, than the mice previously immunized with Ty21apSECPA/10 who only managed an increase in the 1-2 log range, comparable to that seen in the naïve animals which received rPA alone. This may be due to the fact that the animals given Ty21a pSEC/PA10 already had high levels of PA specific IgG at the time of the protein boost and as a consequence the antibody response of the animals was overloaded.

These results suggest that while Ty21a pVDL9.3pA83ec may not be as effective as Ty21a pSEC/PA10 at directly stimulating PA specific IgG response it can confer a robust memory response.

Example 9

Protection Studies of Mice Challenged with *B. anthracis* After Inoculation with *S. typhimurium* Expressing PA Plasmids To determine the ability of *Salmonella* constructs expressing PA to protect against exposure to a fatal aerosol challenge with spore of *B. anthracis*, groups of A/J mice were immunized 3 times at two week intervals with approx $1\times10^9$ cfu/ml of *S. typhimurium* SL3261 by the oral route. Positive control mice were immunized by the i.p. route with 3×10 μg of purified recombinant protein adjuvanted with alhydrogel at two week intervals.

Following immunization, mice were challenged with approximately $1\times10^5$ CFU of aerosolized *B. anthracis* STI ($Tox^+$ $Cap^-$) spores and monitored for survival. Naïve mice and those given the SL3261 parental control strain succumbed to infection within 6 days, while the mice receiving SL3261/pSEC10 all died by day 8.

However, 2 of 8 mice immunized with SL3261/pVDL-9.3PAsec were protected against challenge, and 5 of the 6 mice inoculated with SL3261/pSEC10PA also survived. Thus, SL3261/pSEC10PA expressing the full-length PA protein as a fusion with ClyA, afforded significant protection against aerosolized *B. anthracis* spore challenge ($p<0.01$ compared to SL3261/pSEC10).

Example 10

Fusion Protein of LF Domain 1 and PA Domain 4

As PA Domain 4 is the immunodominant region of PA and is capable of conferring protection against anthrax when administered as a protein (Flick-Smith et al., 2002), and as LF Domain 1 is also able to confer protection (Example 4), the following fusion protein comprising Domain 1 of LF linked to Domain 4 of PA via a multiple cloning site has been generated:

LF Domain 1

(SEQ ID NO: 7)

AGGHGDVGMHVKEKEKNKDENKRKDEERNKTQEEHLKEIMKHIVKIEVKGEEAVK

KEAAEKLLEKVPSDVLEMYKAIGGKIYIVDGDITKHISLEALSEDKKKIKDIYGKDAL

-continued

LHEHYVYAKEGYEPVLVIQSSEDYVENTEKALNVYYEIGKILSRDILSKINQPYQKFL

DVLNTIKNASDSDGQDLLFTNQLKEHPTDFSVEFLEQNSNEVQEVFAKAFAYYIEPQ

HRDVLQLYAPEAFNYMDKFNEQEINL

Mutiple cloning site (SEQ ID NO: 8)

GAG CTC GGT ACC (SEQ ID NO: 27)

E L G T

PA Domain 4

(SEQ ID NO: 9)

TNIYTVLDKIKLNAKMNILIRDKRFHYDRNNIAVGADESVVKEAHREVINSSTEGLLL

NIDKDIRKILSGYIVEIEDTEGLKEVINDRYDMLNISSLRQDGKTFIDFKKYNDKLPLYI

SNPNYKVNVYAVTKENTIINPSENGDTSTNGIKKILIFSKKGYEIG

The amino acid sequence representing Domain 4 was extended at the N-terminal region to include a region of PA thought to bind a protective human toxin neutralizing monoclonal antibody called 2D3 (unpublished).

IKLNAKMNILIRDKRFHYDRN (SEQ ID NO: 10)

The original (SEQ ID NO: 11) and codon optimized (SEQ ID NO: 12) nucleotide sequences of the optimized region of the corresponding fusion protein, optimized for *Salmonella*, are shown in alignment in FIG. 24. FIG. 25 is a protein alignment of the optimized region of the LF Domain 1-PA Domain 4 fusion protein, aligning the original (SEQ ID NO: 13) and codon optimized (SEQ ID NO: 14) sequences. FIG. 26 is the full length optimized LF Domain 1-PA Domain 4 fusion protein (SEQ ID NO: 15).

The fusion protein was expressed using the QIAgen expression system and purified as described in the manual using a Nikel affinity column. The ability of the fusion protein to be recognized by rabbit polyclonal anti-PA and rabbit polyclonal anti-LF specific antisera was determined by Western blot (FIG. 27).

Example 11

Immunogenicity of LF Domain 1-PA Domain 4 Fusion Protein

The immunogenicity of the LF DOMAIN 1-PA DOMAIN 4 fusion protein was determined in mice as follows. Groups of 10 BALB/c mice were immunized i.m. on days 0 and 28 with 10 ug of each components (LFD1-PAD4 fusion, LFD1, PAD4, Control (PBS)) in combination with alum. Animals were tail bled on days-1, 13, 27, 56 and 72 and PA and F1 specific antibody responses were determined by ELISA. Results are set forth in FIG. 28.

As set forth in FIG. 28, the results show that the mice that received the LF1PAD4 fusion mount a comparable LF specific immune response to that seen in the mice which received only LFD1. This suggests that the addition of PAD4 as a 3' fusion has no adverse effect on the LF specific antibody response. The same appears to be true for the PA specific response.

Example 12

Fusion Protein of LF Domain 1 and Plague Vaccine Targets

Preliminary animal studies have confirmed the utility of the PA/LFn protein fusion approach set forth above for LcrV. Mice immunized with rPA in combination with rLFn-LcrV demonstrated a significantly higher antibody response to LcrV. It was also found that the orientation of the fusion protein was important, linking LFn to the C terminal of LcrV resulted in a significantly higher antibody response.

FIG. 29 demonstrates that LFn/V and V/LFn fusion proteins are immunogenic and elicit anti-LF and anti V serum IgG responses in BALB/c mice. Animals were immunized on days 0, 14 and 28. Data shown represented pooled samples at day 40.

Example 13

LcrV-MCS-LFR4-IQLF-PA2D3-PAD4loop/DR1-F1-L Fusion Protein

A LcrV-MCS-LFR4—IQLF-PA2D3-PAD4loop/DR1-F1-L fusion protein has been generated from the following component sequences:

LcrV—A vaccine candidate for plague (SEQ ID NO: 16)

MIRAYEQNPQHFIEDLEKVRVEQLTGHGSSVLEELVQLVKDKNIDISIKY

DPRKDSEVFANRVITDDIELLKKILAYFLPEDAILKGGHYDNQLQNGIKR

VKEFLESSPNTQWELRAFMAVMHFSLTADRIDDDILKVIVDSMNHHGDAR

SKLREELAELTAELKIYSVIQAEINKHLSSSGTINIHDKSINLMDKNLYG

YTDEEIFKASAEYKILEKMPQTTIQVDGSEKKIVSIKDFLGSENKRTGAL

GNLKNSYSYNKDNNELSHFATTCSDKSRPLNDLVSQKTTQLSDITSRFNS

AIEALNRFIQKYDSVMQRLLDDTSGK

MCS—multiple cloning site to enable the incorporation of additional protective epitopes

GCA TGC GAG CTC GGT ACC (SEQ ID NO: 17)

LFR4—a region of LF thought to contain a murine toxin neutralizing mAb antibody epitope (Lim et al., 2005)

DSLSEEEKELLNRIQVDSS (SEQ ID NO: 18)

IQLF—a region of LFn thought to bind a protective human toxin neutralizing monoclonal antibody (unpublished)

SDVLEMYKAIGGKIYIVDGDITKHISLEAL (SEQ ID NO: 19)

PA2D3—a region of PA though to bind a protective human toxin neutralizing monoclonal antibody (unpublished)

IKLNAKMNILIRDKRFHYDRN (SEQ ID NO: 20)

PAD4loop/DR1—the region encompassing the small loop of Domain 4 which is essential for binding of PA to its receptor. This region also contains part of the epitope recognized by the toxin neutralizing murine mAb 14B7 (Rosovitz et al., 2003). This region also contains an immunodominant DR1 T cell epitope (unpublished data)

KKYNDKLPLYISNPNYKVNVYA (SEQ ID NO: 21)

F1—a region of F1, the second plague vaccine candidate, thought to bind a protective animal monoclonal antibody (unpublished)

AADLTASTTATATLVEPARITLTYKEGAPITIM (SEQ ID NO: 22)

LFn—The protective N terminal domain of LF (see above)

(SEQ ID NO: 23)
AGGHGDVGMHVKEKEKNKDENKRKDEERNKTQEEHLKEIMKHIVKIEVKG
EEAVKKEAAEKLLEKVPSDVLEMYKAIGGKIYIVDGDITKHISLEALSED
KKKIKDIYGKDALLHEHYVYAKEGYEPVLVIQSSEDYVENTEKALNVYYE
IGKILSRDILSKINQPYQKFLDVLNTIKNASDSDGQDLLFTNQLKEHPTD
FSVEFLEQNSNEVQEVFAKAFAYYIEPQHRDVLQLYAPEAFNYMDKFNEQ
EINL

To determine the immunogenicity and protective efficacy of this fusion protein, the protein was codon optimized for *Salmonella* and synthesized by Genescript as a Hist tagged protein. The complete amino acid sequence (SEQ ID NO: 25) is shown in FIG. 32 and the *Salmonella* codon optimized gene sequence (SEQ ID NO: 24) is shown in FIG. 31. The protein was subsequently expressed from *E. coli* and the purified protein was analyzed by Western blot (FIG. 33) and used to immunize animals (Examples 14 and 15 below).

Example 14

Immunogenicity Study of LcrV-LFR4-IQLF-PA2D3-PAD4loop/DR1-F1-Lfn Fusion Protein

Groups of 10 BALB/c mice were immunized i.m. on days 0 and 28 with 10 ug of components (1) LFD 1, (2) PA, (3) LcrV-LFR4-IQLF-PA2D3-PAD4loop/DR1-F1-LFn and (4) Control (PBS) in combination with alum. Animals were tail bled on days-1, 13, 27, 42 and 56 and PA, LF, LcrV and F1 specific antibody responses were determined by ELISA and are set forth in FIG. 33.

The results show that the mice that received the LcrV.PA.F1.LFD1 fusion mounted a comparable LF specific immune response to that seen in the mice which received only LFD1 suggesting that the addition of the LcrV.PA.F1 as a 5' fusion has no adverse effect on the LF specific antibody response. The same was the case for the LcrV specific response. It is noted that failure to induce a PA and F1 specific response is not surprising, as the presentation of these epitopes was not optimized.

Example 15

Immunogenicity Study of LcrV-LFR4-IQLF-PA2D3-PAD4loop/DR1-F1-LFn Fusion Protein (2)

Groups of 12 A/J mice were immunized i.m. on days 0 and 14 with 10 ug of protein in combination with alhydrogel. Protein utilized was as follows:

1. rPA
2. rLrcV-LFn
3. rF1-LFn
4. rLcrV-LFR4-IQLF-PA2D3-PAD4loop/DR1-F1-LFn

Animals are tail bled to determine the magnitude of vaccine specific antibody responses and subjected to live agent aerosol challenge 3 weeks after the last vaccine dose. Such a challenge consists of a lethal aerosol challenge with *Y. pestis* strain GB at $1\times10^3$–$1\times10^4$ cfu/mouse.

Example 16

Immunogenicity in Mice

Mice vaccinated in accordance with vaccines discussed herein can be tested for immunogenicity by exposure to a lethal aerosol challenge with *B. anthracis* strain STI spores at approx $1\times10^4$ spore/mouse.

Example 17

Immunogenicity and Efficacy of *Salmonella* Expressing Both Pa and LFn

Since LF Domain 1 is protective against *B. anthracis*, co-expression of both PA and LF1 in *Salmonella* are evaluated. Initially, the LF protein is evaluated for expression in *Salmonella* alone. Thus, a synthetic LF Domain 1 gene (LFoN), codon-optimized for expression in *E. coli*, and the native LF Domain 1 gene (LFnN) have been cloned into pSEC10 and expression of LFnN and LFoN is demonstrated by Western blotting.

The immunogenicity of *Salmonella* construct expression LF Domain 1 is determined in the A/J mouse model following oral dosing with approximately $1\times10^9$ cfu $ml^{-1}$. Immunogenicity of each construct is measured by quantifying the specific IgG end-point titer for each group using an ELISA format. Subsequently, immunized mice are challenged with approximately $1\times10^5$ cfu (approximately 200 MLDs) of aerosolized *B. anthracis* STI spores and monitored for survival.

To determine the efficacy of a co-administration of PA and LFn two approaches are adopted. In the first mice are immunized with a combination of two *Salmonella* constructs expressing PA and LFn separately. Finally a construct is made expressing both PA and LFn.

Example 18

Immunogenicity and Efficacy of *Salmonella* Expressing Both Lcrv-PA-LFn

The Lcrv-PA-LFn fusion protein is cloned into the pSEC10 vector and expressed as ClyA fusion from *Salmonella*. The ability of this construct to confer protection against anthrax and plague is determined following oral dosing.

The immunogenicity of *Salmonella* constructs is determined in the A/J mouse model following oral dosing with approximately $1\times10^9$ cfu $ml^{-1}$. Immunogenicity of each construct is measured by quantifying the specific IgG end-point titer for each group using an ELISA format. Subsequently, immunized mice are challenged with either aerosolized anthrax (~$1\times10^5$ cfu) or plague ($1\times10^4$ cfu) and monitored for survival.

Although the invention has been described with reference to the above examples, it will be understood that modifications and variations are encompassed within the spirit and scope of the invention. Accordingly, the invention is limited only by the following claims.

What is claimed is:

1. A vaccine for the prevention of anthrax comprising a live, attenuated *Salmonella* comprising a nucleotide sequence encoding a fusion protein, wherein the nucleotide sequence comprises a sequence selected from the group consisting of SEQ ID NO: 11, SEQ ID NO: 12 and SEQ ID NO: 24.

2. A vaccine for the prevention of anthrax comprising a live, attenuated *Salmonella* comprising a nucleotide sequence encoding a fusion protein, wherein the fusion protein comprises a sequence selected from the group consisting of SEQ ID NO: 13, SEQ ID NO: 14, SEQ ID NO: 15, and SEQ ID NO: 25.

* * * * *

UNITED STATES PATENT AND TRADEMARK OFFICE

CERTIFICATE OF CORRECTION

PATENT NO. : 7,947,268 B2
APPLICATION NO. : 12/084998
DATED : May 24, 2011
INVENTOR(S) : Leslie W. J. Baillie It is certified that error appears in the above-identified patent and that said Letters Patent is hereby corrected as shown below:

Column 1, line 19: "Grant No. U19A1058578-01" should be -- Grant No. U19A1056578-01 --.

Signed and Sealed this
Sixteenth Day of August, 2011

David J. Kappos
*Director of the United States Patent and Trademark Office*

SEQUENCE LISTING

```
<160> NUMBER OF SEQ ID NOS: 27

<210> SEQ ID NO 1
<211> LENGTH: 2331
<212> TYPE: DNA
<213> ORGANISM: Bacillus anthracis

<400> SEQUENCE: 1

gcgggcggtc atggtgatgt aggtatgcac gtaaaagaga aagagaaaaa taaagatgag     60

aataagagaa aagatgaaga acgaaataaa acacaggaag agcatttaaa ggaaatcatg    120

aaacacattg taaaaataga agtaaaaggg gaggaagctg ttaaaaaaga ggcagcagaa    180

aagctacttg agaaagtacc atctgatgtt ttagagatgt ataaagcaat tggaggaaag    240

atatatattg tggatggtga tattacaaaa catatatctt tagaagcatt atctgaagat    300

aagaaaaaaa taaaagacat ttatgggaaa gatgctttat tacatgaaca ttatgtatat    360

gcaaaagaag gatatgaacc cgtacttgta atccaatctt cggaagatta tgtagaaaat    420

actgaaaagg cactgaacgt ttattatgaa ataggtaaga tattatcaag ggatatttta    480

agtaaaatta atcaaccata tcagaaattt ttagatgtat taaataccat taaaaatgca    540

tctgattcag atggacaaga tcttttattt actaatcagc ttaaggaaca tcccacagac    600

ttttctgtag aattcttgga acaaaatagc aatgaggtac aagaagtatt tgcgaaagct    660

tttgcatatt atatcgagcc acagcatcgt gatgttttac agctttatgc accggaagct    720

tttaattaca tggataaatt taacgaacaa gaaataaatc tatccttgga agaacttaaa    780

gatcaacgga tgctgtcaag atatgaaaaa tgggaaaaga taaaacagca ctatcaacac    840

tggagcgatt ctttatctga agaaggaaga ggacttttaa aaaagctgca gattcctatt    900

gagccaaaga aagatgacat aattcattct ttatctcaag aagaaaaaga gcttctaaaa    960

agaatacaaa ttgatagtag tgattttttta tctactgagg aaaaagagtt tttaaaaaag   1020

ctacaaattg atattcgtga ttctttatct gaagaagaaa aagagctttt aaatagaata   1080

caggtggata gtagtaatcc tttatctgaa aaagaaaaag agtttttaaa aaagctgaaa   1140

cttgatattc aaccatatga tattaatcaa aggttgcaag atacaggagg gttaattgat   1200

agtccgtcaa ttaatcttga tgtaagaaag cagtataaaa gggatattca aaatattgat   1260

gctttattac atcaatccat tggaagtacc ttgtacaata aaatttattt gtatgaaaat   1320

atgaatatca ataaccttac agcaacccta ggtgcggatt tagttgattc cactgataat   1380

actaaaatta atagaggtat tttcaatgaa ttcaaaaaaa atttcaaata tagtatttct   1440

agtaactata tgattgttga tataaatgaa aggcctgcat tagataatga gcgtttgaaa   1500

tggagaatcc aattatcacc agatactcga gcaggatatt tagaaaatgg aaagcttata   1560
```

-continued

```
ttacaaagaa acatcggtct ggaaataaag gatgtacaaa taattaagca atccgaaaaa   1620

gaatatataa ggattgatgc gaaagtagtg ccaaagagta aaatagatac aaaaattcaa   1680

gaagcacagt taaatataaa tcaggaatgg aataaagcat tagggttacc aaaatataca   1740

aagcttatta cattcaacgt gcataataga tatgcatcca atattgtaga aagtgcttat   1800

ttaatattga atgaatggaa aaataatatt caaagtgatc ttataaaaaa ggtaacaaat   1860

tacttagttg atggtaatgg aagatttgtt tttaccgata ttactctccc taatatagct   1920

gaacaatata cacatcaaga tgagatatat gagcaagttc attcaaaagg gttatatgtt   1980

ccagaatccc gttctatatt actccatgga ccttcaaaag gtgtagaatt aaggaatgat   2040

agtgagggtt ttatacacga atttggacat gctgtggatg attatgctgg atatctatta   2100

gataagaacc aatctgattt agttacaaat tctaaaaaat tcattgatat ttttaaggaa   2160

gaagggagta atttaacttc gtatgggaga acaaatgaag cggaattttt tgcagaagcc   2220

tttaggttaa tgcattctac ggaccatgct gaacgtttaa aagttcaaaa aaatgctccg   2280

aaaactttcc aatttattaa cgatcagatt aagttcatta ttaactcata a            2331
```

<210> SEQ ID NO 2
<211> LENGTH: 2331
<212> TYPE: DNA
<213> ORGANISM: Artificial Sequence
<220> FEATURE:
<223> OTHER INFORMATION: biologically inactive B. anthracis LF

<400> SEQUENCE: 2

```
gcgggcggtc atggtgatgt tggtatgcat gttaaagaga aagagaaaaa taaagatgag     60

aataaacgta aagatgaaga gcgtaataaa acccaggaag agcatctgaa agaaatcatg    120

aaacatattg ttaaaattga agttaaaggc gaggaagccg ttaaaaaaga ggcagccgaa    180

aaactgctgg agaaagttcc gagcgatgtt ctggagatgt ataaagcaat tggcggtaaa    240

atctatattg tggatggtga tattaccaaa catattagcc tggaagcact gagcgaagat    300

aagaagaaaa ttaaagacat ctatggcaaa gatgccctgc tgcatgaaca ttatgtttat    360

gcaaaagaag gctatgaacc ggttctggtt atccagagca gcgaagatta tgttgaaaat    420

accgaaaaag cactgaacgt ttattatgaa attggtaaaa ttctgagccg tgatattctg    480

agcaaaatta atcagccgta tcagaaattt ctggatgttc tgaataccat taaaaatgca    540

agcgatagcg atggccagga tctgctgttt accaatcagc tgaaagaaca tccgaccgac    600

tttagcgttg aatttctgga acagaatagc aatgaggttc aggaagtttt tgcgaaagcc    660

tttgcatatt atatcgagcc gcagcatcgt gatgttctgc agctgtatgc accggaagcc    720

tttaattata tggataagtt taacgaacag gaaattaatc tgagcctgga agagctgaaa    780

gatcagcgta tgctgagccg ttatgaaaaa tgggaaaaaa ttaaacagca ttatcagcat    840

tggagcgata gcctgagcga agagggccgt ggcctgctga aaaaactgca gattccgatt    900

gagccgaaaa aagatgacat tatccatagc ctgagccagg aagagaaaga gctgctgaaa    960

cgtattcaga ttgatagcag cgattttctg agcaccgagg aaaaagagtt tctgaaaaaa   1020

ctgcagattg atattcgtga tagcctgagc gaagaggaaa aagagctgct gaatcgtatt   1080

caggtggata gcagcaatcc gctgagcgaa aaagaaaaag agtttctgaa aaaactgaaa   1140

ctggatattc agccgtatga tattaatcag cgtctgcagg ataccggcgg tctgattgat   1200

agcccgagca ttaatctgga tgttcgtaaa cagtataaac gtgatattca gaatattgat   1260

gccctgctgc atcagagcat tggcagcacc ctgtataata aaatctatct gtatgaaaat   1320
```

-continued

```
atgaatatca ataacctgac cgcaaccctg ggtgcggatc tggttgatag caccgataat   1380

accaaaatta atcgtggtat ttttaatgag tttaagaaaa attttaaata tagcattagc   1440

agcaactata tgattgttga tattaatgaa cgtccggcac tggataatga gcgtctgaaa   1500

tggcgtatcc agctgagccc ggatacccgt gcaggctatc tggaaaatgg caaactgatt   1560

ctgcagcgta acatcggtct ggaaattaaa gatgttcaga ttatcaaaca gagcgaaaaa   1620

gaatatattc gtattgatgc gaaagttgtg ccgaaaagca aaattgatac caaaattcag   1680

gaagcacagc tgaatattaa tcaggaatgg aataaagcac tgggcctgcc gaaatatacc   1740

aaactgatta cctttaacgt gcataatcgt tatgcaagca atattgttga aagcgcctat   1800

ctgattctga atgaatggaa aaataacatt cagagcgatc tgattaaaaa agttaccaat   1860

tatctggttg atggtaatgg ccgttttgtt tttaccgata ttaccctgcc gaatattgcc   1920

gaacagtata cccatcagga tgagatctat gagcaggttc atagcaaagg cctgtatgtt   1980

ccggaaagcc gtagcattct gctgcatggc ccgagcaaag gtgttgaact gcgtaatgat   2040

agcgagggtt ttattcattg ttttggccat gccgtggatg actatgccgg ctatctgctg   2100

gataaaaacc agagcgatct ggttaccaat agcaaaaagt ttattgatat ttttaaagaa   2160

gagggcagca atctgaccag ctatggccgt accaatgaag cggaattctt tgcagaagcc   2220

tttcgtctga tgcatagcac cgaccatgcc gaacgtctga aagttcagaa aaatgccccg   2280

aaaacctttc agtttattaa cgatcagatt aagtttatta tcaacagcta a            2331

<210> SEQ ID NO 3
<211> LENGTH: 2351
<212> TYPE: DNA
<213> ORGANISM: Artificial Sequence
<220> FEATURE:
<223> OTHER INFORMATION: biologically inactive  B. anthracis LF

<400> SEQUENCE: 3

ccgaggatcc gcgggcggtc atggtgatgt tggtatgcat gttaaagaga aagagaaaaa     60

taaagatgag aataaacgta aagatgaaga gcgtaataaa acccaggaag agcatctgaa    120

agaaatcatg aaacatattg ttaaaattga agttaaaggc gaggaagccg ttaaaaaaga    180

ggcagccgaa aaactgctgg agaaagttcc gagcgatgtt ctggagatgt ataaagcaat    240

tggcggtaaa atctatattg tggatggtga tattaccaaa catattagcc tggaagcact    300

gagcgaagat aagaagaaaa ttaaagacat ctatggcaaa gatgccctgc tgcatgaaca    360

ttatgtttat gcaaaagaag gctatgaacc ggttctggtt atccagagca gcgaagatta    420

tgttgaaaat accgaaaaag cactgaacgt ttattatgaa attggtaaaa ttctgagccg    480

tgatattctg agcaaaatta atcagccgta tcagaaattt ctggatgttc tgaataccat    540

taaaaatgca agcgatagcg atggccagga tctgctgttt accaatcagc tgaaagaaca    600

tccgaccgac tttagcgttg aatttctgga acagaatagc aatgaggttc aggaagtttt    660

tgcgaaagcc tttgcatatt atatcgagcc gcagcatcgt gatgttctgc agctgtatgc    720

accggaagcc tttaattata tggataagtt taacgaacag gaaattaatc tgagcctgga    780

agagctgaaa gatcagcgta tgctgagccg ttatgaaaaa tgggaaaaaa ttaaacagca    840

ttatcagcat tggagcgata gcctgagcga agagggccgt ggcctgctga aaaaactgca    900

gattccgatt gagccgaaaa aagatgacat tatccatagc ctgagccagg aagagaaaga    960

gctgctgaaa cgtattcaga ttgatagcag cgattttctg agcaccgagg aaaaagagtt   1020

tctgaaaaaa ctgcagattg atattcgtga tagcctgagc gaagaggaaa aagagctgct   1080
```

```
gaatcgtatt caggtggata gcagcaatcc gctgagcgaa aaagaaaaag agtttctgaa   1140

aaaactgaaa ctggatattc agccgtatga tattaatcag cgtctgcagg ataccggcgg   1200

tctgattgat agcccgagca ttaatctgga tgttcgtaaa cagtataaac gtgatattca   1260

gaatattgat gccctgctgc atcagagcat tggcagcacc ctgtataata aaatctatct   1320

gtatgaaaat atgaatatca ataacctgac cgcaaccctg ggtgcggatc tggttgatag   1380

caccgataat accaaaatta atcgtggtat ttttaatgag tttaagaaaa attttaaata   1440

tagcattagc agcaactata tgattgttga tattaatgaa cgtccggcac tggataatga   1500

gcgtctgaaa tggcgtatcc agctgagccc ggatacccgt gcaggctatc tggaaaatgg   1560

caaactgatt ctgcagcgta acatcggtct ggaaattaaa gatgttcaga ttatcaaaca   1620

gagcgaaaaa gaatatattc gtattgatgc gaaagttgtg ccgaaaagca aaattgatac   1680

caaaattcag gaagcacagc tgaatattaa tcaggaatgg aataaagcac tgggcctgcc   1740

gaaatatacc aaactgatta cctttaacgt gcataatcgt tatgcaagca atattgttga   1800

aagcgcctat ctgattctga atgaatggaa aaataacatt cagagcgatc tgattaaaaa   1860

agttaccaat tatctggttg atggtaatgg ccgttttgtt tttaccgata ttaccctgcc   1920

gaatattgcc gaacagtata cccatcagga tgagatctat gagcaggttc atagcaaagg   1980

cctgtatgtt ccggaaagcc gtagcattct gctgcatggc ccgagcaaag gtgttgaact   2040

gcgtaatgat agcgagggtt ttattcattg ttttggccat gccgtggatg actatgccgg   2100

ctatctgctg gataaaaacc agagcgatct ggttaccaat agcaaaaagt ttattgatat   2160

ttttaaagaa gagggcagca atctgaccag ctatggccgt accaatgaag cggaattctt   2220

tgcagaagcc tttcgtctga tgcatagcac cgaccatgcc gaacgtctga aagttcagaa   2280

aaatgccccg aaaacctttc agtttattaa cgatcagatt aagtttatta tcaacagcta   2340

aaagctttcg g                                                        2351
```

<210> SEQ ID NO 4
<211> LENGTH: 776
<212> TYPE: PRT
<213> ORGANISM: Bacillus anthracis

<400> SEQUENCE: 4

```
Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140
```

-continued

```
Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
            260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
    290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
            340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
    370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415

Gln Asn Ile Asp Ala Leu Leu His Gln Ser Ile Gly Ser Thr Leu Tyr
            420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
    450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
            500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
    530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575
```

```
Pro Lys Tyr Thr Lys Leu Ile Thr Phe Asn Val His Asn Arg Tyr Ala
            580                 585                 590

Ser Asn Ile Val Glu Ser Ala Tyr Leu Ile Leu Asn Glu Trp Lys Asn
        595                 600                 605

Asn Ile Gln Ser Asp Leu Ile Lys Lys Val Thr Asn Tyr Leu Val Asp
    610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
                645                 650                 655

Gly Leu Tyr Val Pro Glu Ser Arg Ser Ile Leu Leu His Gly Pro Ser
            660                 665                 670

Lys Gly Val Glu Leu Arg Asn Asp Ser Glu Gly Phe Ile His Glu Phe
        675                 680                 685

Gly His Ala Val Asp Asp Tyr Ala Gly Tyr Leu Leu Asp Lys Asn Gln
    690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
                725                 730                 735

Phe Ala Glu Ala Phe Arg Leu Met His Ser Thr Asp His Ala Glu Arg
            740                 745                 750

Leu Lys Val Gln Lys Asn Ala Pro Lys Thr Phe Gln Phe Ile Asn Asp
        755                 760                 765

Gln Ile Lys Phe Ile Ile Asn Ser
    770                 775


<210> SEQ ID NO 5
<211> LENGTH: 776
<212> TYPE: PRT
<213> ORGANISM: Artificial Sequence
<220> FEATURE:
<223> OTHER INFORMATION: biologically inactive LF of B. anthracis

<400> SEQUENCE: 5

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160
```

-continued

```
Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
            260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
    290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
            340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
    370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415

Gln Asn Ile Asp Ala Leu Leu His Gln Ser Ile Gly Ser Thr Leu Tyr
            420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
    450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
            500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
    530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575

Pro Lys Tyr Thr Lys Leu Ile Thr Phe Asn Val His Asn Arg Tyr Ala
            580                 585                 590
```

```
Ser Asn Ile Val Glu Ser Ala Tyr Leu Ile Leu Asn Glu Trp Lys Asn
        595                 600                 605

Asn Ile Gln Ser Asp Leu Ile Lys Lys Val Thr Asn Tyr Leu Val Asp
    610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
                645                 650                 655

Gly Leu Tyr Val Pro Glu Ser Arg Ser Ile Leu Leu His Gly Pro Ser
            660                 665                 670

Lys Gly Val Glu Leu Arg Asn Asp Ser Glu Gly Phe Ile His Cys Phe
        675                 680                 685

Gly His Ala Val Asp Asp Tyr Ala Gly Tyr Leu Leu Asp Lys Asn Gln
    690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
                725                 730                 735

Phe Ala Glu Ala Phe Arg Leu Met His Ser Thr Asp His Ala Glu Arg
            740                 745                 750

Leu Lys Val Gln Lys Asn Ala Pro Lys Thr Phe Gln Phe Ile Asn Asp
        755                 760                 765

Gln Ile Lys Phe Ile Ile Asn Ser
    770                 775


<210> SEQ ID NO 6
<211> LENGTH: 30
<212> TYPE: PRT
<213> ORGANISM: Bacillus anthracis

<400> SEQUENCE: 6

Ser Asp Val Leu Glu Met Tyr Lys Ala Ile Gly Gly Lys Ile Tyr Ile
1               5                   10                  15

Val Asp Gly Asp Ile Thr Lys His Ile Ser Leu Glu Ala Leu
            20                  25                  30


<210> SEQ ID NO 7
<211> LENGTH: 254
<212> TYPE: PRT
<213> ORGANISM: Bacillus anthracis

<400> SEQUENCE: 7

Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110
```

```
Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu
                245                 250


<210> SEQ ID NO 8
<211> LENGTH: 12
<212> TYPE: DNA
<213> ORGANISM: Bacillus anthracis

<400> SEQUENCE: 8

gagctcggta cc                                                          12


<210> SEQ ID NO 9
<211> LENGTH: 164
<212> TYPE: PRT
<213> ORGANISM: Bacillus anthracis

<400> SEQUENCE: 9

Thr Asn Ile Tyr Thr Val Leu Asp Lys Ile Lys Leu Asn Ala Lys Met
1               5                   10                  15

Asn Ile Leu Ile Arg Asp Lys Arg Phe His Tyr Asp Arg Asn Asn Ile
            20                  25                  30

Ala Val Gly Ala Asp Glu Ser Val Val Lys Glu Ala His Arg Glu Val
        35                  40                  45

Ile Asn Ser Ser Thr Glu Gly Leu Leu Leu Asn Ile Asp Lys Asp Ile
    50                  55                  60

Arg Lys Ile Leu Ser Gly Tyr Ile Val Glu Ile Glu Asp Thr Glu Gly
65                  70                  75                  80

Leu Lys Glu Val Ile Asn Asp Arg Tyr Asp Met Leu Asn Ile Ser Ser
                85                  90                  95

Leu Arg Gln Asp Gly Lys Thr Phe Ile Asp Phe Lys Lys Tyr Asn Asp
            100                 105                 110

Lys Leu Pro Leu Tyr Ile Ser Asn Pro Asn Tyr Lys Val Asn Val Tyr
        115                 120                 125

Ala Val Thr Lys Glu Asn Thr Ile Ile Asn Pro Ser Glu Asn Gly Asp
    130                 135                 140

Thr Ser Thr Asn Gly Ile Lys Lys Ile Leu Ile Phe Ser Lys Lys Gly
145                 150                 155                 160

Tyr Glu Ile Gly


<210> SEQ ID NO 10
<211> LENGTH: 21
```

<212> TYPE: PRT
<213> ORGANISM: Bacillus anthracis

<400> SEQUENCE: 10

Ile Lys Leu Asn Ala Lys Met Asn Ile Leu Ile Arg Asp Lys Arg Phe
1 5 10 15

His Tyr Asp Arg Asn
20

<210> SEQ ID NO 11
<211> LENGTH: 1272
<212> TYPE: DNA
<213> ORGANISM: Artificial Sequence
<220> FEATURE:
<223> OTHER INFORMATION: LF1-PA4 fusion protein nucleotide sequence

<400> SEQUENCE: 11
gcgggcggtc atggtgatgt tggtatgcat gttaaagaga aagagaaaaa taaagatgag 60
aataaacgta aagatgaaga gcgtaataaa acccaggaag agcatctgaa agaaatcatg 120
aaacatattg ttaaaattga agttaaaggc gaggaagccg ttaaaaaaga ggcagccgaa 180
aaactgctgg agaaagttcc gagcgatgtt ctggagatgt ataaagcaat tggcggtaaa 240
atctatattg tggatggtga tattaccaaa catattagcc tggaagcact gagcgaagat 300
aagaagaaaa ttaaagacat ctatggcaaa gatgccctgc tgcatgaaca ttatgtttat 360
gcaaaagaag gctatgaacc ggttctggtt atccagagca gcgaagatta tgttgaaaat 420
accgaaaaag cactgaacgt ttattatgaa attggtaaaa ttctgagccg tgatattctg 480
agcaaaatta atcagccgta tcagaaattt ctggatgttc tgaataccat taaaaatgca 540
agcgatagcg atggccagga tctgctgttt accaatcagc tgaaagaaca tccgaccgac 600
tttagcgttg aatttctgga acagaatagc aatgaggttc aggaagtttt tgcgaaagcc 660
tttgcatatt atatcgagcc gcagcatcgt gatgttctgc agctgtatgc accggaagcc 720
tttaattata tggataagtt taacgaacag gaaattaatc tgagcgagct cggtaccacc 780
aatatctata cggtactcga caagatcaaa ctgaacgcga aaatgaacat tctgattcgc 840
gacaaacgtt tccactacga tcgtaataac atcgctgttg gcgctgatga atctgttgtg 900
aaagaagcgc atcgcgaagt catcaactcc agcaccgaag gcctgcttct gaacatcgac 960
aaagacattc gtaagatcct gtctggttac attgttgaga tcgaagacac cgaaggcctg 1020
aaagaagtga tcaatgatcg ttacgacatg ctgaacatca gctctctgcg tcaagatggt 1080
aagacgttca ttgacttcaa gaaatacaac gacaaacttc cgctgtatat ctctaatccg 1140
aactacaaag tgaacgttta cgctgttacc aaagagaaca ccatcatcaa tccatctgag 1200
aacggcgata cctctaccaa cggtatcaag aagattctga tcttctccaa gaaaggttac 1260
gagatcggtt aa 1272

<210> SEQ ID NO 12
<211> LENGTH: 1272
<212> TYPE: DNA
<213> ORGANISM: Artificial Sequence
<220> FEATURE:
<223> OTHER INFORMATION: LF1-PA4 fusion protein nucleotide sequence
optimized

<400> SEQUENCE: 12
gctggtggtc atggtgatgt tggtatgcat gttaaagaaa aagaaaaaaa caaagatgaa 60
aacaaacgta aagatgaaga acgtaacaaa acccaggaag aacatctgaa agaaattatg 120

-continued

```
aaacatattg ttaaaattga agttaaaggt gaagaagcgg ttaaaaaaga agcggcggaa    180

aaactgctgg aaaaagttcc gtctgatgtt ctggaaatgt ataaagcgat tggtggtaaa    240

atttatattg ttgatggtga tattactaaa catatctctc tggaagcgct gtctgaagat    300

aaaaaaaaaa tcaaagatat ctatggtaaa gatgcgctgc tgcatgaaca ttatgtttat    360

gcgaaagaag gttatgaacc ggttctggtt attcagtctt ctgaagatta tgttgaaaac    420

actgaaaaag ctctgaacgt ttattatgaa attggtaaaa ttctgtctcg tgatattctg    480

tctaaaatta accagccgta tcagaaattt ctggatgttc tgaacactat taaaaacgcg    540

tctgattctg atggtcagga tctgctgttt accaaccagc tgaaagaaca tccgaccgat    600

ttttctgttg aatttctgga acagaactct aacgaagttc aggaagtttt tgctaaagcg    660

tttgcgtatt atattgaacc gcagcatcgt gatgttctgc agctgtatgc tccggaagcg    720

tttaactata tggataaatt taacgaacag gaaattaacc tgtctgaact gggtactact    780

aacatttata ccgttctgga taaaattaaa ctgaacgcta aatgaacat tctgattcgt    840

gataaacgtt ttcattatga tcgtaacaac atcgctgttg gtgctgatga atctgttgtt    900

aaagaagcgc atcgtgaagt tattaactct tctaccgaag gtctgctgct gaacattgat    960

aaagatattc gtaaaattct gtctggttat attgttgaaa ttgaagatac tgaaggtctg   1020

aaagaagtta tcaacgatcg ttatgatatg ctgaacattt cttctctgcg tcaggatggt   1080

aaaacettta tcgattttaa aaaatataac gataaactgc cgctgtatat ctctaacccg   1140

aactataaag ttaacgttta tgcggttacc aaagaaaaca ctattattaa cccgtctgaa   1200

aacggtgata cctctactaa cggtatcaaa aaaatcctga tttttctaa aaaaggttat   1260

gaaattggtt aa                                                       1272
```

<210> SEQ ID NO 13
<211> LENGTH: 423
<212> TYPE: PRT
<213> ORGANISM: Artificial Sequence
<220> FEATURE:
<223> OTHER INFORMATION: LF1 - PA4 fusion protein

<400> SEQUENCE: 13

```
Ala Gly Gly His Gly Asp Val Gly Met His Val Lys Glu Lys Glu Lys
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160
```

Ser Lys Ile Asn Gln Pro Tyr Gln Lys Phe Leu Asp Val Leu Asn Thr
165 170 175

Ile Lys Asn Ala Ser Asp Ser Asp Gly Gln Asp Leu Leu Phe Thr Asn
180 185 190

Gln Leu Lys Glu His Pro Thr Asp Phe Ser Val Glu Phe Leu Glu Gln
195 200 205

Asn Ser Asn Glu Val Gln Glu Val Phe Ala Lys Ala Phe Ala Tyr Tyr
210 215 220

Ile Glu Pro Gln His Arg Asp Val Leu Gln Leu Tyr Ala Pro Glu Ala
225 230 235 240

Phe Asn Tyr Met Asp Lys Phe Asn Glu Gln Glu Ile Asn Leu Ser Glu
245 250 255

Leu Gly Thr Thr Asn Ile Tyr Thr Val Leu Asp Lys Ile Lys Leu Asn
260 265 270

Ala Lys Met Asn Ile Leu Ile Arg Asp Lys Arg Phe His Tyr Asp Arg
275 280 285

Asn Asn Ile Ala Val Gly Ala Asp Glu Ser Val Val Lys Glu Ala His
290 295 300

Arg Glu Val Ile Asn Ser Ser Thr Glu Gly Leu Leu Leu Asn Ile Asp
305 310 315 320

Lys Asp Ile Arg Lys Ile Leu Ser Gly Tyr Ile Val Glu Ile Glu Asp
325 330 335

Thr Glu Gly Leu Lys Glu Val Ile Asn Asp Arg Tyr Asp Met Leu Asn
340 345 350

Ile Ser Ser Leu Arg Gln Asp Gly Lys Thr Phe Ile Asp Phe Lys Lys
355 360 365

Tyr Asn Asp Lys Leu Pro Leu Tyr Ile Ser Asn Pro Asn Tyr Lys Val
370 375 380

Asn Val Tyr Ala Val Thr Lys Glu Asn Thr Ile Ile Asn Pro Ser Glu
385 390 395 400

Asn Gly Asp Thr Ser Thr Asn Gly Ile Lys Lys Ile Leu Ile Phe Ser
405 410 415

Lys Lys Gly Tyr Glu Ile Gly
420

<210> SEQ ID NO 14
<211> LENGTH: 423
<212> TYPE: PRT
<213> ORGANISM: Artificial Sequence
<220> FEATURE:
<223> OTHER INFORMATION: LF1 - PA4 fusion protein, optimized

<400> SEQUENCE: 14

Ala Gly Gly His Gly Asp Val Gly Met His Val Lys Glu Lys Glu Lys
1 5 10 15

Asn Lys Asp Glu Asn Lys Arg Lys Asp Glu Glu Arg Asn Lys Thr Gln
20 25 30

Glu Glu His Leu Lys Glu Ile Met Lys His Ile Val Lys Ile Glu Val
35 40 45

Lys Gly Glu Glu Ala Val Lys Lys Glu Ala Ala Glu Lys Leu Leu Glu
50 55 60

Lys Val Pro Ser Asp Val Leu Glu Met Tyr Lys Ala Ile Gly Gly Lys
65 70 75 80

Ile Tyr Ile Val Asp Gly Asp Ile Thr Lys His Ile Ser Leu Glu Ala
85 90 95

Leu Ser Glu Asp Lys Lys Lys Ile Lys Asp Ile Tyr Gly Lys Asp Ala

-continued

```
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Glu
                245                 250                 255

Leu Gly Thr Thr Asn Ile Tyr Thr Val Leu Asp Lys Ile Lys Leu Asn
            260                 265                 270

Ala Lys Met Asn Ile Leu Ile Arg Asp Lys Arg Phe His Tyr Asp Arg
        275                 280                 285

Asn Asn Ile Ala Val Gly Ala Asp Glu Ser Val Val Lys Glu Ala His
    290                 295                 300

Arg Glu Val Ile Asn Ser Ser Thr Glu Gly Leu Leu Leu Asn Ile Asp
305                 310                 315                 320

Lys Asp Ile Arg Lys Ile Leu Ser Gly Tyr Ile Val Glu Ile Glu Asp
                325                 330                 335

Thr Glu Gly Leu Lys Glu Val Ile Asn Asp Arg Tyr Asp Met Leu Asn
            340                 345                 350

Ile Ser Ser Leu Arg Gln Asp Gly Lys Thr Phe Ile Asp Phe Lys Lys
        355                 360                 365

Tyr Asn Asp Lys Leu Pro Leu Tyr Ile Ser Asn Pro Asn Tyr Lys Val
    370                 375                 380

Asn Val Tyr Ala Val Thr Lys Glu Asn Thr Ile Ile Asn Pro Ser Glu
385                 390                 395                 400

Asn Gly Asp Thr Ser Thr Asn Gly Ile Lys Lys Ile Leu Ile Phe Ser
                405                 410                 415

Lys Lys Gly Tyr Glu Ile Gly
            420
```

<210> SEQ ID NO 15
<211> LENGTH: 1284
<212> TYPE: PRT
<213> ORGANISM: Artificial Sequence
<220> FEATURE:
<223> OTHER INFORMATION: LF1 - PA4 fusion protein nucleotide sequence, optimized

<400> SEQUENCE: 15

```
Gly Gly Ala Thr Cys Cys Gly Cys Thr Gly Gly Thr Gly Gly Thr Cys
1               5                   10                  15

Ala Thr Gly Gly Thr Gly Ala Thr Gly Thr Thr Gly Gly Thr Ala Thr
            20                  25                  30

Gly Cys Ala Thr Gly Thr Thr Ala Ala Ala Gly Ala Ala Ala Ala Ala
```

-continued

```
        35                  40                  45

Gly Ala Ala Ala Ala Ala Ala Ala Cys Ala Ala Ala Gly Ala Thr Gly
    50                  55                  60

Ala Ala Ala Ala Cys Ala Ala Ala Cys Gly Thr Ala Ala Ala Gly Ala
65                  70                  75                  80

Thr Gly Ala Ala Gly Ala Ala Cys Gly Thr Ala Ala Cys Ala Ala Ala
                85                  90                  95

Ala Cys Cys Cys Ala Gly Gly Ala Ala Gly Ala Ala Cys Ala Thr Cys
            100                 105                 110

Thr Gly Ala Ala Ala Gly Ala Ala Ala Thr Thr Ala Thr Gly Ala Ala
        115                 120                 125

Ala Cys Ala Thr Ala Thr Thr Gly Thr Thr Ala Ala Ala Ala Thr Thr
    130                 135                 140

Gly Ala Ala Gly Thr Thr Ala Ala Ala Gly Gly Thr Gly Ala Ala Gly
145                 150                 155                 160

Ala Ala Gly Cys Gly Gly Thr Thr Ala Ala Ala Ala Ala Ala Gly Ala
                165                 170                 175

Ala Gly Cys Gly Gly Cys Gly Gly Ala Ala Ala Ala Ala Cys Thr Gly
            180                 185                 190

Cys Thr Gly Gly Ala Ala Ala Ala Ala Gly Thr Thr Cys Cys Gly Thr
        195                 200                 205

Cys Thr Gly Ala Thr Gly Thr Thr Cys Thr Gly Gly Ala Ala Ala Thr
    210                 215                 220

Gly Thr Ala Thr Ala Ala Ala Gly Cys Gly Ala Thr Thr Gly Gly Thr
225                 230                 235                 240

Gly Gly Thr Ala Ala Ala Ala Thr Thr Thr Ala Thr Ala Thr Thr Gly
                245                 250                 255

Thr Thr Gly Ala Thr Gly Gly Thr Gly Ala Thr Ala Thr Thr Ala Cys
            260                 265                 270

Thr Ala Ala Ala Cys Ala Thr Ala Thr Cys Thr Cys Thr Cys Thr Gly
        275                 280                 285

Gly Ala Ala Gly Cys Gly Cys Thr Gly Thr Cys Thr Gly Ala Ala Gly
    290                 295                 300

Ala Thr Ala Ala Ala Ala Ala Ala Ala Ala Ala Ala Thr Cys Ala Ala
305                 310                 315                 320

Ala Gly Ala Thr Ala Thr Cys Thr Ala Thr Gly Gly Thr Ala Ala Ala
                325                 330                 335

Gly Ala Thr Gly Cys Gly Cys Thr Gly Cys Thr Gly Cys Ala Thr Gly
            340                 345                 350

Ala Ala Cys Ala Thr Thr Ala Thr Gly Thr Thr Thr Ala Thr Gly Cys
        355                 360                 365

Gly Ala Ala Ala Gly Ala Ala Gly Gly Thr Thr Ala Thr Gly Ala Ala
    370                 375                 380

Cys Cys Gly Gly Thr Thr Cys Thr Gly Gly Thr Thr Ala Thr Thr Cys
385                 390                 395                 400

Ala Gly Thr Cys Thr Thr Cys Thr Gly Ala Ala Gly Ala Thr Thr Ala
                405                 410                 415

Thr Gly Thr Thr Gly Ala Ala Ala Ala Cys Ala Cys Thr Gly Ala Ala
            420                 425                 430

Ala Ala Ala Gly Cys Thr Cys Thr Gly Ala Ala Cys Gly Thr Thr Thr
        435                 440                 445

Ala Thr Thr Ala Thr Gly Ala Ala Ala Thr Thr Gly Gly Thr Ala Ala
    450                 455                 460
```

-continued

```
Ala Ala Thr Thr Cys Thr Gly Thr Cys Thr Cys Gly Thr Gly Ala Thr
465                 470                 475                 480

Ala Thr Thr Cys Thr Gly Thr Cys Thr Ala Ala Ala Ala Thr Thr Ala
                485                 490                 495

Ala Cys Cys Ala Gly Cys Cys Gly Thr Ala Thr Cys Ala Gly Ala Ala
            500                 505                 510

Ala Thr Thr Thr Cys Thr Gly Gly Ala Thr Gly Thr Thr Cys Thr Gly
        515                 520                 525

Ala Ala Cys Ala Cys Thr Ala Thr Thr Ala Ala Ala Ala Ala Cys Gly
    530                 535                 540

Cys Gly Thr Cys Thr Gly Ala Thr Thr Cys Thr Gly Ala Thr Gly Gly
545                 550                 555                 560

Thr Cys Ala Gly Gly Ala Thr Cys Thr Gly Cys Thr Gly Thr Thr Thr
                565                 570                 575

Ala Cys Cys Ala Ala Cys Cys Ala Gly Cys Thr Gly Ala Ala Ala Gly
            580                 585                 590

Ala Ala Cys Ala Thr Cys Cys Gly Ala Cys Cys Gly Ala Thr Thr Thr
        595                 600                 605

Thr Thr Cys Thr Gly Thr Thr Gly Ala Ala Thr Thr Thr Cys Thr Gly
    610                 615                 620

Gly Ala Ala Cys Ala Gly Ala Ala Cys Thr Cys Thr Ala Ala Cys Gly
625                 630                 635                 640

Ala Ala Gly Thr Thr Cys Ala Gly Gly Ala Ala Gly Thr Thr Thr Thr
                645                 650                 655

Thr Gly Cys Thr Ala Ala Ala Gly Cys Gly Thr Thr Thr Gly Cys Gly
            660                 665                 670

Thr Ala Thr Thr Ala Thr Ala Thr Thr Gly Ala Ala Cys Cys Gly Cys
        675                 680                 685

Ala Gly Cys Ala Thr Cys Gly Thr Gly Ala Thr Gly Thr Thr Cys Thr
    690                 695                 700

Gly Cys Ala Gly Cys Thr Gly Thr Ala Thr Gly Cys Thr Cys Cys Gly
705                 710                 715                 720

Gly Ala Ala Gly Cys Gly Thr Thr Thr Ala Ala Cys Thr Ala Thr Ala
                725                 730                 735

Thr Gly Gly Ala Thr Ala Ala Ala Thr Thr Thr Ala Ala Cys Gly Ala
            740                 745                 750

Ala Cys Ala Gly Gly Ala Ala Ala Thr Thr Ala Ala Cys Cys Thr Gly
        755                 760                 765

Thr Cys Thr Gly Ala Ala Cys Thr Gly Gly Gly Thr Ala Cys Thr Ala
    770                 775                 780

Cys Thr Ala Ala Cys Ala Thr Thr Thr Ala Thr Ala Cys Cys Gly Thr
785                 790                 795                 800

Thr Cys Thr Gly Gly Ala Thr Ala Ala Ala Ala Thr Thr Ala Ala Ala
                805                 810                 815

Cys Thr Gly Ala Ala Cys Gly Cys Thr Ala Ala Ala Ala Thr Gly Ala
            820                 825                 830

Ala Cys Ala Thr Thr Cys Thr Gly Ala Thr Thr Cys Gly Thr Gly Ala
        835                 840                 845

Thr Ala Ala Ala Cys Gly Thr Thr Thr Thr Cys Ala Thr Thr Ala Thr
    850                 855                 860

Gly Ala Thr Cys Gly Thr Ala Ala Cys Ala Ala Cys Ala Thr Cys Gly
865                 870                 875                 880

Cys Thr Gly Thr Thr Gly Gly Thr Gly Cys Thr Gly Ala Thr Gly Ala
                885                 890                 895
```

-continued

```
Ala Thr Cys Thr Gly Thr Thr Gly Thr Thr Ala Ala Ala Gly Ala Ala
            900                 905                 910

Gly Cys Gly Cys Ala Thr Cys Gly Thr Gly Ala Ala Gly Thr Thr Ala
        915                 920                 925

Thr Thr Ala Ala Cys Thr Cys Thr Thr Cys Thr Ala Cys Cys Gly Ala
    930                 935                 940

Ala Gly Gly Thr Cys Thr Gly Cys Thr Gly Cys Thr Gly Ala Ala Cys
945                 950                 955                 960

Ala Thr Thr Gly Ala Thr Ala Ala Ala Gly Ala Thr Ala Thr Thr Cys
                965                 970                 975

Gly Thr Ala Ala Ala Ala Thr Thr Cys Thr Gly Thr Cys Thr Gly Gly
            980                 985                 990

Thr Thr Ala Thr Ala Thr Thr Gly  Thr Thr Gly Ala Ala  Ala Thr Thr
        995                 1000                1005

Gly Ala  Ala Gly Ala Thr Ala  Cys Thr Gly Ala Ala  Gly Gly Thr
    1010                 1015                 1020

Cys Thr  Gly Ala Ala Ala Gly  Ala Ala Gly Thr Thr  Ala Thr Cys
    1025                 1030                 1035

Ala Ala  Cys Gly Ala Thr Cys  Gly Thr Thr Ala Thr  Gly Ala Thr
    1040                 1045                 1050

Ala Thr  Gly Cys Thr Gly Ala  Ala Cys Ala Thr Thr  Thr Cys Thr
    1055                 1060                 1065

Thr Cys  Thr Cys Thr Gly Cys  Gly Thr Cys Ala Gly  Gly Ala Thr
    1070                 1075                 1080

Gly Gly  Thr Ala Ala Ala Ala  Cys Cys Thr Thr Thr  Ala Thr Cys
    1085                 1090                 1095

Gly Ala  Thr Thr Thr Thr Ala  Ala Ala Ala Ala Ala  Thr Ala Thr
    1100                 1105                 1110

Ala Ala  Cys Gly Ala Thr Ala  Ala Ala Cys Thr Gly  Cys Cys Gly
    1115                 1120                 1125

Cys Thr  Gly Thr Ala Thr Ala  Thr Cys Thr Cys Thr  Ala Ala Cys
    1130                 1135                 1140

Cys Cys  Gly Ala Ala Cys Thr  Ala Thr Ala Ala Ala  Gly Thr Thr
    1145                 1150                 1155

Ala Ala  Cys Gly Thr Thr Thr  Ala Thr Gly Cys Gly  Gly Thr Thr
    1160                 1165                 1170

Ala Cys  Cys Ala Ala Ala Gly  Ala Ala Ala Ala Cys  Ala Cys Thr
    1175                 1180                 1185

Ala Thr  Thr Ala Thr Thr Ala  Ala Cys Cys Cys Gly  Thr Cys Thr
    1190                 1195                 1200

Gly Ala  Ala Ala Ala Cys Gly  Gly Thr Gly Ala Thr  Ala Cys Cys
    1205                 1210                 1215

Thr Cys  Thr Ala Cys Thr Ala  Ala Cys Gly Gly Thr  Ala Thr Cys
    1220                 1225                 1230

Ala Ala  Ala Ala Ala Ala Ala  Thr Cys Cys Thr Gly  Ala Thr Thr
    1235                 1240                 1245

Thr Thr  Thr Thr Cys Thr Ala  Ala Ala Ala Ala Ala  Gly Gly Thr
    1250                 1255                 1260

Thr Ala  Thr Gly Ala Ala Ala  Thr Thr Gly Gly Thr  Thr Ala Ala
    1265                 1270                 1275

Ala Ala  Gly Cys Thr Thr
    1280
```

<210> SEQ ID NO 16
<211> LENGTH: 326
<212> TYPE: PRT
<213> ORGANISM: Yersinia pestis

<400> SEQUENCE: 16

```
Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325
```

<210> SEQ ID NO 17
<211> LENGTH: 18
<212> TYPE: DNA
<213> ORGANISM: Bacillus anthracis

<400> SEQUENCE: 17

```
gcatgcgagc tcggtacc                                                   18
```

<210> SEQ ID NO 18
<211> LENGTH: 19
<212> TYPE: PRT
<213> ORGANISM: Bacillus anthracis

<400> SEQUENCE: 18

Asp Ser Leu Ser Glu Glu Glu Lys Glu Leu Leu Asn Arg Ile Gln Val
1 5 10 15

Asp Ser Ser

<210> SEQ ID NO 19
<211> LENGTH: 30
<212> TYPE: PRT
<213> ORGANISM: Bacillus anthracis

<400> SEQUENCE: 19

Ser Asp Val Leu Glu Met Tyr Lys Ala Ile Gly Gly Lys Ile Tyr Ile
1 5 10 15

Val Asp Gly Asp Ile Thr Lys His Ile Ser Leu Glu Ala Leu
20 25 30

<210> SEQ ID NO 20
<211> LENGTH: 21
<212> TYPE: PRT
<213> ORGANISM: Bacillus anthracis

<400> SEQUENCE: 20

Ile Lys Leu Asn Ala Lys Met Asn Ile Leu Ile Arg Asp Lys Arg Phe
1 5 10 15

His Tyr Asp Arg Asn
20

<210> SEQ ID NO 21
<211> LENGTH: 22
<212> TYPE: PRT
<213> ORGANISM: Bacillus anthracis

<400> SEQUENCE: 21

Lys Lys Tyr Asn Asp Lys Leu Pro Leu Tyr Ile Ser Asn Pro Asn Tyr
1 5 10 15

Lys Val Asn Val Tyr Ala
20

<210> SEQ ID NO 22
<211> LENGTH: 33
<212> TYPE: PRT
<213> ORGANISM: Yersinia pestis

<400> SEQUENCE: 22

Ala Ala Asp Leu Thr Ala Ser Thr Thr Ala Thr Ala Thr Leu Val Glu
1 5 10 15

Pro Ala Arg Ile Thr Leu Thr Tyr Lys Glu Gly Ala Pro Ile Thr Ile
20 25 30

Met

<210> SEQ ID NO 23
<211> LENGTH: 254
<212> TYPE: PRT
<213> ORGANISM: Bacillus anthracis

<400> SEQUENCE: 23

Ala Gly Gly His Gly Asp Val Gly Met His Val Lys Glu Lys Glu Lys

-continued

```
1               5                   10                  15

Asn Lys Asp Glu Asn Lys Arg Lys Asp Glu Glu Arg Asn Lys Thr Gln
            20                  25                  30

Glu Glu His Leu Lys Glu Ile Met Lys His Ile Val Lys Ile Glu Val
        35                  40                  45

Lys Gly Glu Glu Ala Val Lys Lys Glu Ala Ala Glu Lys Leu Leu Glu
    50                  55                  60

Lys Val Pro Ser Asp Val Leu Glu Met Tyr Lys Ala Ile Gly Gly Lys
65                  70                  75                  80

Ile Tyr Ile Val Asp Gly Asp Ile Thr Lys His Ile Ser Leu Glu Ala
                85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu
                245                 250
```

<210> SEQ ID NO 24
<211> LENGTH: 2172
<212> TYPE: DNA
<213> ORGANISM: Artificial Sequence
<220> FEATURE:
<223> OTHER INFORMATION: LcrV-PA-F1-LFD1 fusion protein nucleotide sequence

<400> SEQUENCE: 24

```
atgagaggat cgcatcacca tcaccatcac ggatccatga ttagagccta cgaacaaaac      60

ccacaacatt ttattgagga tctagaaaaa gttagggtgg aacaacttac tggtcatggt     120

tcttcagttt tagaagaatt ggttcagtta gtcaaagata aaaatataga tatttccatt     180

aaatatgatc ccagaaaaga ttcggaggtt tttgccaata gagtaattac tgatgatatc     240

gaattgctca agaaaatcct agcttatttt ctacccgagg atgccattct taaaggcggt     300

cattatgaca accaactgca aaatggcatc aagcgagtaa aagagttcct tgaatcatcg     360

ccgaatacac aatgggaatt gcgggcgttc atggcagtaa tgcatttctc tttaaccgcc     420

gatcgtatcg atgatgatat tttgaaagtg attgttgatt caatgaatca tcatggtgat     480

gcccgtagca agttgcgtga agaattagct gagcttaccg ccgaattaaa gatttattca     540

gttattcaag ccgaaattaa taagcatctg tctagtagtg gcaccataaa tatccatgat     600

aaatccatta atctcatgga taaaaattta tatggttata cagatgaaga gattttttaa     660
```

-continued

```
gccagcgcag agtacaaaat tctcgagaaa atgcctcaaa ccaccattca ggtggatggg    720

agcgagaaaa aaatagtctc gataaaggac tttcttggaa gtgagaataa aagaaccggg    780

gcgttgggta atctgaaaaa ctcatactct tataataaag ataataatga attatctcac    840

tttgccacca cctgctcgga taagtccagg ccgctcaacg acttggttag ccaaaaaaca    900

actcagctgt ctgatattac atcacgtttt aattcagcta ttgaagcact gaaccgtttc    960

attcagaaat atgattcagt gatgcaacgt ctgctagatg acacgtctgg taaagcatgc   1020

gagctcggta ccagcgatgt tctggagatg tataaagcaa ttggcggtaa aatctatatt   1080

gtggatggtg atattaccaa acatattagc ctggaagcac tggatagcct gagcgaagag   1140

gaaaaagagc tgctgaatcg tattcaggtg gatagcagca tcaaattaaa tgcaaaaatg   1200

aatattttaa taagagataa acgttttcat tatgatagaa ataaaaaata taatgataaa   1260

ttaccgttat atataagtaa tcccaattat aaggtaaatg tatatgctgc ggcagattta   1320

actgcaagca ccactgcaac ggcaactctt gttgaaccag cccgcatcac tcttacatat   1380

aaggaaggcg ctccaattac aattatggcg ggcggtcatg gtgatgtagg tatgcacgta   1440

aaagagaaag agaaaaataa agatgagaat aagagaaaag atgaagaacg aaataaaaca   1500

caggaagagc atttaaagga aatcatgaaa cacattgtaa aaatagaagt aaaagggggag  1560

gaagctgtta aaaaagaggc agcagaaaag ctacttgaga aagtaccatc tgatgtttta   1620

gagatgtata aagcaattgg aggaaagata tatattgtgg atggtgatat tacaaaacat   1680

atatctttag aagcattatc tgaagataag aaaaaaataa aagacattta tgggaaagat   1740

gctttattac atgaacatta tgtatatgca aaagaaggat atgaacccgt acttgtaatc   1800

caatcttcgg aagattatgt agaaaatact gaaaaggcac tgaacgttta ttatgaaata   1860

ggtaagatat tatcaaggga tattttaagt aaaattaatc aaccatatca gaaattttta   1920

gatgtattaa ataccattaa aaatgcatct gattcagatg gacaagatct tttatttact   1980

aatcagctta aggaacatcc cacagacttt tctgtagaat tcttggaaca aaatagcaat   2040

gaggtacaag aagtatttgc gaaagctttt gcatattata tcgagccaca gcatcgtgat   2100

gttttacagc tttatgcacc ggaagctttt aattacatgg ataaatttaa cgaacaagaa   2160

ataaatctat aa                                                       2172
```

```
<210> SEQ ID NO 25
<211> LENGTH: 750
<212> TYPE: PRT
<213> ORGANISM: Artificial Sequence
<220> FEATURE:
<223> OTHER INFORMATION: LcrV-PA-F1-LFD1 fusion protein

<400> SEQUENCE: 25

Arg Gly Ser His His His His His His Gly Ser Met Glu Thr Ile Arg
1               5                   10                  15

Ala Tyr Glu Gln Asn Pro Gln His Phe Ile Glu Asp Leu Glu Lys Val
            20                  25                  30

Arg Val Glu Gln Leu Thr Gly His Gly Ser Ser Val Leu Glu Glu Leu
        35                  40                  45

Val Gln Leu Val Lys Asp Lys Asn Ile Asp Ile Ser Ile Lys Tyr Asp
    50                  55                  60

Pro Arg Lys Asp Ser Glu Val Phe Ala Asn Arg Val Ile Thr Asp Asp
65                  70                  75                  80

Ile Glu Leu Leu Lys Lys Ile Leu Ala Tyr Phe Leu Pro Glu Asp Ala
                85                  90                  95
```

-continued

```
Ile Leu Lys Gly Gly His Tyr Asp Asn Gln Leu Gln Asn Gly Ile Lys
            100                 105                 110

Arg Val Lys Glu Phe Leu Glu Ser Ser Pro Asn Thr Gln Trp Glu Leu
        115                 120                 125

Arg Ala Phe Met Glu Thr Ala Val Met Glu Thr His Phe Ser Leu Thr
    130                 135                 140

Ala Asp Arg Ile Asp Asp Asp Ile Leu Lys Val Ile Val Asp Ser Met
145                 150                 155                 160

Glu Thr Asn His His Gly Asp Ala Arg Ser Lys Leu Arg Glu Glu Leu
                165                 170                 175

Ala Glu Leu Thr Ala Glu Leu Lys Ile Tyr Ser Val Ile Gln Ala Glu
            180                 185                 190

Ile Asn Lys His Leu Ser Ser Ser Gly Thr Ile Asn Ile His Asp Lys
        195                 200                 205

Ser Ile Asn Leu Met Glu Thr Asp Lys Asn Leu Tyr Gly Tyr Thr Asp
    210                 215                 220

Glu Glu Ile Phe Lys Ala Ser Ala Glu Tyr Lys Ile Leu Glu Lys Met
225                 230                 235                 240

Glu Thr Pro Gln Thr Thr Ile Gln Val Asp Gly Ser Glu Lys Lys Ile
                245                 250                 255

Val Ser Ile Lys Asp Phe Leu Gly Ser Glu Asn Lys Arg Thr Gly Ala
            260                 265                 270

Leu Gly Asn Leu Lys Asn Ser Tyr Ser Tyr Asn Lys Asp Asn Asn Glu
        275                 280                 285

Leu Ser His Phe Ala Thr Thr Cys Ser Asp Lys Ser Arg Pro Leu Asn
    290                 295                 300

Asp Leu Val Ser Gln Lys Thr Thr Gln Leu Ser Asp Ile Thr Ser Arg
305                 310                 315                 320

Phe Asn Ser Ala Ile Glu Ala Leu Asn Arg Phe Ile Gln Lys Tyr Asp
                325                 330                 335

Ser Val Met Glu Thr Gln Arg Leu Leu Asp Asp Thr Ser Gly Lys Ala
            340                 345                 350

Cys Glu Leu Gly Thr Ser Asp Val Leu Glu Met Glu Thr Tyr Lys Ala
        355                 360                 365

Ile Gly Gly Lys Ile Tyr Ile Val Asp Gly Asp Ile Thr Lys His Ile
    370                 375                 380

Ser Leu Glu Ala Leu Asp Ser Leu Ser Glu Glu Glu Lys Glu Leu Leu
385                 390                 395                 400

Asn Arg Ile Gln Val Asp Ser Ser Ile Lys Leu Asn Ala Lys Met Glu
                405                 410                 415

Thr Asn Ile Leu Ile Arg Asp Lys Arg Phe His Tyr Asp Arg Asn Lys
            420                 425                 430

Lys Tyr Asn Asp Lys Leu Pro Leu Tyr Ile Ser Asn Pro Asn Tyr Lys
        435                 440                 445

Val Asn Val Tyr Ala Ala Ala Asp Leu Thr Ala Ser Thr Thr Ala Thr
    450                 455                 460

Ala Thr Leu Val Glu Pro Ala Arg Ile Thr Leu Thr Tyr Lys Glu Gly
465                 470                 475                 480

Ala Pro Ile Thr Ile Met Glu Thr Ala Gly Gly His Gly Asp Val Gly
                485                 490                 495

Met Glu Thr His Val Lys Glu Lys Glu Lys Asn Lys Asp Glu Asn Lys
            500                 505                 510

Arg Lys Asp Glu Glu Arg Asn Lys Thr Gln Glu Glu His Leu Lys Glu
        515                 520                 525
```

-continued

```
Ile Met Glu Thr Lys His Ile Val Lys Ile Glu Val Lys Gly Glu Glu
    530                 535                 540

Ala Val Lys Lys Glu Ala Ala Glu Lys Leu Leu Glu Lys Val Pro Ser
545                 550                 555                 560

Asp Val Leu Glu Met Glu Thr Tyr Lys Ala Ile Gly Gly Lys Ile Tyr
                565                 570                 575

Ile Val Asp Gly Asp Ile Thr Lys His Ile Ser Leu Glu Ala Leu Ser
            580                 585                 590

Glu Asp Lys Lys Lys Ile Lys Asp Ile Tyr Gly Lys Asp Ala Leu Leu
        595                 600                 605

His Glu His Tyr Val Tyr Ala Lys Glu Gly Tyr Glu Pro Val Leu Val
    610                 615                 620

Ile Gln Ser Ser Glu Asp Tyr Val Glu Asn Thr Glu Lys Ala Leu Asn
625                 630                 635                 640

Val Tyr Tyr Glu Ile Gly Lys Ile Leu Ser Arg Asp Ile Leu Ser Lys
                645                 650                 655

Ile Asn Gln Pro Tyr Gln Lys Phe Leu Asp Val Leu Asn Thr Ile Lys
            660                 665                 670

Asn Ala Ser Asp Ser Asp Gly Gln Asp Leu Leu Phe Thr Asn Gln Leu
        675                 680                 685

Lys Glu His Pro Thr Asp Phe Ser Val Glu Phe Leu Glu Gln Asn Ser
    690                 695                 700

Asn Glu Val Gln Glu Val Phe Ala Lys Ala Phe Ala Tyr Tyr Ile Glu
705                 710                 715                 720

Pro Gln His Arg Asp Val Leu Gln Leu Tyr Ala Pro Glu Ala Phe Asn
                725                 730                 735

Tyr Met Glu Thr Asp Lys Phe Asn Glu Gln Glu Ile Asn Leu
            740                 745                 750


<210> SEQ ID NO 26
<211> LENGTH: 5
<212> TYPE: PRT
<213> ORGANISM: Bacillus anthracis

<400> SEQUENCE: 26

Ile Gln Asn Leu Phe
1               5


<210> SEQ ID NO 27
<211> LENGTH: 4
<212> TYPE: PRT
<213> ORGANISM: Bacillus anthracis

<400> SEQUENCE: 27

Glu Leu Gly Thr
1
```